(12) United States Patent
Gutfinger et al.

(10) Patent No.: US 8,202,224 B2
(45) Date of Patent: Jun. 19, 2012

(54) SYSTEM AND METHOD FOR CALIBRATING CARDIAC PRESSURE MEASUREMENTS DERIVED FROM SIGNALS DETECTED BY AN IMPLANTABLE MEDICAL DEVICE

(75) Inventors: Dan E. Gutfinger, Agoura Hills, CA (US); Neal L. Eigler, Malibu, CA (US); Dorin Panescu, San Jose, CA (US); James S. Whiting, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 1091 days.

(21) Appl. No.: 12/109,304

(22) Filed: Apr. 24, 2008

(65) Prior Publication Data

US 2008/0262361 A1 Oct. 23, 2008

Related U.S. Application Data

(63) Continuation-in-part of application No. 11/559,235, filed on Nov. 13, 2006, now Pat. No. 7,794,404.

(51) Int. Cl.
- *A61B 5/0205* (2006.01)
- *A61B 5/021* (2006.01)
- *A61B 5/02* (2006.01)

(52) U.S. Cl. ........ 600/485; 600/486; 600/506; 600/508; 600/513; 600/517; 600/526; 600/547; 607/17; 607/23

(58) Field of Classification Search ............... 600/485, 600/486, 506, 508, 513, 517, 526, 547; 607/17, 607/23

See application file for complete search history.

(56) References Cited

U.S. PATENT DOCUMENTS

| | | | |
|---|---|---|---|
| 4,712,555 | A | 12/1987 | Thornander et al. |
| 4,788,980 | A | 12/1988 | Mann et al. |
| 4,940,052 | A | 7/1990 | Mann et al. |
| 4,944,298 | A | 7/1990 | Sholder |
| 5,003,976 | A | 4/1991 | Alt |
| 5,466,254 | A | 11/1995 | Helland |
| 5,476,483 | A | 12/1995 | Bornzin et al. |
| 5,615,684 | A | 4/1997 | Hagel et al. |
| 5,676,141 | A | 10/1997 | Hollub |
| 5,800,467 | A | 9/1998 | Park et al. |
| 6,044,297 | A | 3/2000 | Sheldon et al. |
| 6,223,082 | B1 | 4/2001 | Bakels et al. |
| 6,249,705 | B1 | 6/2001 | Snell |
| 6,328,699 | B1 | 12/2001 | Eigler et al. |
| 6,438,408 | B1 | 8/2002 | Mulligan et al. |
| 6,480,733 | B1 | 11/2002 | Turcott |

(Continued)

FOREIGN PATENT DOCUMENTS

WO 2007050493 A1 5/2007

*Primary Examiner* — Carl H Layno
*Assistant Examiner* — Allen Porter, Jr.

(57) ABSTRACT

Various techniques are provided for calibrating and estimating left atrial pressure (LAP) using an implantable medical device, based on impedance, admittance or conductance parameters measured within a patient. In one example, default conversion factors are exploited for converting the measured parameters to estimates of LAP. The default conversion factors are derived from populations of patients. In another example, a correlation between individual conversion factors is exploited to allow for more efficient calibration. In yet another example, differences in thoracic fluid states are exploited during calibration. In still yet another example, a multiple stage calibration procedure is described, wherein both invasive and noninvasive calibration techniques are exploited. In a still further example, a therapy control procedure is provided, which exploits day time and night time impedance/admittance measurements.

8 Claims, 43 Drawing Sheets

U.S. PATENT DOCUMENTS

| | | |
|---|---|---|
| 6,512,952 B2 | 1/2003 | Stahmann et al. |
| 6,572,557 B2 | 6/2003 | Tchou et al. |
| 6,575,912 B1 | 6/2003 | Turcott |
| 6,628,988 B2 | 9/2003 | Kramer et al. |
| 6,643,546 B2 | 11/2003 | Mathis et al. |
| 6,643,548 B1 | 11/2003 | Mai et al. |
| 6,645,153 B2 | 11/2003 | Kroll et al. |
| 6,741,885 B1 | 5/2004 | Park et al. |
| 6,748,261 B1 | 6/2004 | Kroll |
| 6,754,530 B2 | 6/2004 | Bakels et al. |
| 6,970,742 B2 | 11/2005 | Mann et al. |
| 7,115,095 B2 | 10/2006 | Eigler et al. |
| 7,248,925 B2 | 7/2007 | Bruhns et al. |
| 2004/0019285 A1 | 1/2004 | Eigler et al. |
| 2005/0215914 A1* | 9/2005 | Bornzin et al. ............ 600/508 |
| 2007/0093872 A1 | 4/2007 | Chirife et al. |
| 2007/0093873 A1 | 4/2007 | Chirife et al. |
| 2007/0093874 A1 | 4/2007 | Chirife et al. |

* cited by examiner

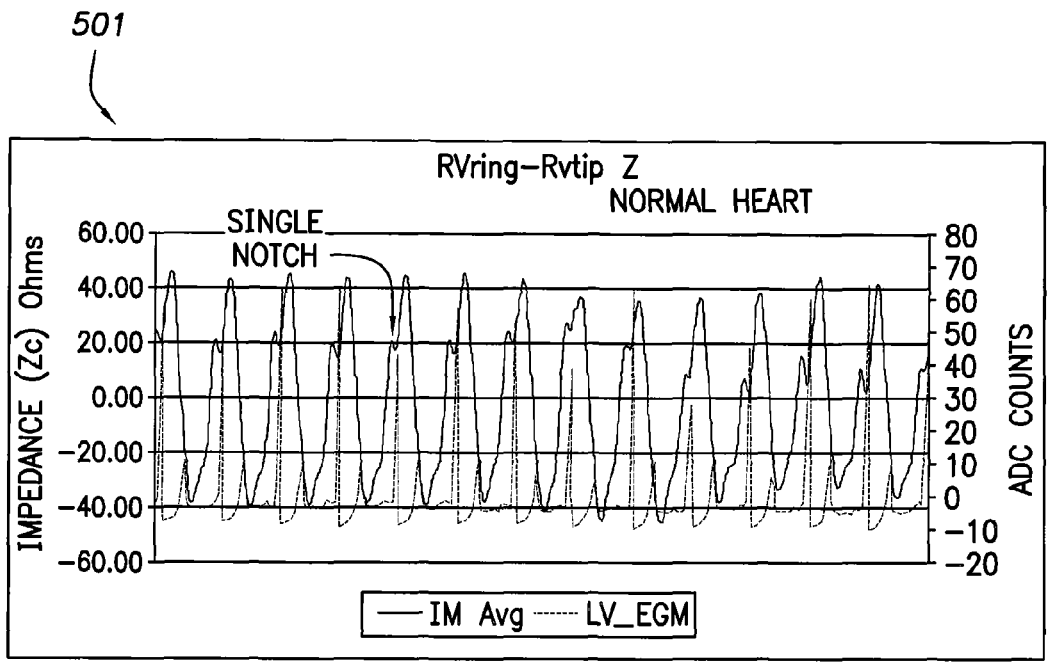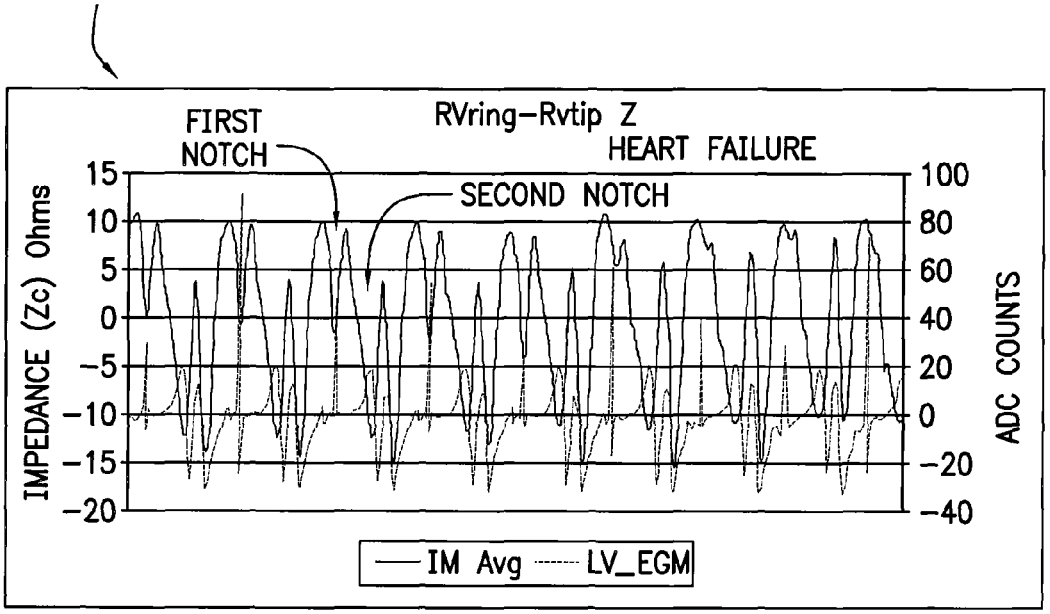
FIG. 16

SYSTEM AND METHOD FOR CALIBRATING CARDIAC PRESSURE MEASUREMENTS DERIVED FROM SIGNALS DETECTED BY AN IMPLANTABLE MEDICAL DEVICE

RELATED APPLICATIONS

This application is a Continuation-in-Part of U.S. patent application Ser. No. 11/559,235, filed Nov. 13, 2006, now U.S. Pat. No. 7,794,404, entitled "System and Method for Estimating Cardiac Pressure Using Parameters Derived from Impedance Signals Detected by an Implantable Medical Device" and claims priority therefrom.

This application is also related to U.S. Provisional Patent Application No. 60/787,884, filed Mar. 31, 2006 entitled "Tissue Characterization Using Intracardiac Impedances with an Implantable Lead System."

This application is also related to the following U.S. patent application Ser. Nos.:
11/558,101, filed Nov. 9, 2006;
11/557,851, filed Nov. 8, 2006;
11/557,870, filed Nov. 8, 2006;
11/557,882, filed Nov. 8, 2006; and
11/558,088, filed Nov. 9, 2006; each entitled "Systems and Methods to Monitor and Treat Heart Failure Conditions." Each of the foregoing applications is fully incorporated by reference herein, including the appendices thereof.

FIELD OF THE INVENTION

The invention relates generally to implantable medical devices such as pacemakers and implantable cardioverter defibrillators (ICDs) and in particular to techniques for estimating cardiac pressure (particularly left atrial pressure (LAP)) to detect and evaluate heart failure and related conditions.

BACKGROUND OF THE INVENTION

Heart failure is a debilitating disease in which abnormal function of the heart leads to inadequate blood flow to fulfill the needs of the tissues and organs of the body. Typically, the heart loses propulsive power because the cardiac muscle loses capacity to stretch and contract. Often, the ventricles do not adequately fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds cardiac muscle causing the ventricles to grow in volume in an attempt to pump more blood with each heartbeat, i.e. to increase the stroke volume. This places a still higher demand on the heart's oxygen supply. If the oxygen supply falls short of the growing demand, as it often does, further injury to the heart may result, typically in the form of myocardial ischemia or myocardial infarction. The additional muscle mass may also stiffen the heart walls to hamper rather than assist in providing cardiac output. Often, electrical and mechanical dyssynchronies develop within the heart such that the various chambers of the heart no longer beat in a synchronized manner, degrading overall cardiac function. A particularly severe form of heart failure is congestive heart failure (CHF) wherein the weak pumping of the heart or compromised filling leads to build-up of fluids in the lungs and other organs and tissues.

Many patients susceptible to CHF, particularly the elderly, have pacemakers, ICDs or other implantable medical devices implanted therein, or are candidates for such devices. Accordingly, it is desirable to provide techniques for detecting and tracking CHF using such devices. One particularly effective parameter for detecting and tracking CHF is cardiac pressure, particularly LAP, i.e. the blood pressure within the left atrium of the patient. Reliable detection of LAP would not only permit the implanted device to track CHF for diagnostic purposes but to also control therapies applied to address CHF such as cardiac resynchronization therapy (CRT). CRT seeks to normalize asynchronous cardiac electrical activation and the resultant asynchronous contractions by delivering synchronized pacing stimulus to the ventricles using pacemakers or ICDs equipped with biventricular pacing capability. The pacing stimulus is typically synchronized so as to help to improve overall cardiac function. This may have the additional beneficial effect of reducing the susceptibility to life-threatening tachyarrhythmias. CRT and related therapies are discussed in, for example, U.S. Pat. No. 6,643,546 to Mathis, et al., entitled "Multi-Electrode Apparatus And Method For Treatment Of Congestive Heart Failure"; U.S. Pat. No. 6,628,988 to Kramer, et al., entitled "Apparatus And Method For Reversal Of Myocardial Remodeling With Electrical Stimulation"; and U.S. Pat. No. 6,512,952 to Stahmann, et al., entitled "Method And Apparatus For Maintaining Synchronized Pacing". Reliable estimates of LAP derived from impedance signals would also allow the dosing of heart failure medications (such as diuretics) to be properly titrated so as to minimize the number of episodes of acute heart failure decompensation. Another advantage to providing reliable estimates of LAP from impedance signals is that physicians are more familiar with LAP values. Hence, LAP estimates could be provided to the physician via diagnostic displays, rather than raw impedance signal values, which the physicians might find difficult to interpret.

However, LAP is a difficult parameter to detect since it is not clinically appealing to place a blood pressure sensor directly in the left atrium due to the chronic risk of thromboembolic events, as well as risks associated with the transseptal implant procedure itself. Accordingly, various techniques have been developed for estimating LAP based on other parameters that can be more safely sensed by a pacemaker or ICD. In this regard, some particularly promising techniques have been developed that use electrical impedance signals to estimate LAP. For example, impedance signals can be sensed along a sensing vector passing through the left atrium, such as between an electrode mounted on a left ventricular (LV) lead and another electrode mounted on a right atrial (RA) lead. The sensed impedance is affected by the blood volume inside the left atrium, which is in turn reflected by the pressure in the left atrium. Accordingly, there is a correlation between the sensed impedance and LAP, which can be exploited to estimate LAP and thereby also track CHF. Another example may be the impedance signals sensed along a sensing vector passing through the lung, such as between an electrode mounted on the a left ventricular (LV) pacing lead and another electrode representing the device case (Case) containing the pulse generator within a subcutaneous thoracic pocket. The sensed impedance is affected by the fluid volume within the lung/thorax, which is in turn reflected and proportional to the pressure within the pulmonary veins that is equivalent to the LAP. See, for example, techniques described in the related patent applications, cited above. See, also, U.S. patent application Ser. No. 11/558,194, by Panescu et al., entitled "Closed-Loop Adaptive Adjustment of Pacing Therapy based on Cardiogenic Impedance Signals Detected by an Implantable Medical Device", which is incorporated by reference herein.

Although electrical impedance can be used to estimate LAP, it is difficult to reliably calibrate such impedance-based estimation techniques. That is, it can be difficult to accurately and reliably convert detected electrical impedance values into actual LAP values. Accordingly, certain aspects of the above-cited patent applications were directed to providing improved techniques for calibrating impedance-based LAP estimation techniques.

In one example, set forth in the parent patent application (Ser. No. 11/559,235), a linear correlation between LAP and an electrical signal measured within the thorax of the patient is exploited to estimate cardiac pressure. The electrical signal can be, e.g., impedance (Z), admittance (Y), or conductance (G), as measured along a sensing vector passing through the heart of the patient. Note that these electrical parameters are related. Admittance and impedance represent forms of immittance, with admittance being the numerical reciprocal of impedance. Conductance is the numerical reciprocal of resistance. In general, impedance and admittance are vector quantities, which may be represented by complex numbers (having real and imaginary components.) Unless otherwise noted, only the real portion of the impedance or admittance vector is exploited within the equations provided herein. The real component of impedance is resistance. The real component of admittance is conductance. Hence, when exploiting only the real components of these values, conductance can be regarded as the reciprocal of impedance. Likewise, when exploiting only the real components, admittance can be regarded as the reciprocal of resistance.

Suitable conversion factors (also referred to as calibration coefficients) are determined via linear regression, which relate the particular measured electrical signal to LAP, such that subsequent signal measurements can be used to estimate LAP. In one particular example, the conversion factors are "slope" and "baseline" values representative of the linear correlation. Slope may also be referred to as "gain". Baseline may also be referred to as "offset" or bLAP (i.e. baseline LAP.)

The initial determination of the appropriate slope and baseline conversion factors for use within the patient is referred to as calibration. The conversion factors are preferably re-calibrated as needed to ensure reliable LAP estimates despite anatomical or physiological changes within the patient. That is, the slope and baseline values are recalculated or adjusted, either periodically or on-demand.

The parent application introduced various calibration and re-calibration techniques for use in determining the slope and baseline values. In one illustrative example where the electrical parameter to be measured within the patient is conductance (G), the appropriate slope and baseline values ($Slope_G$ and $bLAP_G$) are determined during an initial calibration procedure based on the assumption that there is a linear relationship between conductance and LAP. To calibrate the slope and baseline values for a particular patient, a "two-point" calibration procedure is employed wherein a first conductance calibration value ($G_1$) and a corresponding first cardiac pressure calibration value ($LAP_1$) are measured within the patient at a first point in time. Then, a second conductance calibration value ($G_2$) and a corresponding second cardiac pressure calibration value ($LAP_2$) are measured at a second point time within the patient. The first and second pressure calibration values ($LAP_1$, $LAP_2$) may be measured within the patient using, e.g., a Swan-Ganz catheter equipped to measure pulmonary capillary wedge pressure (PCWP). The times are chosen such that the first and second cardiac pressure values ($LAP_1$, $LAP_2$) differ substantially from one another (and so the conductance calibration values also differ substantially from one another). In one particular example, the first calibration values ($G_1$, $LAP_1$) are detected while the patient is at rest; whereas the second calibration values ($G_2$, $LAP_2$) are detected while the patient is subject to a condition significantly affecting cardiac pressure, such as isometric muscle contraction, vasodilatation, vasoconstriction, rapid pacing or performance of the Valsalva maneuver by the patient. The slope value is then calibrated by calculating:

$$Slope_G=(LAP_2-LAP_1)/(G_2-G_1).$$

The baseline value is then calibrated by calculating:

$$bLAP_G=LAP_2-Slope_G*G_1.$$

Thereafter, LAP is estimated based on newly-detected conductance values using:

$$eLAP=G*Slope_G+bLAP_G$$

where eLAP represents the estimated LAP. Alternately, the term zLAP may be used to denote eLAP, where zLAP represents a LAP estimate derived from the impedance signal.

Similar "two-point" techniques may be exploited for calibrating slope and baseline for use with impedance (Z) values or admittance (Y) values. In general, a pair of calibration values, referred to as $C_1$ and $C_2$, can be determined for use with any electrical parameter to be measured, so long as there is a linear relationship between the measured parameter and LAP. Slope is calculated using:

$$Slope=(LAP_2-LAP_1)/(C_2-C_1).$$

Baseline is then calculated using:

$$Baseline=LAP_1-Slope*C_1.$$

Any of the two-point calibration techniques can be expanded to employ multiple data points (i.e. N data points) by exploiting linear regression or other suitable techniques.

In some implementations, particular components of a raw impedance signal ($Z_0$) are exploited, such as a high-frequency "cardiogenic" impedance signal ($Z_C$) representative of the beating of the heart of the patient, a low-frequency respiratory impedance signal ($Z_R$) representative of the respiration of the patient, or an ultra-low frequency circadian impedance signal representative of daily postural/humeral variations of the patient seen in the raw impedance signal ($Z_0$). Corresponding components of the raw admittance signal ($Y_0$) may likewise be exploited. Suitable values for slope and baseline are calibrated for use with the particular signal components to be used.

In another illustrative example set forth in the parent patent application, a cardiogenic pulse amplitude is derived from a cardiogenic impedance signal ($Z_C$) then exploited to estimate LAP. That is, LAP can be estimated based on the cardiogenic pulse amplitude value using appropriate conversion factors. For example, LAP may be estimated using:

$$eLAP=\text{Cardiogenic\_Pulse\_Amplitude}*Slope_{CARDIOGENIC}+bLAP_{CARDIOGENIC}$$

where Cardiogenic_Pulse_Amplitude is an amplitude value derived from the impedance signal (Z) and $Slope_{CARDIOGENIC}$ and $bLAP_{CARDIOGENIC}$ are conversion values derived specifically for use converting cardiogenic pulse amplitude values to LAP values. The Slope$_{CARDIOGENIC}$ and bLAP$_{CARDIOGENIC}$ conversion factors may be calibrated using similar techniques used to calibrate Slope$_G$ and bLAP$_G$. The pulse amplitude extracted from the cardiogenic impedance signal ($Z_C$) may be restricted to certain portions of the cardiac cycle that may be representative of the venous filling phase within the left atrium (i.e., the portion of the cardiac cycle relative to the cardiac electrogram R-wave corresponding to when the V-wave within the LAP waveform occurs).

In yet another illustrative example set forth in the parent patent application, the parameter derived from the electrical impedance signal (Z) is the circadian pulse amplitude value derived from the circadian component of the raw impedance signal ($Z_0$). The circadian pulse amplitude represents the daily postural-dependent thoracic volume variation in the impedance signal and is preferably calculated once per day. Within well compensated heart failure patients, there is typically a significant daily variation in impedance and so the circadian pulse amplitude may be significant, e.g. 20 ohms or more. Within patients with decompensated heart failure, however, there is typically little or no significant daily variation in impedance and so the circadian pulse amplitude is at or near zero. Hence, progression of heart failure correlates with a decrease in circadian pulse amplitudes. As already noted, there is also a correlation with LAP and heart failure, i.e. LAP increases due to progression of heart failure. Accordingly, there is a correlation between decreasing circadian pulse amplitudes and increasing LAP. That is, LAP can be estimated based on the circadian pulse amplitude value using appropriate conversion factors. For example, LAP may be estimated using:

$$eLAP = \text{Circadian\_Pulse\_Amplitude} * \text{Slope}_{CIRCADIAN} + bLAP_{CIRCADIAN}$$

where in Circadian_Pulse_Amplitude is an individual circadian pulse amplitude value derived from the impedance signal over a twenty-four hour period and wherein Slope$_{CIRCADIAN}$ and bLAP$_{CIRCADIAN}$ are conversion values derived specifically for use converting circadian pulse amplitude values to LAP values. The Slope$_{CIRCADIAN}$ and bLAP$_{CIRCADIAN}$ conversion factors may be calibrated using similar techniques used to calibrate Slope$_G$ and bLAP$_G$.

Still other LAP estimation and calibration procedures were set forth in the parent patent application, including techniques exploiting signal morphology fractionation parameters. For the sake of completeness, all of these techniques are also described in detail herein below.

Although the estimation and calibration techniques of the parent application are effective, it is desirable to provide still other estimation or calibration techniques. It is to this end that the techniques of the present invention are primarily directed.

SUMMARY

In accordance with a first exemplary embodiment, a method is provided for estimating cardiac pressure within a patient using an implantable medical device, which exploits default conversion factors derived from a patient population. Briefly, an electrical field (such as the electrical field of an impedance detection pulse) is applied to tissues of the patient, including cardiac tissues. A parameter influenced by the electrical field is measured. Examples include impedance values (Z) or admittance values (Y) measured in response to an immittance detection pulse. Default conversion factors are input for use in converting the measured value to an estimated cardiac pressure value, wherein the default conversion factors are values representative of a linear correlation between the measured parameter and the cardiac pressure derived from a population of patients. The conversion factors may be, for example, slope (or Gain) and baseline (or Offset) values derived from the patient population using linear regression techniques. Then, LAP or other cardiac pressure values are estimated within the patient by applying the default conversion factors to the parameters derived from the detection pulse.

By exploiting default conversion factors derived from a patient population, the implantable device need not pre-determine specific values for use with the particular patient in which the device is implanted. In some examples, the device uses the default values until patient-specific values can be ascertained. In other examples, the device continues to use the default values, particularly if the default values are deemed to provide an adequate estimate of LAP within the patient. Also, in some examples, different sets of default conversion factors are employed based on patient age, gender and weight or still other parameters (e.g., type of heart failure (systolic or diastolic), left ventricular ejection fraction, body surface area, etc.). That is, the appropriate set of default conversion factors is input based on the patient's own age, gender and weight for use in estimating LAP.

Thereafter, heart failure may be detected or tracked based on the LAP estimate. Upon detecting of the onset of heart failure, appropriate warning signals may be generated for alerting the patient. In some implementations, the warning signals, as well as appropriate diagnostic information (such as the estimated LAP values), are automatically forwarded to the physician by a suitable communication system. The physician may then adjust patient medication or other forms of therapy.

Depending upon the capabilities of the implanted device, therapy may also be automatically applied or modified by the device in response to heart failure. For example, if the device is equipped to perform CRT, then CRT pacing may be initiated or otherwise controlled based on LAP. Also, if the implanted system is equipped with a drug pump, appropriate medications (such as diuretics) potentially may be administered directly to the patient, depending upon the programming of the device. Alternatively, the estimated LAP may be presented directly to the patient using a handheld or a bedside monitor, so that the patient may utilize the estimated LAP reading to self-titrate oral dosages of heart failure medications based on a sliding scale prescription provided to the patient in advance.

In accordance with a second exemplary embodiment, a method is provided for calibrating a cardiac pressure estimation system of an implantable medical device for implant within a patient, which takes into account a possible linear relationship between slope and baseline values or other conversion factors. Assuming such a linear relationship, one of the conversion factors (e.g. slope) may be exploited to determine the other of the conversion factors (e.g. baseline), such that both conversion factors need not be determined, at least during re-calibration. Briefly, the cardiac pressure estimation system is initially calibrated by determining an initial set of conversion factors for the patient for use in converting measured electrical parameters within the patient to cardiac pressure estimates. A determination is subsequently made as to whether there is a linear relationship between the conversion factors for the patient (e.g. a linear relationship between the slope and baseline values.) The cardiac pressure estimation system is then re-calibrated by selectively adjusting the initial conversion factors based, at least in part, on whether a linear relationship was found between the conversion factors for the patient.

In an illustrative example, an initial pair of slope and baseline conversion factors is determined for the patient using any suitable calibration procedure. The conversion factors are used by the implantable device to estimate LAP or other cardiac pressure values from electrical parameters (e.g. impedance or admittance) measured within the patient. Periodically, the slope and baseline conversion factors are re-calibrated, again using any suitable calibration technique. The various slope and baseline pairs are recorded within the device for subsequent review. Once a sufficient number of pairs of slope and baseline values have been stored, the device examines the values to determine whether there is a linear relationship between slope and baseline. Linear regression techniques maybe exploited. If there is a linear relationship between slope and baseline, then, during subsequent re-calibration procedures, the device need not separately determine both slope and baseline. Rather, it is sufficient to determine only one of the values (e.g. slope) and then the other value (e.g. baseline) can be calculated from the first value by exploiting the linear relationship therebetween.

Thus, the second exemplary embodiment exploits the recognition that, within at least some patients, slope and baseline conversion factors are not independent of one another but are instead linearly correlated. Within such patients, the slope and baseline values can be re-calibrated without requiring "two-point" calibration, i.e. without requiring at least two sets of calibration values, such as a first set of calibration values ($Z_1$, $LAP_1$) detected while the patient is at rest and a second set of calibration values ($Z_2$, $LAP_2$) detected while the patient is subject to a condition significantly affecting cardiac pressure. Rather, it is sufficient to obtain one new pair of calibration values (e.g. $Z_1$, $LAP_1$) to recalibrate both slope and baseline, thereby allowing for more convenient recalibration.

Note that, within some patients, slope and baseline values are not linearly correlated and hence "two-point" calibration techniques may be needed. Also note that, within some patients, the baseline value remains substantially unchanged and only the slope value varies. Hence, with such patients, once the slope and baseline values have been initially calibrated, it is sufficient to re-calibrate only the slope values. In still other patients, the slope value remains substantially unchanged and only the baseline value varies. Hence, with such patients, it is sufficient to re-calibrate only the baseline values.

As a practical matter, it is thus advantageous to determine, for a particular patient or population of patients, the relationship (if any) between slope and baseline within the patient, so the most efficient re-calibration procedures may be exploited. This may be achieved, as noted, by determining and tracking slope and baseline conversion factors for the patient over a period of time to ascertain whether there is a linear correlation between the two factors. Such stored values may also be exploited to determine if at least one of the conversion factors remains substantially unchanged.

Broadly speaking, it has been found that the slope value is affected primarily by patient physiology (i.e. cardiac compliance, cardiac contractility, thoracic venous capacitance, blood levels/concentration, fluid levels, etc.) The baseline value is affected primarily by anatomy (i.e. lead type, lead placement, distance among the implanted leads, scar tissue formation, etc.). Hence, within a patient with generally stable physiology, but with changing anatomy (perhaps due to increasing scar tissue around lead electrodes), the slope value may remain substantially unchanged, while the baseline value varies. Within such a patient, it may be sufficient to periodically re-calibrate only the baseline value using a non-invasive technique. Conversely, within a patient with generally stable anatomy, but with changing physiology (perhaps due to a new prescription of medications affecting cardiac physiology), the baseline value may remain substantially unchanged, while the slope value varies. Within such a patient, it may be sufficient to periodically re-calibrate only the slope value, again using a non-invasive technique.

Thus, in accordance with the second exemplary embodiment, a variety of efficient re-calibration procedures are provided, depending upon the characteristics of particular patients.

In accordance with a third exemplary embodiment, a method is provided for estimating cardiac pressure within a patient using an implantable medical device, which exploits the recognition that impedance measurements obtained within a patient are inversely proportional to the trans-thoracic fluid distributed between two compartments: a fast responding intra-vascular fluid compartment and a slow responding interstitial fluid compartment. When acutely changing the physiologic state of a patient, fluid changes initially occur only within the fast responding intra-vascular fluid compartment. If the changes made to the physiologic state are sustained, then subsequent changes will also occur within the slow responding interstitial fluid compartment. If on the other hand the changes made to the physiologic state are transient, such that the original physiologic state is rapidly restored, then no changes will occur within the slow responding interstitial fluid compartment. That is, during a transition from an original physiological state to a new physiological state, the initial change in the impedance measurements reflect the initial acute changes occurring in the intra-vascular fluid compartment, while the final impedance measurements obtained reflect the steady state achieved after a sufficient amount of time has elapsed to permit both the intra-vascular and interstitial fluid compartments to equilibrate.

For example, when a patient transitions from an upright standing posture to a supine posture, an acute change occurs within the intravascular fluid compartment causing an increase in the central venous fluid volume, which is subsequently followed (assuming the patient remains supine) by an additional mobilization of interstitial fluids from the lower extremities into the central venous circulation. The increased central venous volume within the intra-vascular compartment ultimately equilibrates with the central interstitial fluid compartment and results in a steady state as long as the patient remains in the supine posture. As another example, consider a patient who performs a Valsalva maneuver sustained for a period of only ten seconds. During this short period of time, an acute change occurs within the intravascular fluid compartment causing a decrease in the central venous volume. However, there is insufficient time to permit any significant changes to occur within the interstitial fluid compartment since the physiologic change is short lived and the original physiologic state is rapidly restored.

Thus, in the third exemplary embodiment, the method for estimating cardiac pressure takes into account differences between certain physiological states within the patient, such as acute initial states that reflect primarily changes occurring only in the intra-vascular fluid compartment and chronic steady states that reflect the combination of the changes occurring in both the intra-vascular and interstitial fluid compartments. Briefly, a set of conversion factors is determined for converting measured electrical parameters to estimates of cardiac pressure, wherein the conversion factors are determined, at least in part, based on the physiological state of the patient. Then, cardiac pressure is estimated within the patient by applying the set of conversion factors to measured electrical parameters. In this manner, the appropriate set of conversion factors can be applied based on the physiological state of the patient. In one example, the physiological state is either an "acute" state, wherein the changes occurring within the patient affect only the intra-vascular fluid compartment and are relatively short-lived, or a "chronic" state, wherein the changes occurring within the patient affect both the intra-vascular and interstitial fluid compartments and are sustained so that a steady state is substantially reached.

The third exemplary embodiment thus exploits the recognition that conversion factors appropriate for use during short lived acute transitional states should not be used during sustained chronic steady states. In a first illustrative example, conversion factors are initially determined while the patient is in the acute state (that affects primarily only the intra-vascular fluid compartment), then the conversion factors are adjusted for use in the chronic state (that affects both the intra-vascular and interstitial fluid compartments.) That is, the implantable device inputs a first set of conversion factors appropriate for converting electrical parameters measured while the patient is in the acute state. The device also inputs an adjustment factor for use in adjusting the first set of conversion factors to yield a second set of conversion factors appropriate for use with electrical parameters measured while the patient is in the chronic steady state. The device then applies the adjustment factor to the acute conversion factors to generate the chronic conversion factors for use in estimating LAP within a patient while in the chronic state.

The "acute" conversion factors may be slope and baseline values (slope$_{ACUTE}$ and baseline$_{ACUTE}$) calibrated for use with a patient who has acutely transitioned into a new physiological state to allow for a change in the intra-vascular fluid compartment. The second set of "chronic" conversion factors may be slope and baseline values (slope$_{CHRONIC}$ and baseline$_{CHRONIC}$) appropriate for use with a patient who has remained at a new physiological state long enough to allow for the changes in the intravascular fluid compartment to equilibrate with interstitial fluid compartment and to reach a steady state.

The adjustment factor is used to convert the acute conversion factors (reflecting the intravascular fluid compartment change) to chronic acute conversion factors (reflecting the equilibrated intravascular and interstitial fluid compartments once a steady state has been reached.) Typically, only the slope value is adjusted using the adjustment factor. The baseline value is adjusted separately. The slope adjustment factor may be in the range of 3-5 and, in one example, is set to 4.0. That is:

$$\text{Slope}_{CHRONIC} = \text{Slope}_{ACUTE}/4.0$$

Once the slope has been adjusted, an appropriate adjustment may need to be applied to the baseline, but this can be done in a predictable manner because of the linear dependency between the slope and baseline parameters. Alternatively, the adjustment in the baseline may be determined using:

$$\text{Baseline}_{CHRONIC} = LAP_1 - \text{Slope}_{CHRONIC} * C_1$$

One particular advantage of converting acute slope values to chronic slope values is that acute values are more easily calibrated than chronic values. Initial calibration of the slope value is preferably performed in a medical center under the supervision of a clinician. For example, a Swan-Ganz catheter may be used to measure PCWP values for use in calibration along with simultaneous impedance measurements. Typically, the patient is in the acute state while being assessed within the medical center and hence acute calibration values are readily obtained. To instead obtain chronic calibration values would require that the patient rest for an extended period of time within the medical center so that the measured impedance values are representative of the chronic steady state values when both the intra-vascular and interstitial fluid compartment volumes have equilibrated. In other words, the adjustment technique allows an acute slope value to be conveniently obtained during an outpatient medical center procedure using impedance measurements made in the acute state. The acute slope value is then converted to a chronic slope value for use in estimating LAP within the patient at times when the patient is in the chronic steady state.

In a second an illustrative example, rather than generating chronic state conversion factors by adjusting acute state conversion factors, the device pre-determines both chronic state conversion factors and acute state conversion factors. In use, the device determines the current state of the patient (e.g. acute state vs. chronic state) and then retrieves and applies the appropriate set of conversion factors. This may be achieved using a posture and/or activity detector, or the like. If the patient is in the acute state, then the acute state conversion factors are used; otherwise the chronic state conversion factors are used. This is advantageous within patients who may spend significant amounts of time in either state. Preferably, the chronic state conversion factors are calibrated based on calibration data collected while the patient is in the chronic state. Alternatively, however, the chronic state conversion factors can be derived from the acute state conversion factors by applying a slope adjustment factor, as already described.

In accordance with a fourth exemplary embodiment, a method is provided for calibrating a cardiac pressure estimation system of an implantable medical device, which exploits both invasive and non-invasive calibration procedures. Briefly, an initial set of conversion factors are determined using an invasive calibration procedure wherein cardiac pressure calibration values are obtained using a pressure sensor implanted within the patient. One of the conversion factors (slope or baseline) are then adjusted using a non-invasive calibration procedure while keeping the other conversion factor unchanged.

In an illustrative example, an initial pair of slope and baseline conversion factors is determined for the patient using an invasive calibration procedure such as procedures exploiting PCWP values obtained using a Swan-Ganz catheter. The conversion factors are used by the implantable device to estimate LAP or other cardiac pressure values from electrical parameters (e.g. impedance or admittance) measured within the patient. Periodically, the slope and baseline conversion factors are re-calibrated using a non-invasive calibration technique. Exemplary non-invasive calibration procedures include procedures wherein cardiac pressure values are estimated based on: circadian immittance signals; the relative sizes of V-waves to A-waves within cardiogenic immittance signals; echocardiography signals; or by using cardiac immittance signals obtained during isometric muscle contraction, vasodilatation, vasoconstriction, rapid pacing, or the Valsalva maneuver. Note that the V-wave represents venous filling; the A-wave represents atrial contraction.

Insofar as circadian immittance signals are concerned, such signals preferably include a first set of immittance signals obtained during the day within the patient in an upright posture and a second set of immittance signals obtained during the night within the patient in a supine posture. As noted, immittance values sensed within a patient can vary from day to night based on the amount of fluid within the interstitial spaces within the thorax. Accordingly, by detecting both day and night immittance signals, the circadian variation can be exploited to more precisely calibrate the estimation procedure. As such, the implantable device is preferably equipped with detection circuitry capable of making frequently immittance measurements throughout the day to permit tracking of circadian variations in immittance.

As with the previous examples, the conversion factors may include one or more slope and baseline values representative of a linear correlation between measured electrical parameters (e.g. impedance, admittance or conductance) within the patient and LAP or other forms of cardiac pressure within the patient. The conversion factors are calibrated and re-calibrated by measuring or otherwise obtaining sets of electrical parameters within the patient and sets of cardiac pressure estimates within the patient and then determining the slope and baseline values therefrom using linear regression or other suitable techniques. By starting with an invasive calibration procedure under clinician supervision, accurate slope and baseline values can be initially ascertained for the patient. Thereafter, non-invasive procedures may be used to adjust the calibration to account for changes within the patient due to changes in physiology, anatomy or due to the effect of prescribed medications. As already noted, depending upon the particular patient, efficient re-calibration procedures may be employed, where appropriate, which do not require re-calibration of both the slope and baseline values.

In accordance with a fifth exemplary embodiment, a method is provided for controlling therapy delivered by an implantable medical device for implant within a patient. Briefly, a first set of immittance values are measured during a first interval of time such as at night within the patient while the patient is in the chronic physiological state (i.e. corresponding to a state wherein there is an equilibration of fluid volume between the intra-vascular and interstitial fluid compartments within the thorax of the patient.) LAP or other forms or cardiac pressure are then estimated within the patient, e.g., in the morning based on the first set of immittance values and therapy is controller based on the estimated cardiac pressure. For example, daily medications can be titrated based on a morning LAP estimate made at, e.g., 8:00 am. A second set of immittance values are measured during a second interval of time such as during the day within the patient while the patient is also in the chronic physiological state. LAP or other forms of cardiac pressure are then estimated within the patient, e.g., in the evening based on the second set of immittance values. Further therapy is controlled based on the newly estimated cardiac pressure. For example, nightly medications can be titrated based on the evening LAP estimate.

The various conversion techniques already exploited can be used to estimate LAP from immittance values based on slope and baseline conversion factors. In one particular example, the implantable device uses the maximum average admittance measured overnight for use in estimating the LAP in the morning and instead uses the minimum average admittance measured during the day for use in estimating the LAP in the evening. The minimum daytime admittance is typically representative of the "driest" fluid state within the thorax, as that admittance value likely corresponds to a standing posture where the patient has been standing long enough to equilibrate into the corresponding chronic fluid state. The maximum nighttime admittance is typically representative of the "wettest" fluid state within the thorax, as that admittance value likely corresponds to a supine/prone posture where the patient has been lying long enough to equilibrate into the corresponding chronic fluid state. These values are helpful in determining the appropriate therapy for the patient.

Thus, a variety of cardiac pressure estimation, calibration and therapy control techniques are set forth. In some cases, two or more of these techniques may be exploited to enhance the accuracy or efficiency of the techniques. Note that the cardiac pressure estimated in these examples (and in the other examples described herein) is an effective intracardiac pressure ($P_{eff}$) not an absolute pressure. It represents the absolute intracardiac pressure less intrathoracic pressure:

$$P_{eff} = P_{intracardiac} - P_{intrathoracic}$$

That is, the effective pressure is a type of gauge pressure. Unless otherwise noted, all estimated cardiac pressure values discussed herein, particularly estimated LAP, are effective pressure values. In some techniques described herein, such as techniques where the Valsalva maneuver is exploited to reduce intracardiac pressure within the patient for the calibration purposes, the distinction between effective pressure and absolute pressure is particularly important and effective pressure should be used. In those examples, the term "effective LAP" may be used as a reminder that effective pressures are used. In any case, effective pressure values are typically more useful from a clinical perspective than absolute pressure values.

BRIEF DESCRIPTION OF THE DRAWINGS

Further features and advantages of the invention may be more readily understood by reference to the following description taken in conjunction with the accompanying drawings, in which:

FIG. 16 is a graph illustrating exemplary cardiogenic impedance signals that may be processed in accordance with the technique of FIG. 15, and particularly illustrating the fractionation of the cardiogenic impedance signal exhibited during heart failure emulated in an animal test subject;

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Medical System

Figure 1:
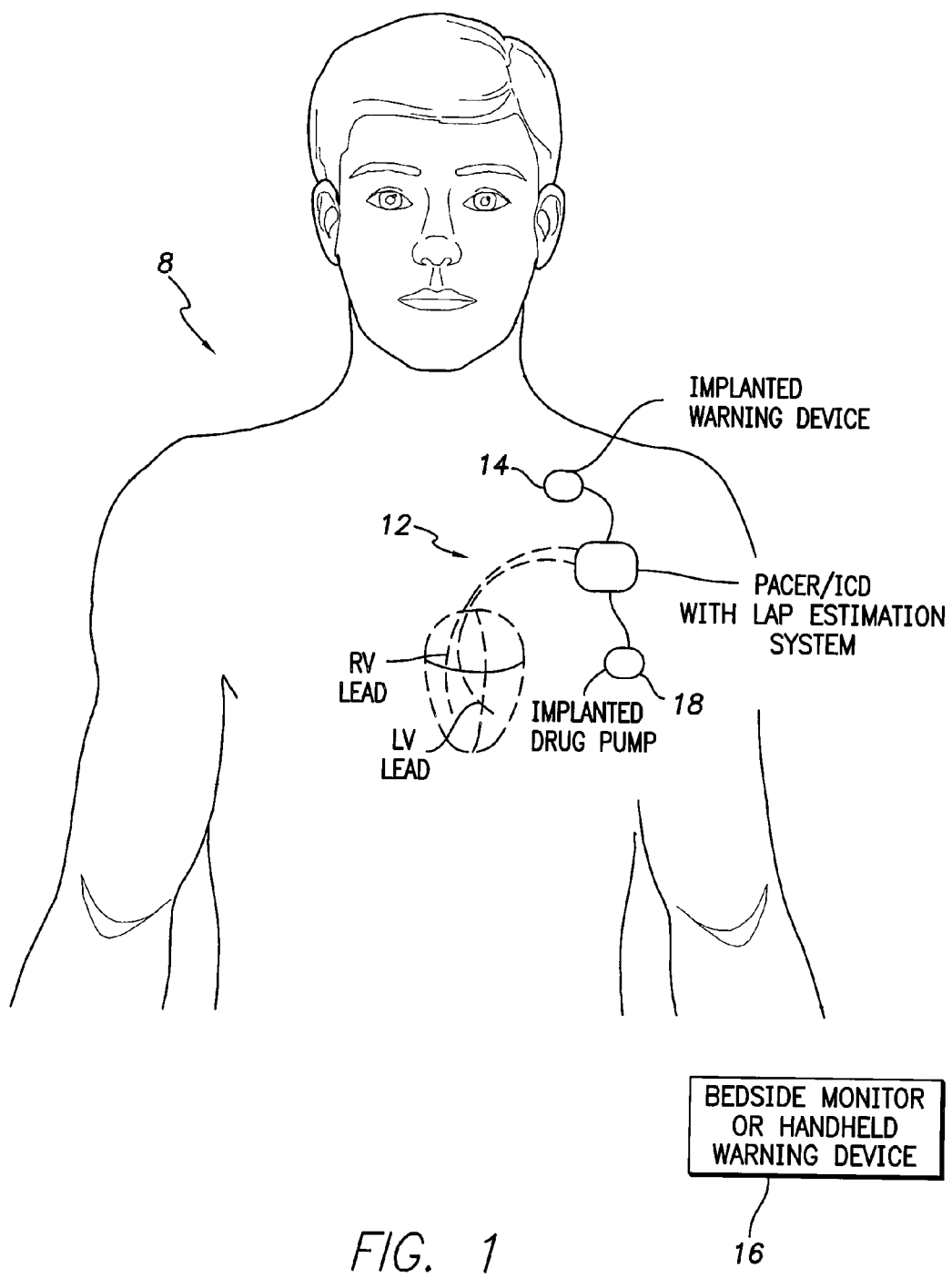
FIG. 1 is a stylized representation of an exemplary implantable medical system equipped with LAP estimation system.
Figure 19:
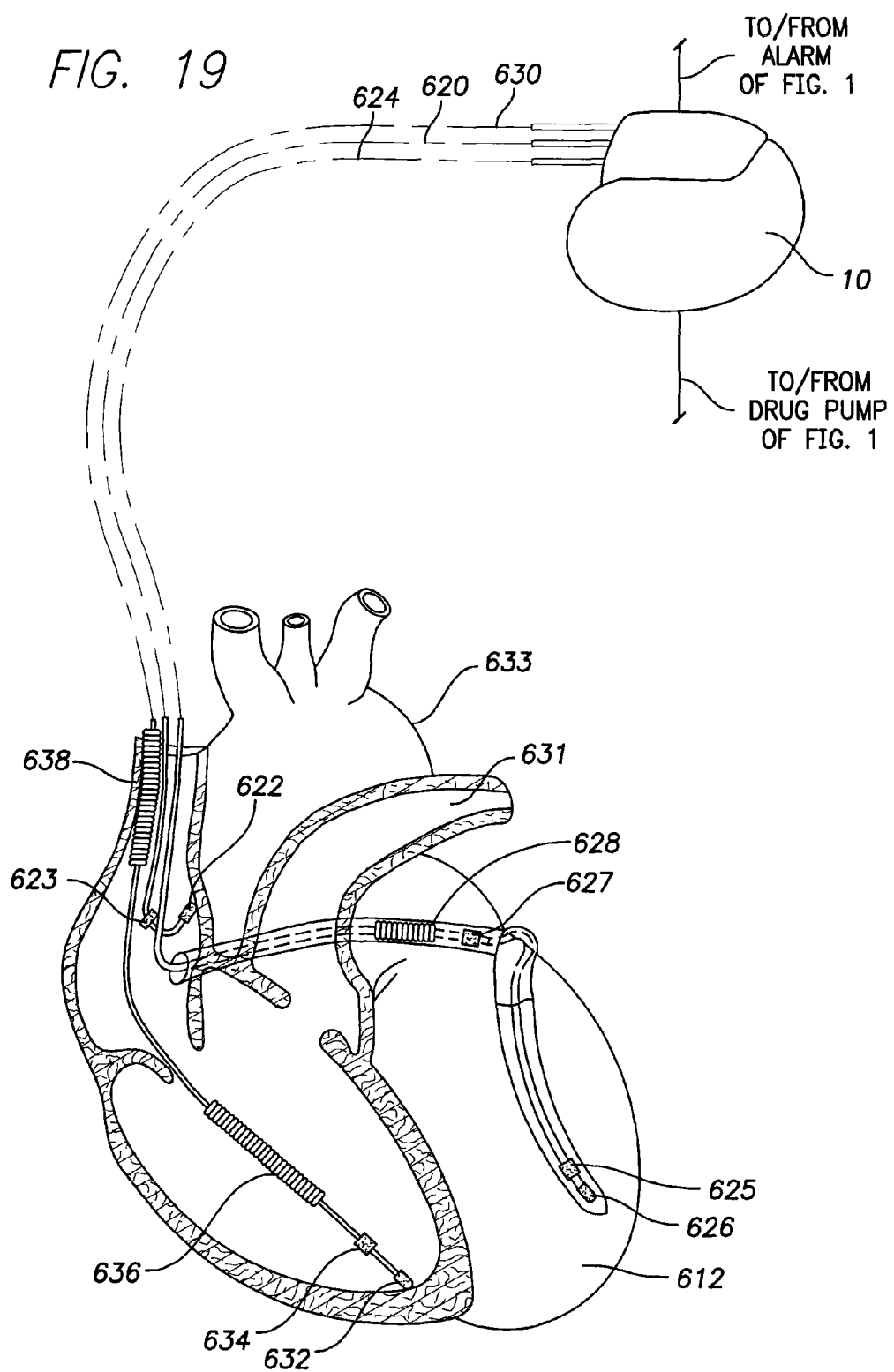
FIG. 19 is a simplified, partly cutaway view, illustrating the pacer/ICD of FIG. 1 along with at full set of leads implanted in the heart of the patient.

FIG. 1 provides a stylized representation of an exemplary implantable pacing medical system 8 capable of detecting electrical impedance signals and estimating LAP based on the impedance signals. To this end, implantable system 8 includes a pacer/ICD 10 or other cardiac stimulation device that incorporates internal components (shown individually in FIG. 20) for detecting one or more impedance signals using electrodes mounted to a set of sensing/pacing leads 12 and for estimating LAP or other cardiac pressure parameters based on various parameters derived from the impedance signals. In FIG. 1, only two leads are shown. A more complete set of leads is illustrated in FIG. 19, which is discussed below. Within the exemplary implementations described herein, LAP is estimated based on one or more of: electrical conductance values, cardiogenic pulse amplitudes, circadian rhythm pulse amplitudes, or signal morphology fractionation index values, each derived from the impedance signals detected by the pacer/ICD. Predetermined conversion factors stored within the pacer/ICD are used to convert the various parameters derived from the electrical impedance signal into LAP values or other appropriate cardiac pressure values. The conversion factors may be, for example, slope and baseline values derived during an initial calibration procedure performed by an external system, such as an external programmer (FIG. 21.) As will be explained, the baseline value may be periodically re-calibrated by the pacer/ICD itself. The slope value is assumed to remain substantially unchanged such that re-calibration of the slope is typically not required.

The pacer/ICD is also equipped to track changes in the estimated LAP values so as to detect and track CHF. CRT therapy may be initiated and controlled by the pacer/ICD, accordingly. Techniques for performing CRT are discussed in the patents to Mathis, et al., Kramer, et al., to Stahmann, et al., cited above. CRT parameters may be adaptively adjusted based on the impedance signals to improve the effectiveness of CRT using techniques set forth in the Panescu et al. patent application, "Closed-Loop Adaptive Adjustment of Pacing Therapy based on Cardiogenic Impedance Signals Detected by an Implantable Medical Device", cited above. Additionally or alternatively, the pacer/ICD can issue warning signals, if warranted. For example, if the estimated LAP exceeds a threshold or is rapidly increasing at a rate above a threshold indicative of CHF, warning signals may be generated to warn the patient, using either an internal warning device 14 or an external bedside monitor/handheld warning device 16. Internal warning device 14 may be a vibrating device or a "tickle" voltage device that, in either case, provides perceptible stimulation to the patient to alert the patient so that the patient may consult a physician. In one example, once the tickle warning is felt, the patient positions an external warning device above his or her chest. The handheld device receives short-range telemetry signals from the implanted device and provides audible or visual verification of the warning signal. The handheld warning device thereby provides confirmation of the warning to the patient along with a display of the estimated LAP, who may be otherwise uncertain as to the reason for the internally generated warning signal. For further information regarding this warning/notification technique, see U.S. patent application Ser. No. 11/043,612, of Kil et al., filed Jan. 25, 2005, entitled "System and Method for Distinguishing Among Ischemia, Hypoglycemia and Hyperglycemia Using an Implantable Medical Device."

If a bedside monitor is provided, the bedside monitor provides audible or visual alarm signals to alert the patient as well as textual or graphic displays. In addition, diagnostic information pertaining to the deteriorating cardiac condition is transferred to the bedside monitor or is stored within the pacer/ICD for subsequent transmission to an external programmer or internet network site (not shown in FIG. 1) for review by a physician or other medical professional. The physician may then prescribe any other appropriate therapies to address the condition. The physician may also adjust the operation of the pacer/ICD to activate, deactivate or otherwise control any therapies that are automatically applied. The bedside monitor may be directly networked with a centralized computing system, such as the HouseCall™ system or the Merlin.Net system of St. Jude Medical, for immediately notifying the physician of any significant increase in LAP. Networking techniques for use with implantable medical systems are set forth, for example, in U.S. Pat. No. 6,249,705 to Snell, entitled "Distributed Network System for Use with Implantable Medical Devices". In addition to CRT, other forms of therapy may also be controlled by the pacer/ICD in response to changes in LAP. In this regard, if the implanted system is equipped with a drug pump, appropriate medications may be automatically administered upon detection of a significant increase in LAP due to heart failure. For example, heart failure medications may be delivered directly to the patient via the drug pump, if warranted. Alternatively, if a drug pump is not available, the patient may be provided with instructions depending on the estimated LAP as to what dosage to take for various heart failure medications. Exemplary heart failure medications include angiotensin-converting enzyme (ACE) inhibitors such as captopril, enalapril, lisinopril and quinapril, diuretics, digitalis, nitrates, and other compounds. Depending upon the particular medication, alternative compounds (e.g., intravenous or subcutaneous agents) may be required for use in connection with an implantable drug pump. Routine experimentation may be employed to identify medications for treatment of heart failure or other conditions that are safe and effective for use in connection with an implantable drug pump. Dosages may be titrated based upon the severity of heart failure as determined from LAP.

Various techniques may be employed to confirm the detection of heart failure (or other medical conditions) made by the pacer/ICD based on the analysis of the impedance signals before drug therapy is delivered. Exemplary heart failure detection/evaluation techniques are set forth in: U.S. Pat. No.

6,748,261, entitled "Implantable medical device for and Method of Monitoring Progression or Regression of Heart Disease by Monitoring Interchamber Conduction Delays"; U.S. Pat. No. 6,741,885, entitled "Implantable Cardiac Device for Managing the Progression of Heart Disease and Method"; U.S. Pat. No. 6,643,548, entitled "Implantable medical device for Monitoring Heart Sounds to Detect Progression and Regression of Heart Disease and Method Thereof"; U.S. Pat. No. 6,572,557, entitled "System and Method for Monitoring Progression of Cardiac Disease State using Physiologic Sensors"; and U.S. Pat. No. 6,480,733, entitled "Method for Monitoring Heart Failure", each assigned to Pacesetter, Inc.

Hence, FIG. 1 provides an overview of an implantable medical system capable of estimating LAP based on impedance signals, delivering any appropriate warning/notification signals, and selectively delivering medications, when warranted. Embodiments may be implemented that do not necessarily perform all of these functions. For example, embodiments may be implemented that estimate LAP but do not automatically initiate or adjust therapy. Moreover, systems provided in accordance with the invention need not include all of the components shown in FIG. 1. In many cases, for example, the system will include only a pacer/ICD and its leads. Implantable warning devices and drug pumps are not necessarily implanted. Some implementations may employ an external monitor for displaying warning signals without any internal warning device. These are just a few exemplary embodiments. No attempt is made herein to describe all possible combinations of components that may be provided in accordance with the general principles of the invention. In addition, note that the particular locations of the implanted components shown in FIG. 1 are merely illustrative and may not necessarily correspond to actual implant locations. Although internal signal transmission lines provided are illustrated in FIG. 1 for interconnecting the various implanted components, wireless signal transmission may alternatively be employed.

Overview of LAP Estimation Based on Electrical Impedance

Figure 2:
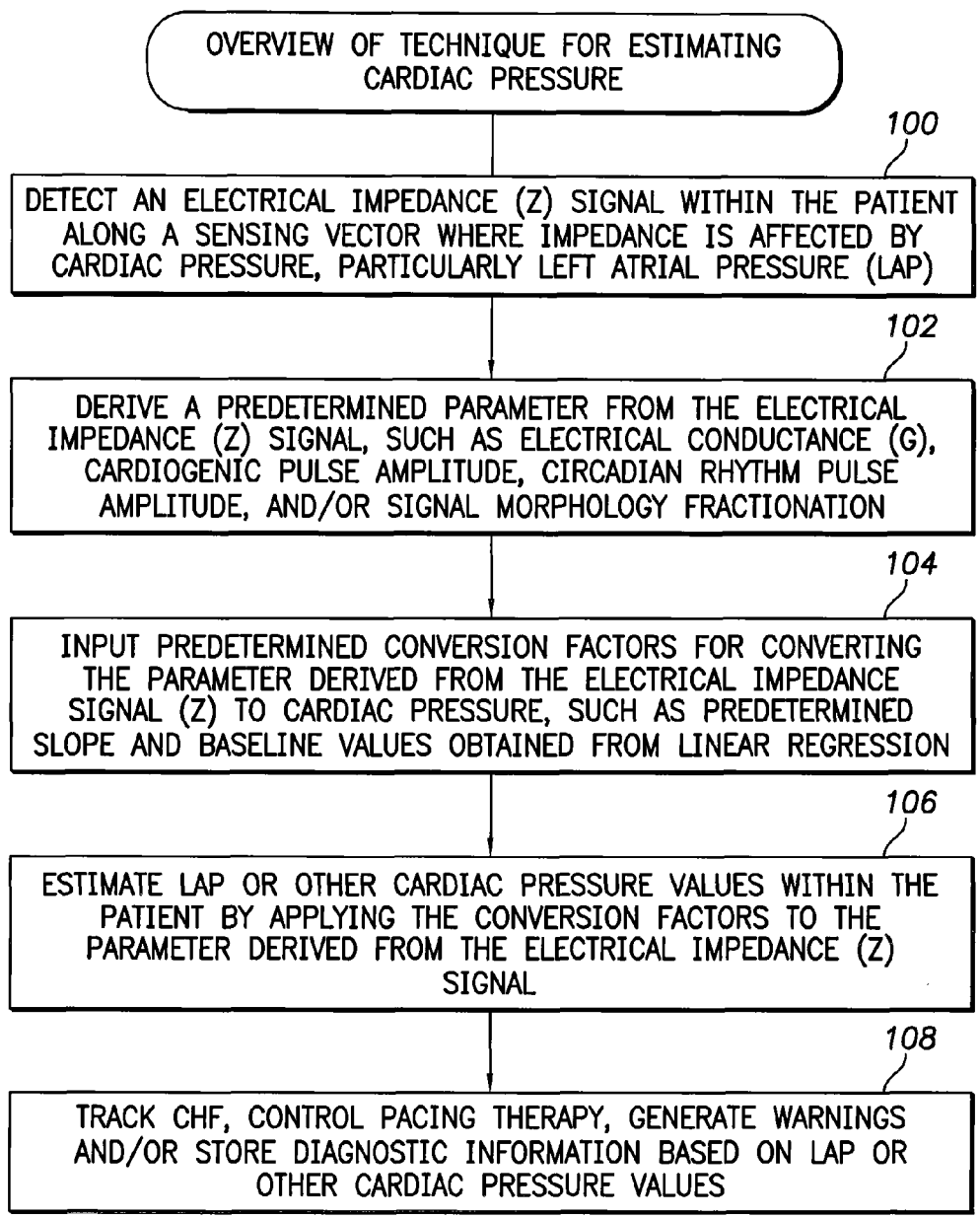
FIG. 2 is a flow diagram providing an overview of LAP estimation techniques that may be performed by the system of FIG. 1.

FIG. 2 provides an overview of the LAP estimation techniques that may be performed by the pacer/ICD of FIG. 1 or other implantable device. Broadly, at steps 100 and 102, a predetermined impedance-based parameter is measured within patient tissues, wherein the parameter is affected by cardiac pressure. At steps 104 and 106, cardiac pressure is then estimated within the patient by applying predetermined conversion factors to the impedance-based parameter. Alternatively, conductance (G) or other suitable electrical parameters can instead be detected. Considering the impedance-based example in more detail, at step 100, the pacer/ICD detects electrical impedance (Z) along a sensing vector where impedance is affected by cardiac pressure, particularly LAP. For example, the cardiogenic impedance signal may be sensed between an LV tip electrode and an RA tip electrode such that the sensing vector passes through the left atrium. However, impedance signals sensed between other electrode pairs, such as the LV lead and the device can, may alternatively be utilized to indirectly estimate LAP under the presumption that, if these electrode pairs span the region containing the blood within pulmonary veins, then a resulting estimate of pulmonary venous pressure may be used as an estimate for LAP.

Impedance signals are obtained by transmitting a current between a pair of electrodes, and subsequently, measuring the voltage between the same or another pair of electrodes. The impedance is calculated as the ratio of the measured voltage to the transmitted current. Preferably, a tri-phasic impedance pulse waveform is employed to sense the impedance signal. The tri-phasic waveform is a frequency-rich, low energy waveform that provides a net-zero charge and a net-zero voltage. An exemplary tri-phasic pulse waveform is described in detail in the related patent applications, cited above. Depending upon the particular sensing vector, it may be appropriate to filter the impedance signal to eliminate or reduce any non-cardiogenic components such as any components arising due to respiration or changes in body position of posture. Bandpass filtering is typically sufficient to filter out respiratory components.

Although the examples described herein are primarily directed to estimating LAP, other cardiac pressure values may alternatively be estimated, such as LVP, by using impedance signals detected using appropriate sensing vectors (e.g., LV-tip electrode to RV-ring electrode or RV-Shock coil). Indeed, multiple impedance signals may be sensed using different sensing vectors passing through different chambers of the heart so as to permit the pacer/ICD to estimate cardiac pressure within different chambers of the heart, assuming appropriate conversion values have been determined and calibrated. To this end, the implanted system may be equipped, e.g., with multiple electrodes per lead or with multiple leads per chamber. Unipolar or bipolar sensing systems may be employed.

Depending upon the implementation, particular components of an initial raw impedance signal ($Z_0$) detected by the pacer/ICD are exploited, such as the high-frequency cardiogenic impedance signal ($Z_C$) representative of the beating of the heart of the patient, the low-frequency respiratory impedance signal ($Z_R$) representative of the respiration of the patient, or the ultra-low frequency circadian impedance signal representative of daily variations in the raw impedance signal ($Z_0$) or the low-frequency respiratory impedance signal ($Z_R$). Note that current state-of-the art pacer/ICDs do not typically include a detection circuit specifically for detecting circadian impedance variations. There is a cardiogenic detection circuit that extracts the cardiogenic component ($Z_C$) of the impedance signal (also referred to as cardiogenic impedance (CI)) from the raw impedance signal ($Z_0$) by substantially filtering out non-cardiogenic components. There is a low frequency detection circuit that extracts the respiratory component ($Z_R$) of the impedance signal (also referred to as respiratory impedance (RI)) by substantially filtering out non-respiratory components. Circadian variations may be detected by storing the raw impedance values over a 24-hour period then processing the recorded raw values to extract circadian variations. In the predecessor applications cited above, the term "low-frequency raw impedance signal" was used to refer to the respiratory impedance signal ($Z_R$). Techniques for detecting or extracting the various components of the initial raw impedance signal are discussed in the cited applications.

At step 102, the pacer/ICD derives one or more predetermined parameters from the detected electrical impedance signals, such as electrical conductance (G), cardiogenic pulse amplitude, circadian rhythm pulse amplitude, or signal morphology fractionation parameters. Examples involving each are discussed below. At step 104, the pacer/ICD inputs predetermined conversion factors from memory for converting the parameter(s) derived from the electrical impedance signal to LAP (or other cardiac pressure values). The conversion factors may be, e.g., predetermined slope and baseline values obtained during a calibration procedure employing linear regression. Different conversion factors are typically required depending upon the particular parameters derived from the electrical impedance signal. That is, different slope and baseline values are used for a conductance-based estimation than for a cardiogenic pulse amplitude-based estimation. In some implementations, the pacer/ICD is equipped to perform only one estimation technique, such as conductance-based estimation, and so the only conversion values stored in memory are conductance-based conversion factors. In other implementations, the pacer/ICD is equipped to perform any or all of the estimation techniques described herein and so the memory of the pacer/ICD stores all of the different conversion factors and retrieves the appropriate factors depending upon the particular estimation technique currently being used, as specified by the programming of the device. LAP values estimated using different techniques may be averaged together.

At step 106, the pacer/ICD then estimates LAP or other cardiac pressure values within the patient by applying the conversion factors retrieved from memory (as step 104) to the parameter(s) derived from the electrical impedance signal (as step 104). When using slope and baseline conversion factors, cardiac pressure may be generally estimated using:

Cardiac Pressure=Derived_Parameter*Slope+Baseline where Derived_Parameter represents the parameter derived from the impedance signal, i.e. conductance, cardiogenic pulse amplitude, etc., and Slope and Baseline represent the conversion factors appropriate for use with the particular derived parameter. This formula assumes a linear relationship between cardiac pressure and the derived parameters, which is an appropriate presumption based on the particular parameters discussed herein, at least insofar as estimating LAP is concerned. Routine experimentation may be performed to determine whether a linear relationship is also suitable for use in estimating other particular cardiac pressure values, such as LVP, or is also suitable for use with other parameters that might be derived from the electrical impedance signal besides those specifically mentioned herein. Moreover, it should be understood that linear models need not necessarily be used, i.e. more sophisticated correlation models may instead by employed. Linear models are preferred in view of their simplicity.

At step 108, the pacer/ICD tracks CHF, controls pacing therapy (such as CRT), generates warnings and/or stores diagnostic information based on estimated LAP values or other estimated cardiac pressure values. As already explained, the warnings and/or diagnostic data can be forwarded to a physician for review. Preferably, the diagnostic data includes the estimated LAP values for physician review. This is particularly advantageous since physicians are typically more comfortable reviewing LAP information than raw impedance values. Steps 100-108 may be repeated in a loop so as to update the estimated LAP. Depending upon the particular parameter used to estimate LAP, the estimates may be performed substantially in real-time so as to permit the pacer/ICD to continuously, or at least very frequently, calculate new LAP values. That is, in some implementations, a real-time LAP(t) function may be estimated so as to allow the pacer/ICD to track beat-to-beat changes in LAP. In particular, estimates of LAP based on conductance, on cardiogenic pulse amplitudes, or cardiogenic fractionation may potentially be performed substantially in real-time, assuming the pacer/ICD is appropriately configured. This allows the pacer/ICD to respond promptly to changes within the heart of the patient. Estimates of LAP based on circadian pulse amplitudes are usually not performed in real-time. Rather, these parameters are tracked over extended periods of time (e.g. days, weeks or months) so as to track longer-term changes in the heart of the patient.

Turning now to FIGS. 3-16, various illustrative embodiments will be described in greater detail.
Exemplary LAP Estimation Techniques Referring next to FIG. 3, a conductance-based LAP detection example is illustrated. At step 200, the pacer/ICD detects electrical impedance (Z) along a sensing vector through the left atrium and, at step 202, derives conductance (G) from impedance (Z) by calculating 1/Z, i.e. by taking the reciprocal of the impedance. Preferably, the raw impedance signal ($Z_O$) is used to derive conductance, though other impedance signals could instead be used. Alternatively, conductance may be measured directly within the patient without necessarily first detecting impedance. In any case, at step 204, the pacer/ICD inputs the particular slope and baseline values ($Slope_G$+$Baseline_G$) for converting conductance to LAP. These are predetermined conversion values that the pacer/ICD retrieves from memory. Calibration techniques for initially deriving the conversion values will be discussed below with reference to FIGS. 4-10. At step 206, the pacer/ICD estimates LAP by applying the slope and baseline values (input at step 204) to the conductance value (derived at step 202):

$eLAP=G*Slope_G+Baseline_G$

As indicated by step 208, the pacer/ICD can repeat steps 200-206 frequently so as to track a time-varying LAP function, i.e. LAP(t).

A variety of techniques may be used to initially determine and subsequently adjust the conversion values ($Slope_G$+$Baseline_G$), i.e. to calibrate the conductance-based estimation technique of FIG. 3. FIG. 4 summarizes a technique wherein calibration is performed based on calibration values obtained within the particular patient in which the pacer/ICD is implanted. That is, the conversion values are optimized for use with the particular patient. The procedure of FIG. 4 is performed by a physician during the implant procedure of the pacer/ICD while venous access is readily available and a Swan-Ganz catheter can be easily inserted. The procedure in FIG. 4 may be repeated or performed alternatively at a follow-up session sometime after implantation of the pacer/ICD following the acute post-implant phase during which the implanted leads undergo healing process that is known to affect the measured impedance signals. At step 210, an external calibration system (such as the external programmer of FIG. 21) detects or inputs a first conductance calibration value ($G_1$) and a corresponding first LAP calibration value ($LAP_1$) measured while the patient is at rest. Preferably, the conductance value is detected by the pacer/ICD itself using its leads and its internal detection circuitry, then transmitted to the external system. Simultaneously, $LAP_1$ is detected using, e.g., a Swan-Ganz catheter to measure PCWP. The LAP value is also relayed to the external programmer.

At step 212, detects or input a second conductance calibration value ($G_2$) and a corresponding second LAP calibration value ($LAP_2$) measured at a time when the patient is subject to a condition significantly affecting LAP so that $LAP_2$ differs substantially from $LAP_1$. For example, the physician may have the patient perform isometric muscle contractions, particular using thoracic muscles, so as to change LAP within the patient. Alternatively, the physician may administer vasodilatation or vasoconstriction medications, so as to change LAP, or may temporarily reprogram the pacer/ICD to perform rapid pacing, which also changes LAP. Still further, the physician may have the patient perform the Valsalva maneuver, which reduces effective LAP secondary to reduced venous return. The Valsalva maneuver occurs when a patient forcibly exhales for about 15 seconds against a fixed resistance with a closed glottis while contracting the abdominal muscles. A sudden transient increase in intra-thoracic and intra-abdominal pressures occurs, which tends to empty the chambers of the heart of blood by preventing any further filling, such that within 1 to 2 seconds (phase I of the Valsalva maneuver) the effective right atrial and right ventricular pressures drop to zero, while following 5 seconds (Late phase II) the effective left atrial and left ventricular pressures tend to reach zero. Again, the conductance value is detected by the pacer/ICD itself then transmitted to the external system. $LAP_2$ is simultaneously detected using the Swan-Ganz catheter. Thus, after step 212, the external system has obtained at least two pairs of calibration values ($LAP_1$, $G_1$ and $LAP_2$, $G_2$) where the LAP values differ substantially from one another. Since conductance through the left atrium varies due to changes in left atrial blood volume that correspond to changes in the LAP, the conductance values likewise differ from one another, permitting reliable calculation of the slope and baseline values.

At step 214, the external system calculates $Slope_G$ using:

$$Slope_G = (LAP_2 - LAP_1)/(G_2 - G_1).$$

At step 216, the external system calculates $Baseline_G$ (also referred to herein as $bLAP_G$) using:

$$Baseline_G = LAP_1 - Slope_G * G_1.$$

Figure 3:
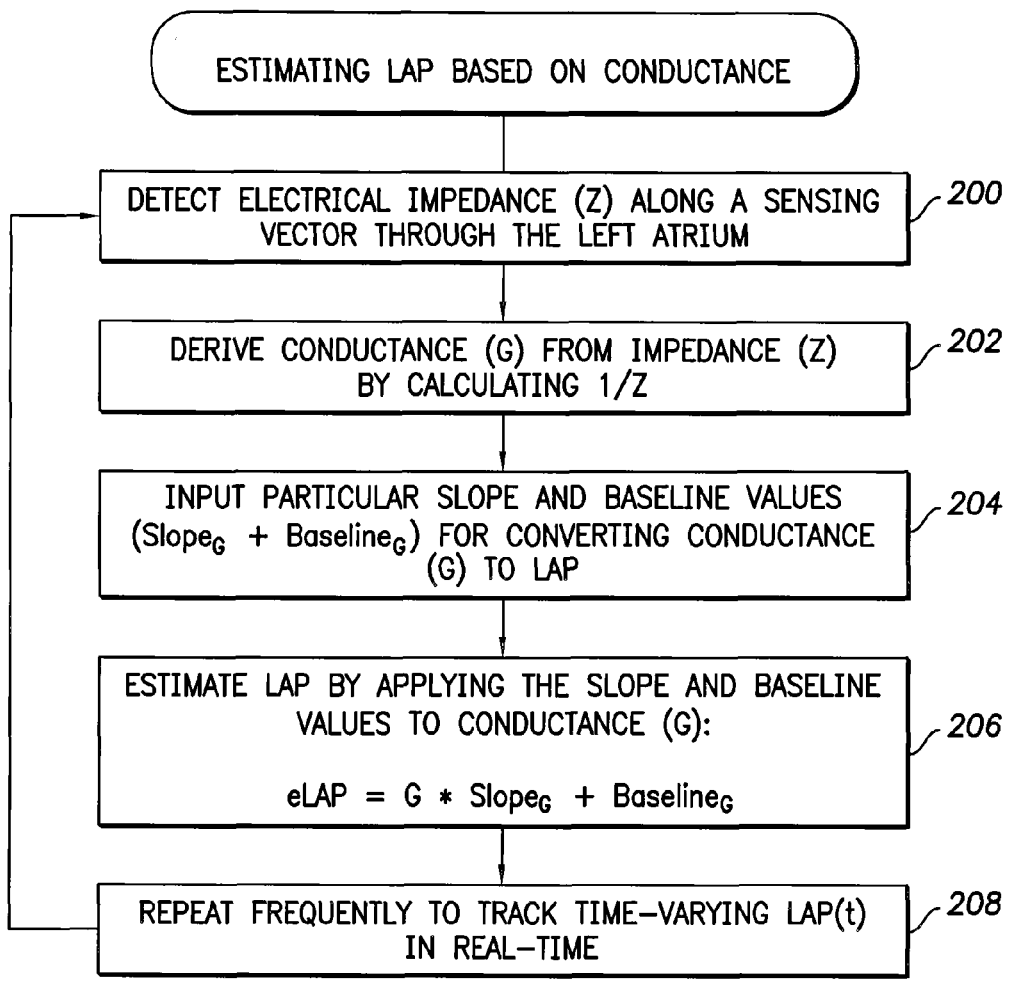
FIG. 3 is a flow diagram summarizing a first illustrative technique wherein LAP is estimated based on electrical conductance, and which may be performed in accordance with the general technique of FIG. 2.
Figure 4:
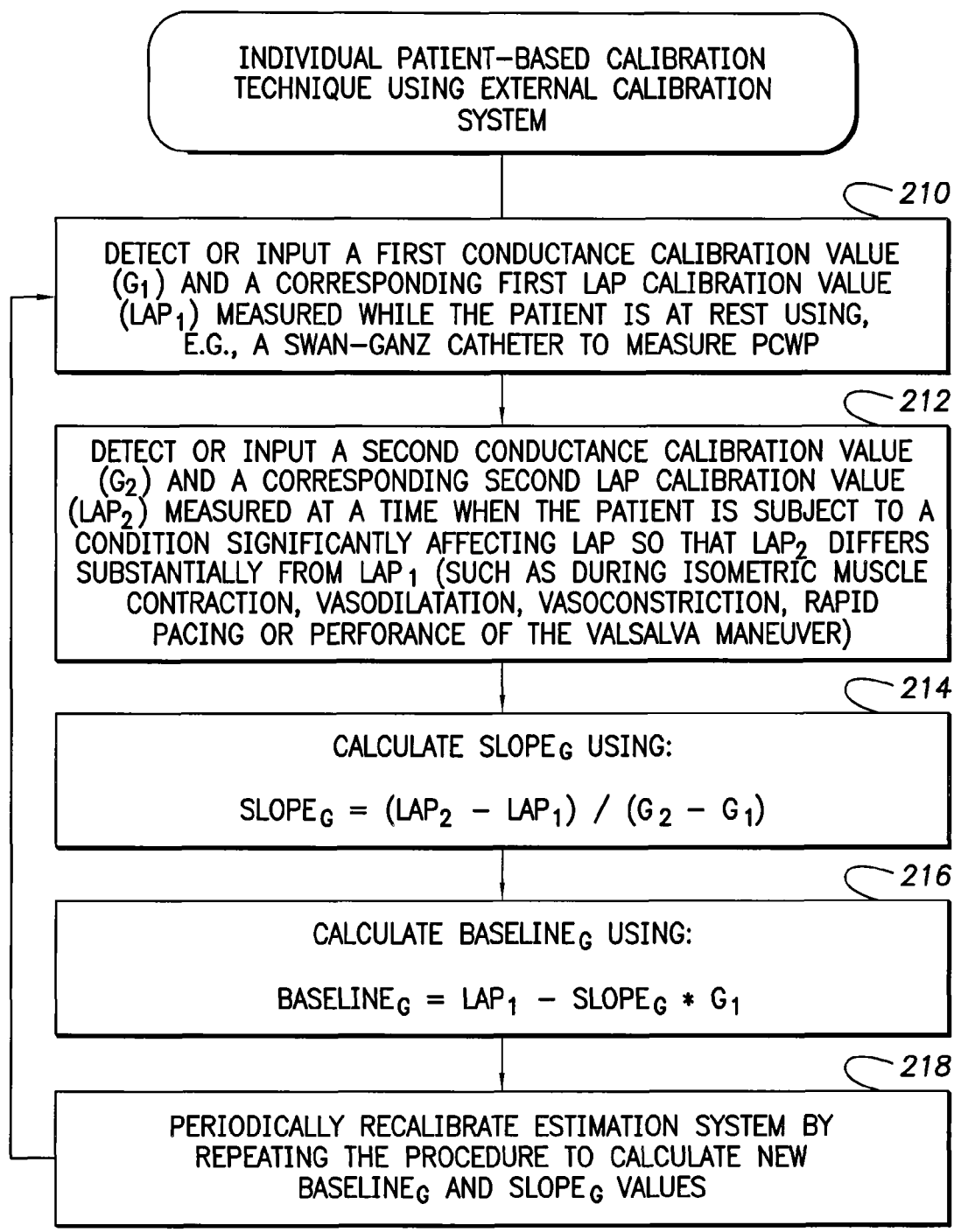
FIG. 4 is a flow diagram illustrating an exemplary procedure for calibrating the LAP-based technique of FIG. 3 using calibration parameters obtained within the patient in which the system is implanted.

These values are then transmitted to the pacer/ICD for storage therein for use in estimating LAP based on newly detected values of impedance using the technique of FIG. 3. Preferably, LAP values provided by the pacer/ICD are compared with LAP values detected using the Swan—Ganz catheter to verify that the estimation system of the pacer/ICD has been properly calibrated.

More generally, the first and second impedance-derived calibration values are also referred to herein as $C_1$ and $C_2$. The external system calculates Slope using:

$$Slope = (LAP_2 - LAP_1)/(C_2 - C_1).$$

The external system calculates Baseline using:

$$Baseline = LAP_1 - Slope * C_1.$$

As will become apparent, the impedance-derived calibration values need not be conductance values, but can be other values derived from impedance, such as cardiogenic pulse amplitude values.

Figure 5:
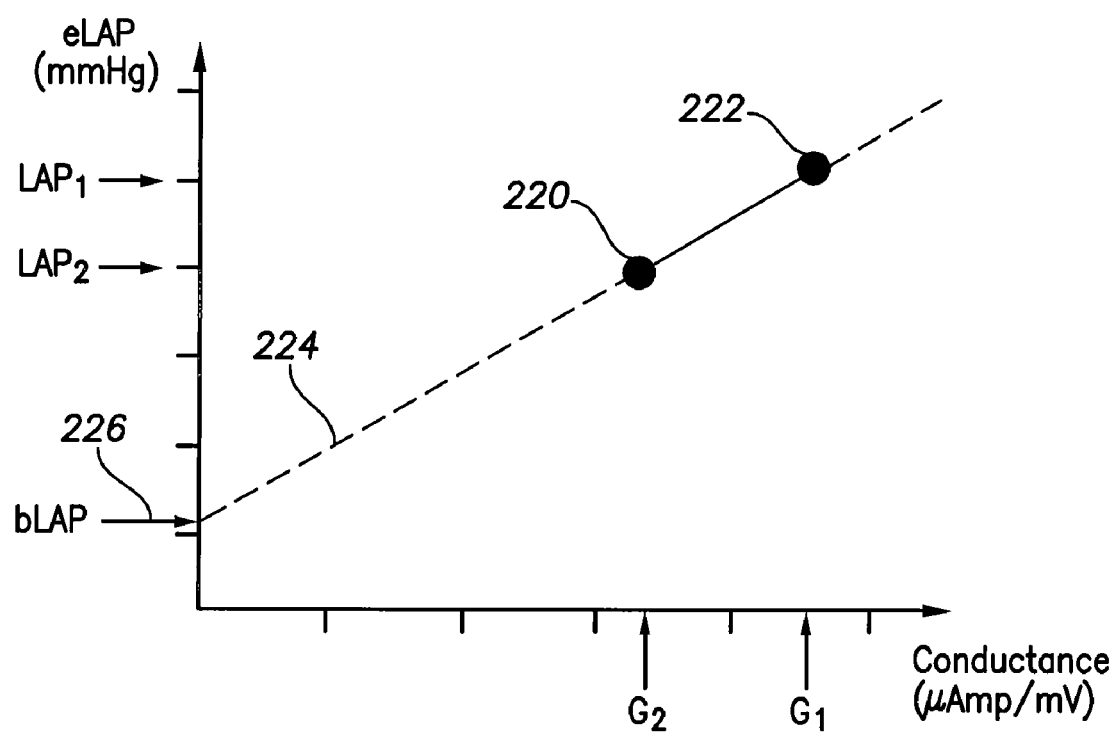
FIG. 5 is a graph illustrating a linear relationship between electrical conductance and LAP calibration parameters exploited by the calibration technique of FIG. 4.

FIG. 5 illustrates an exemplary pair of calibration values 220, 222, along with exemplary slope 224 and baseline (bLAP) values 226 derived therefrom using the technique of FIG. 4. Although only two pairs of calibration values are used in the example of FIG. 4, it should be understood that additional pairs of calibration values may be obtained. Linear regression techniques may be used to derive slope and baseline values from a plurality of pairs of calibration values. Also, as indicated by step 218, the recalibration procedure of FIG. 4 can be repeated periodically (such as during subsequent follow-up sessions with the patient) to update both the slope and baselines values to respond to changes, if any, that may arise within the patient, perhaps due to scarring near the sensing electrodes, which might affect the conductance values. Alternatively, a re-calibration technique may be performed by the pacer/ICD itself that re-calibrates only the baseline value. This is summarized in FIG. 6.

Figure 6:
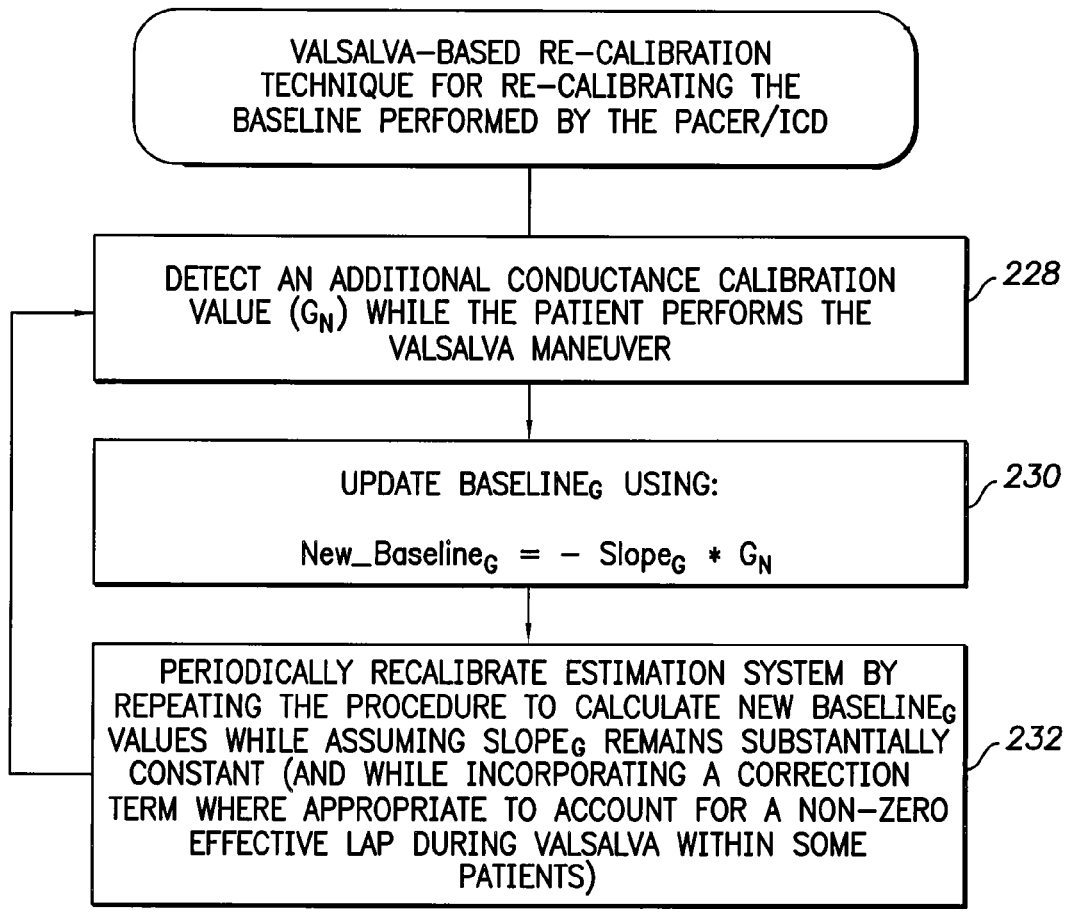
FIG. 6 is a flow diagram illustrating an exemplary procedure for re-calibrating the baseline value of the LAP-based technique of FIG. 3 using additional calibration parameters obtained within the patient in which the system is implanted.

FIG. 6 summarizes a recalibration procedure performed by the pacer/ICD to re-calibrate the baseline value. The procedure exploits the assumption that the slope value, once calculated for a particular patient, typically does not change significantly within the patient. This allows the baseline value to be re-calibrated independently of the slope value. At step 228, the pacer/ICD detects an additional conductance calibration value ($G_N$) while the patient performs the Valsalva maneuver. As already explained, during the Valsalva maneuver effective LAP drops to zero or near zero. Hence, a separate measurement of effective LAP is not required. Under the assumption that effective LAP drops to zero at the time when the additional conductance value ($G_N$) is measured, the baseline value can be re-calculated, at step 230, based on the previous slope and the new conductance value ($G_N$) using:

$$New\_Baseline_G = -Slope_G * G_N.$$

A particularly attractive feature of this recalibration procedure is that it is non-invasive and can be performed in the ambulatory setting in the physician's office during a routine follow-up visit. As already noted, if the lungs are "dry" and there is only a change in pulmonary venous volume with emptying during Valsalva, conductance should fall to a new zero baseline value as well. If there is extravascular pulmonary fluid accumulation, and the impedance vector primarily passes through the lung, impedance may not change substantially during Valsalva because overall interstitial lung fluid does not change substantially, only by the fraction of intravascular blood emptying from the pulmonary veins. Preferably, re-calibration is performed while the patient is clinically stable and the lungs are "dry". Also, by using an impedance vector passing through the left atrium, the affect of any interstitial pulmonary fluids on the detected impendence/conductance values is reduced. Still further, within at least some patients, even when using an impedance vector passing through a cardiac chamber, changes in impedance during Valsalva may be somewhat unpredictable because of changing intra-electrode distances and changing fluid volumes. Accordingly, in at least some patients, Valsalva-based re-calibration techniques may not achieve precise re-calibration due to these factors. Within those patients, other re-calibration techniques are preferably used, which do not necessarily exploit Valsalva. Alternatively the patient may be instructed to take a large dose of diuretics prior to performing the calibration procedure so that a "dry" state of the lung may be artificially created.

In some patients with diastolic heart failure and poor left ventricular compliance who may have higher cardiac filling pressures (PCWP>20 mmHg) even when well compensated, the effective LAP may not drop completely to zero during a Valsalva maneuver and a correction term may need to be applied to account for this possibility. (See, for example, FIG. 5 of the Eigler, et al. patent application, cited above.) In order to determine whether a particular patient requires such a correction term a third measurement of the conductance ($G_3$) during the original calibration procedure FIG. 4 should be obtained while the patient is performing the Valsalva maneuver. This assumes that $G_1$ and $G_2$ when obtained not during a Valsalva maneuver. The correction term ($eLAP_{VALSALVA}$) is simply computed using:

$$eLAP_{VALSALVA} = G_3 * Slope_G + Baseline_G$$

wherein $eLAP_{VALSALVA}$ is an effective LAP pressure value. Ideally, if the blood volume inside the left atrium significantly decreases during the Valsalva maneuver, then $eLAP_{VALSALVA}$ will be near zero. Step 230 may alternatively be computed using:

$$New\_Baseline_G = eLAP_{VALSALVA} - Slope_G * G_N.$$

The response of intracardiac pressures to the Valsalva is discussed in McClean et al., "Noninvasive calibration of cardiac pressure transducers in patients with heart failure: An aid to implantable hemodynamic monitoring and therapeutic guidance", Journal of Cardiac Failure, Vol. 12 No. 7 2006, pp 568-576. It is described therein that during the Valsalva maneuver the effective PCWP reduces nearly to zero as described above. A similar observation was observed for other chambers of the heart. In particular, the effective residual pressure within a specific cardiac chamber ($P_{eff}$) was computed as the difference between the measured intracardiac pressure ($P_{intracardiac}$) and the simultaneous intrathoracic or airway pressure ($P_{airway}$) averaged over the time interval from 5 to 10 seconds after the initiation of the Valsalva maneuver (Late phase II). The effective intracardiac pressure ($P_{eff}$) is computed using:

$$P_{eff} = P_{intracardiac} - P_{airway}$$

where ($P_{airway}$) is detected, e.g., using an external pressure detection system. See, for example, the upper airway apparatus of FIG. 2 of U.S. Patent Application 2004/0019285 of Eigler, et al., entitled "Apparatus for Minimally Invasive Calibration of Implanted Pressure Transducers", which is incorporated by reference herein in its entirety. Thus, in order to estimate the effective LAP ($LAP_{eff}$) during the Valsalva maneuver one may obtain this measurement directly by computing average of the difference between the PCWP and the simultaneous airway pressure over the interval from 5 to 10 seconds following the initiation of the Valsalva maneuver (late Phase II). This may be written more specifically as:

$$LAP_{eff} = PCWP - P_{airway}$$

and $LAP_{eff}$ may be used alternatively as the correction term described above.

The new baseline value is then used when converting additional conductance values to effective eLAP values (step 206 of FIG. 3.) As indicated by step 232, the pacer/ICD can periodically recalibrate its estimation system by repeating the procedure to calculate new $Baseline_G$ values while assuming $Slope_G$ remains substantially constant and using the correction term where appropriate.

In practice, the procedure of FIG. 6 may be initiated by periodically having the pacer/ICD transmit a signal to the bedside monitor providing instructions to the patient to perform the Valsalva maneuver. The pacer/ICD detects the new conductance value during the Valsalva maneuver and updates the baseline value. The pacer/ICD may be additionally programmed to verify that the patient actually performed the Valsalva maneuver by, e.g., analyzing changes in respiration (as detected using otherwise conventional respiration detection techniques) to verify that respiratory patterns consistent with the Valsalva maneuver occur. The pacer/ICD can also time its detection of the additional conductance value based on the respiratory signals to help ensure that the new conductance value is measured at a point when effective LAP is expected to be zero. Alternatively, the re-calibration technique may be performed only under the supervision of a physician or other clinician during a follow-up session with the patient. Still, the re-calibration procedure eliminates the need to directly measure effective LAP during the follow-up using a Swan-Ganz catheter. The catheter is only employed during the original calibration procedure. Thus, FIG. 6 illustrates a technique wherein the baseline value is re-calibrated by the pacer/ICD under the assumption that slope does not change by exploiting the Valsalva maneuver. The Valsalva maneuver may also be exploited to re-calibrate both slope and baseline, if needed within a particular patient. This is illustrated in FIGS. 7 and 8.

Figure 7:
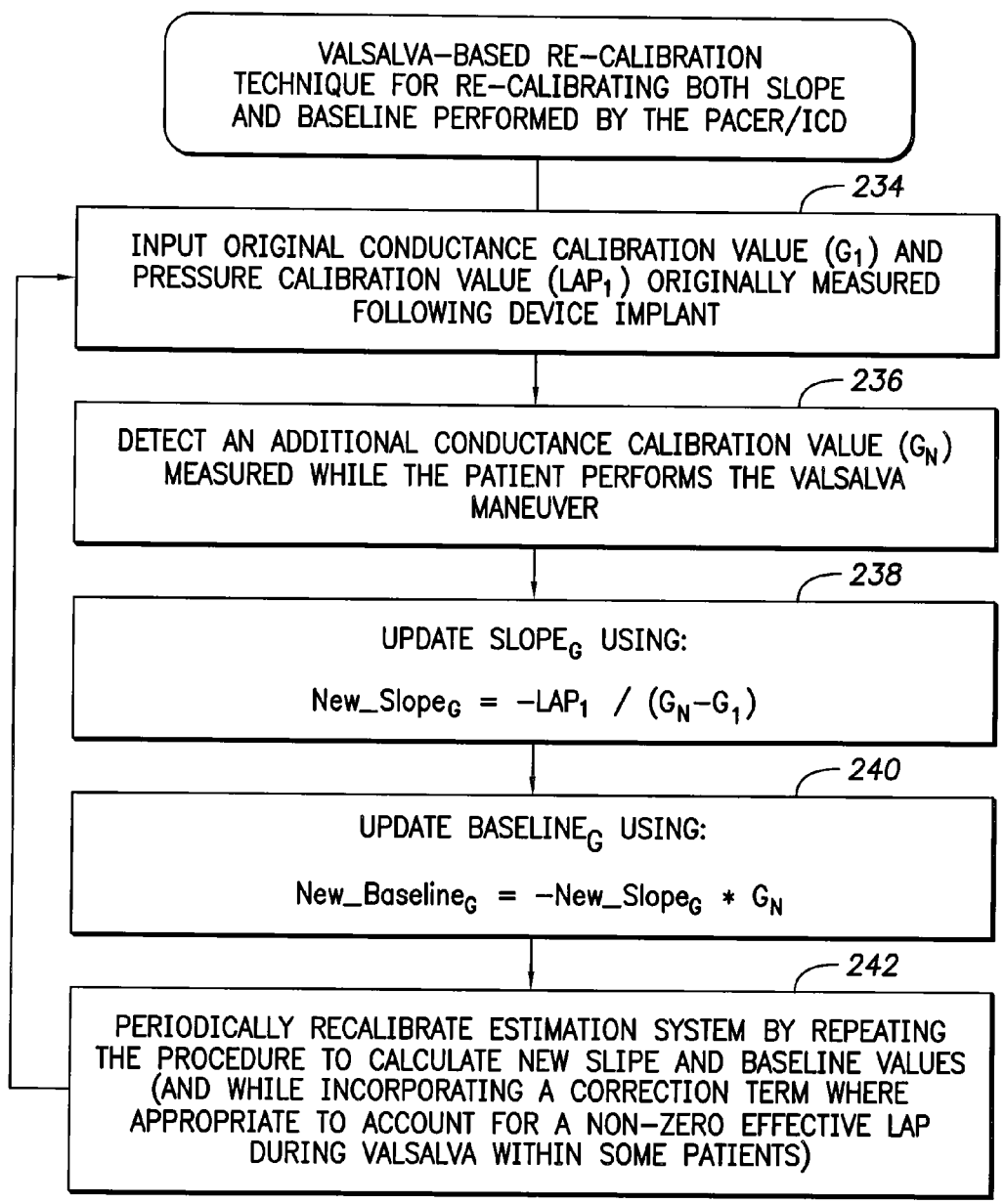
FIG. 7 is a flow diagram illustrating an exemplary procedure for re-calibrating both slope and baseline values of the LAP-based technique of FIG. 3 using additional calibration parameters obtained within the patient in which the system is implanted.
Figure 8:
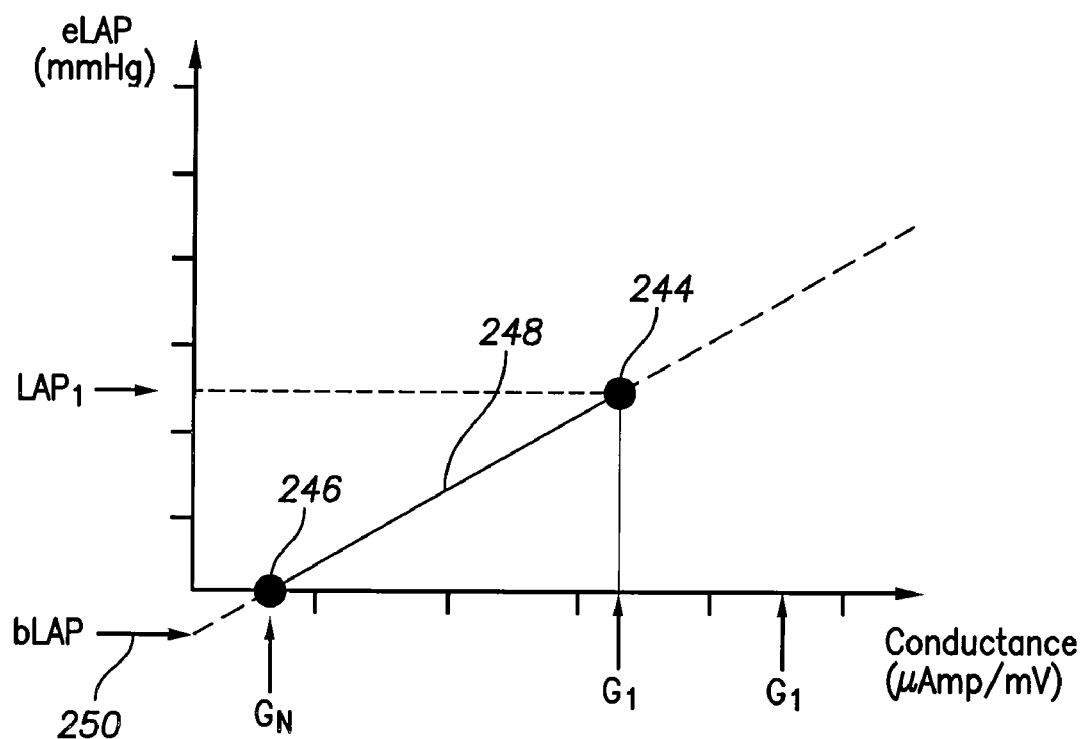
FIG. 8 is a graph illustrating a linear relationship between electrical conductance and LAP calibration parameters exploited by the re-calibration technique of FIG. 7 and, in particular, illustrating a zero LAP value obtained within the patient during the Valsalva maneuver.

FIG. 7 summarizes a recalibration procedure performed by the pacer/ICD to re-calibrate both the slope and baseline values. The procedure can be used in patients where the slope value changes. At step 234, the pacer/ICD inputs the original conductance calibration value ($G_1$) and effective pressure calibration value ($LAP_1$) originally measured following device implant (FIG. 4) or during a previous calibration procedure. At step 236, the pacer/ICD detects an additional conductance calibration value ($G_N$) while the patient performs the Valsalva maneuver. As already noted, during the Valsalva maneuver effective LAP typically drops to at or near zero and so separate measurement of effective LAP is not required. Rather, it is assumed that effective LAP is zero when the additional conductance value ($G_N$) is measured, thus allowing the slope to be re-calculated, at step 238, using:

$$\text{New\_Slope}_G = -LAP_1/(G_N - G_1).$$

Once the new slope value is calculated, the new baseline value can be calculated, at step 240, using:

$$\text{New\_Baseline}_G = -\text{New\_Slope}_G * G_N.$$

The new slope and baseline values are then used when converting additional conductance values to effective eLAP values (step 206 of FIG. 3.) As indicated by step 242, the pacer/ICD can periodically recalibrate its estimation system by repeating the procedure to calculate new $Baseline_G$ and $Slope_G$ values and using the correction term where appropriate. As with the procedure of FIG. 6, the procedure of FIG. 7 may be initiated by periodically having the pacer/ICD transmit a signal to the bedside monitor providing instructions to the patient to perform the Valsalva maneuver or the procedure may be performed under the supervision of a physician or other clinician.

FIG. 8 illustrates an exemplary pair of calibration values 244, 246, along with exemplary slope 248 and baseline (bLAP) values 250 derived therefrom using the technique of FIG. 7. The first pair of calibration values 244 is obtained following implant. The second pair of calibration values 246 is obtained during the re-calibration procedure while the patient performs the Valsalva maneuver. Since the Valsalva maneuver is being performed, the effective LAP value of the second pair of calibration values 246 is zero and so the pressure need not be measured. The conductance value of the second pair along with the pressure and conductance values of the first pair are used to calculate the new slope 244 and baseline (bLAP) values 250 using the equations of FIG. 7.

Figure 9:
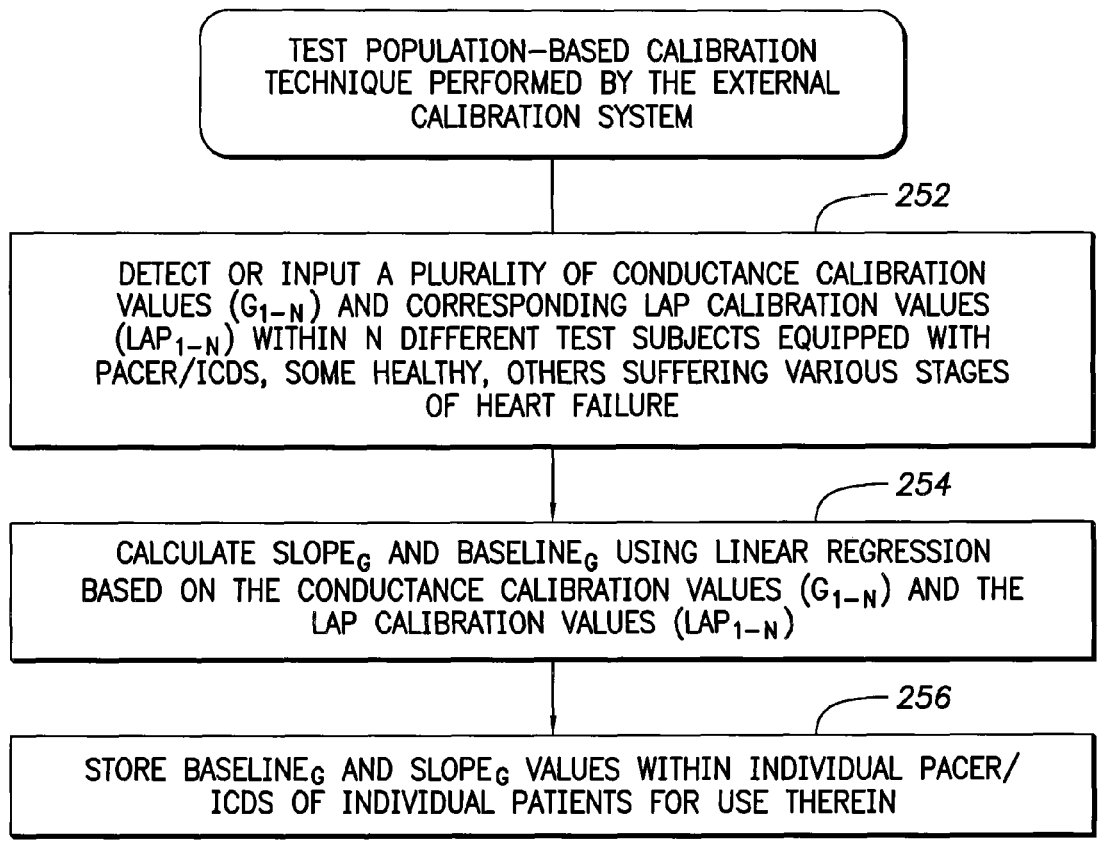
FIG. 9 is a flow diagram illustrating an exemplary procedure for calibrating the LAP-based technique of FIG. 3 using calibration parameters obtained from a population of test subjects.
Figure 10:
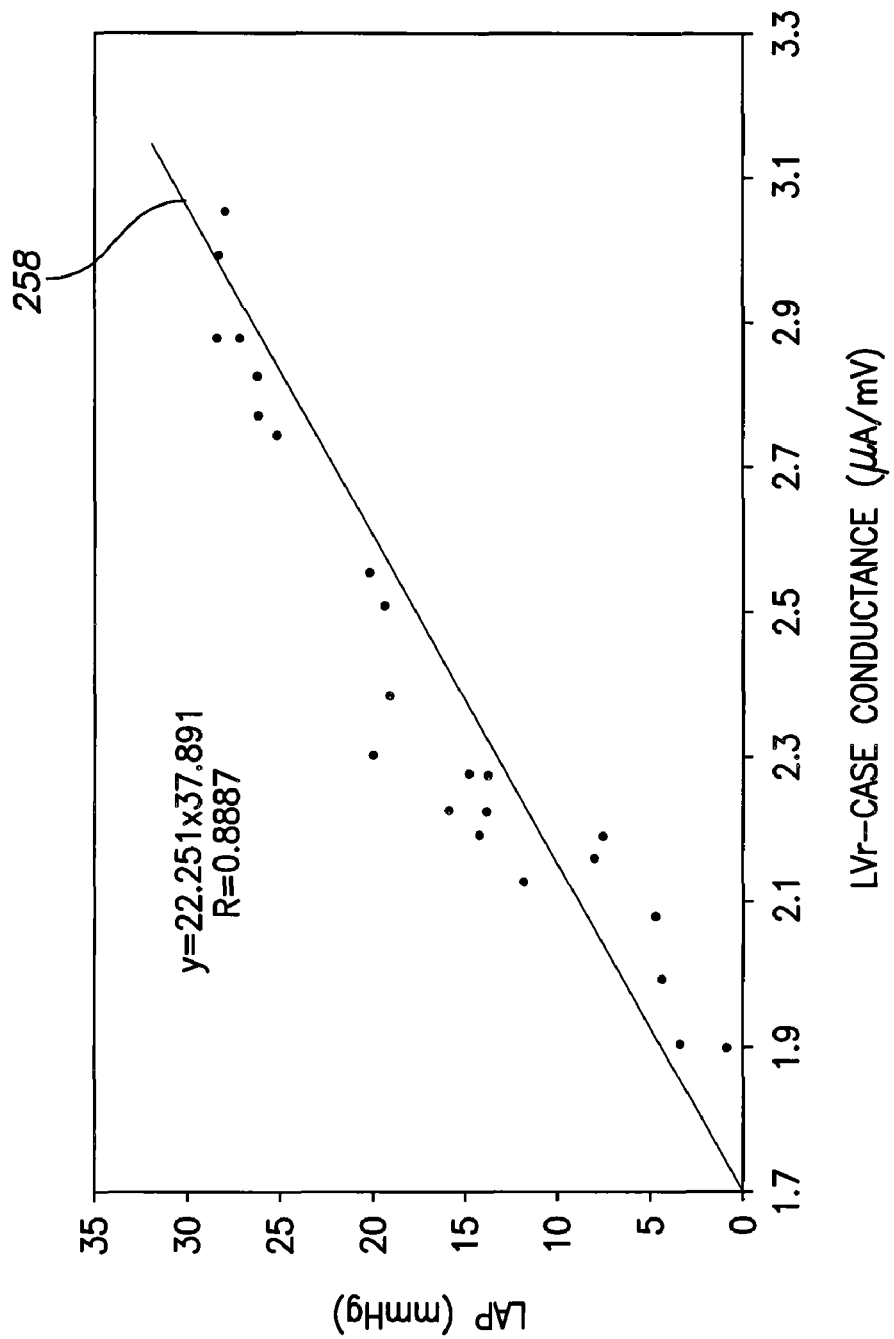
FIG. 10 is a graph illustrating a linear correlation between LAP and electrical conductance that may be exploited by the calibration procedures of FIG. 9.

Turning now to FIGS. 9 and 10, linear regression techniques for calibrating or re-calibrating the conductance-based estimation procedure will be summarized. These techniques exploit a plurality of values for determining the slope and baseline values. In the specific example of FIG. 9, data is obtained from a plurality of test patients subject to various stages of heart failure and have various LAP values. Beginning at step 252, the external calibration system detects or inputs a plurality of conductance calibration values ($G_{1-N}$) and corresponding LAP calibration values ($LAP_{1-N}$) within N different test subjects equipped with pacer/ICDs, some healthy, others suffering differing stages of heart failure, i.e. differing levels of severity of heart failure. The conductance values are detected by the pacer/ICDs of the test subjects, then relayed to the external calibration system. The LAP values may be obtained using Swan—Ganz catheters or the like. Since the test subjects exhibit differing stages of heart failure, differing values of LAP are thereby exhibited. At step 254, the external system then calculates $Slope_G$ and $Baseline_G$ values using linear regression based on the conductance calibration values ($G_{1-N}$) and the LAP calibration values ($LAP_{1-N}$). At step 256, the external system then stores the $Slope_G$ and $Baseline_G$ values within individual pacer/ICDs of individual patients for use therein. By obtaining data from a population of test subjects, the slope and baseline values are therefore likely to be effective within a wide range of patients. In some patients, these values may be sufficient to provide an adequate estimate of LAP. In other patients, these values may be used as starting points for further re-calibration. For example, the slope value obtained via the technique of FIG. 9 may be used within a wide range of patients along with patient-specific baseline values obtained using the baseline-only re-calibration procedure of FIG. 6.

FIG. 10 illustrates a range of LAP and conductance values from which a slope value 258 is obtained via linear regression. The actual data of FIG. 10 was obtained from a single (animal) test subject in which heart failure was induced via a rapid pacing protocol. However, a similar distribution of LAP and conductance values is exhibited within human patients as well, when heart failure occurs naturally.

Thus, FIGS. 3-10 illustrate various conductance-based LAP estimation techniques. Turning now to FIGS. 11-16, various alternative embodiments will be described wherein parameters other than conductance are exploited. Some of the steps of these alternative procedures are similar to steps already described and hence will be described again in detail.

Figure 11:
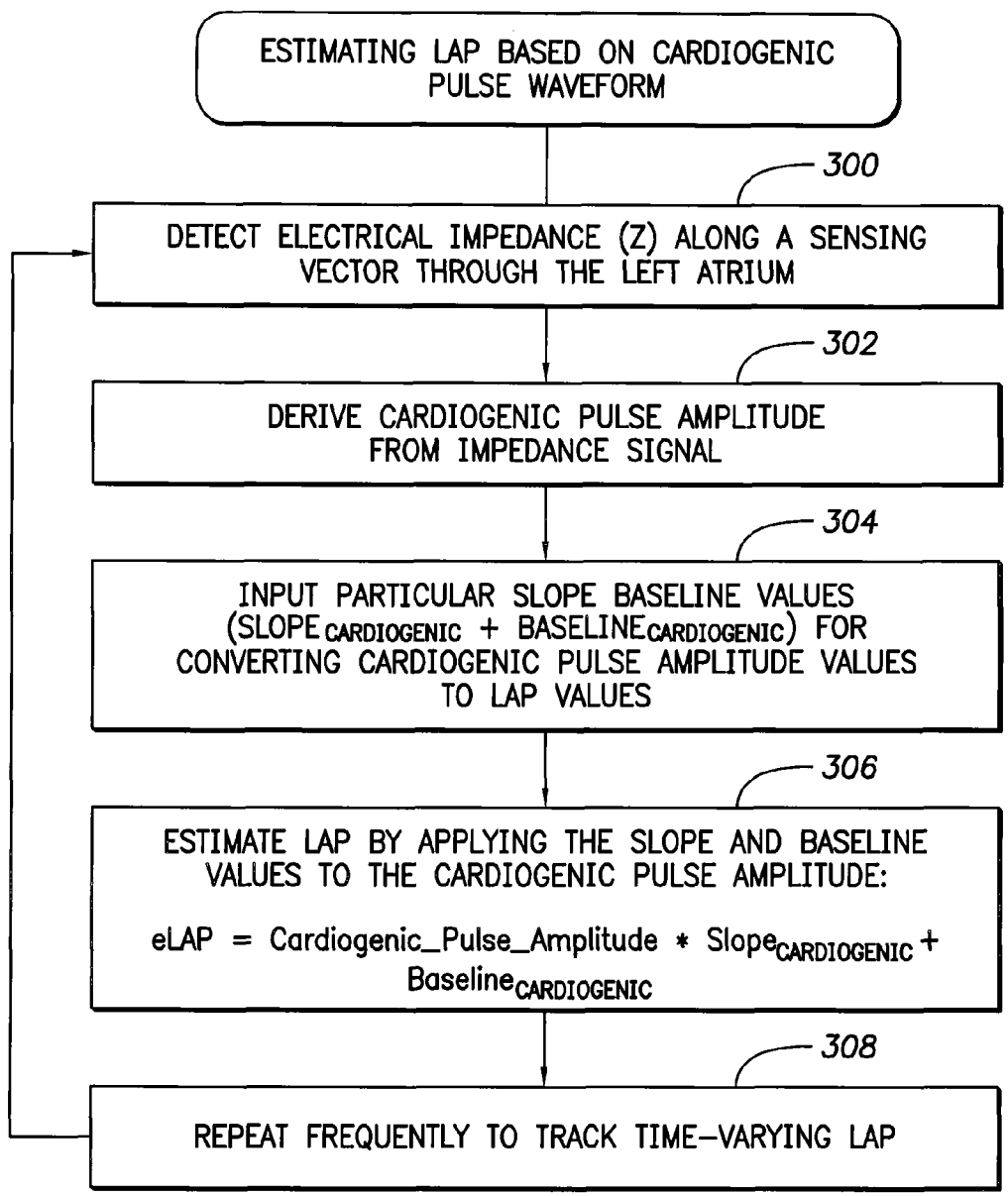
FIG. 11 is a flow diagram summarizing a second illustrative technique wherein LAP is estimated based on cardiogenic pulse amplitudes, and which also may be performed in accordance with the general technique of FIG. 2.

FIG. 11 illustrates a cardiogenic pulse amplitude-based LAP detection example. That is, the parameter derived from the electrical impedance signal (Z) (particularly $Z_0$) at step 102 of FIG. 2 is cardiogenic pulse amplitude. Alternatively, the cardiogenic pulse amplitude may be obtained without necessarily first detecting impedance by, for example, detecting conductance instead. The extracted pulse amplitude may alternatively be selected to match a corresponding V-wave (i.e., venous filling wave) within the cardiogenic impedance signal. Continuing with an impedance-based technique, it is assumed that cardiogenic pulse amplitude is inversely proportional to LAP (at least when the cardiogenic pulse amplitude is derived from an impedance signal sensed along a vector passing through the left atrium.) Accordingly, a linear model relating cardiogenic pulse amplitude to LAP is exploited. At step 300, the pacer/ICD detects electrical impedance (Z) along a sensing vector through the left atrium. At step 302, the pacer/ICD derives a cardiogenic pulse amplitude from the waveform of the detected electrical impedance signal. At step 304, the pacer/ICD inputs the particular slope and baseline values ($\text{Slope}_{CARDIOGENIC}$ +$\text{Baseline}_{CARDIOGENIC}$) for converting cardiogenic pulse amplitudes to LAP, which are predetermined conversion values that the pacer/ICD retrieves from memory. Calibration techniques of the type discussed above may be used to initially derive the conversion values and to re-calibrate the values, if needed. At step 306, the pacer/ICD estimates LAP by applying the slope and baseline values (input at step 304) to the cardiogenic pulse amplitude value (derived at step 302):

$$eLAP = \text{Cardiogenic\_Pulse\_Amplitude} * \text{Slope}_{CARDIOGENIC} + \text{Baseline}_{CARDIOGENIC}$$

As indicated by step 308, the pacer/ICD can repeat steps 300-306 frequently so as to track a time-varying LAP function, i.e. LAP(t), based on cardiogenic pulse amplitude values. That is, in some implementations, individual cardiogenic pulse amplitude values are detected substantially in real-time so as to permit changes in LAP to be tracked substantially in real-time as well. LAP estimates determined from conductance values may be combined with LAP estimates determined from the cardiogenic pulse amplitudes to provide a combined LAP estimate.

Figure 12:
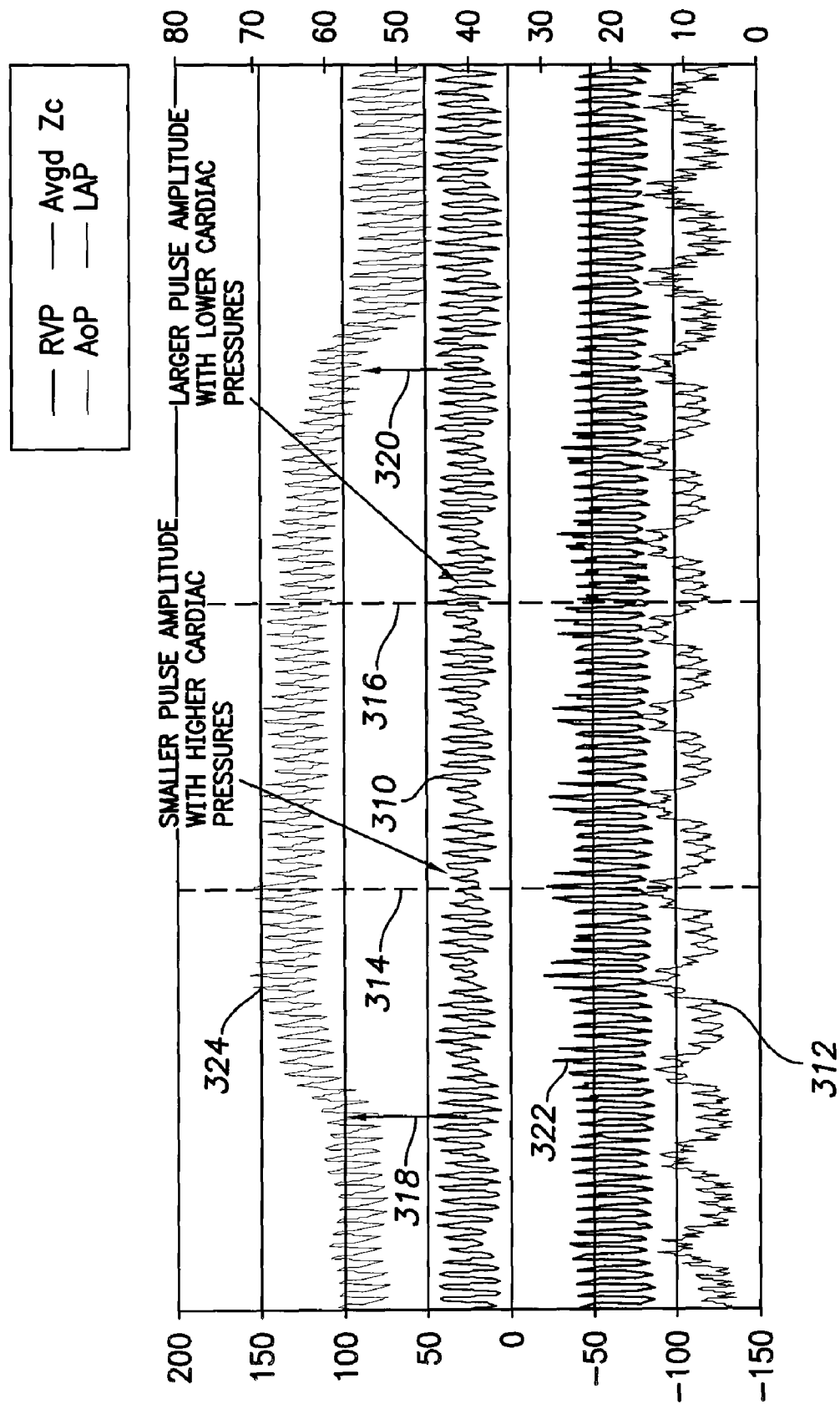
FIG. 12 is a graph illustrating cardiogenic pulse amplitude and LAP that may be exploited by the calibration procedures of FIG. 9.

FIG. 12 illustrates cardiogenic pulse amplitudes. Briefly, the figure includes graphs of data obtained for an animal test subject including a cardiogenic impedance signal trace 310 and a corresponding LAP trace 312. Note that, at times when the cardiogenic pulse amplitude is low, such as at time 314, LAP is large. Likewise, at times when the cardiogenic pulse amplitude is large, such as at time 316, LAP is small. That is, the two signals are substantially inversely proportional to each other. In the example of FIG. 12, a pressure afterload was induced within the animal using a balloon beginning at time 318 and ending at time 320 to emulate heart failure. It can also be seen that the magnitude of the difference between small pulse amplitudes and large pulse amplitude is greater during the emulated heart failure, suggesting that cardiogenic pulse amplitude-based LAP estimation technique is particularly effective in patients with heart failure. For comparison purposes, the figure also provides traces for right ventricular pressure (RVP) 322 and aortic pressure (AoP) 324. Aortic pressure increased significantly due to balloon inflation. Note that the horizontal time scale of the figure covers approximately one minute.

Figure 13:
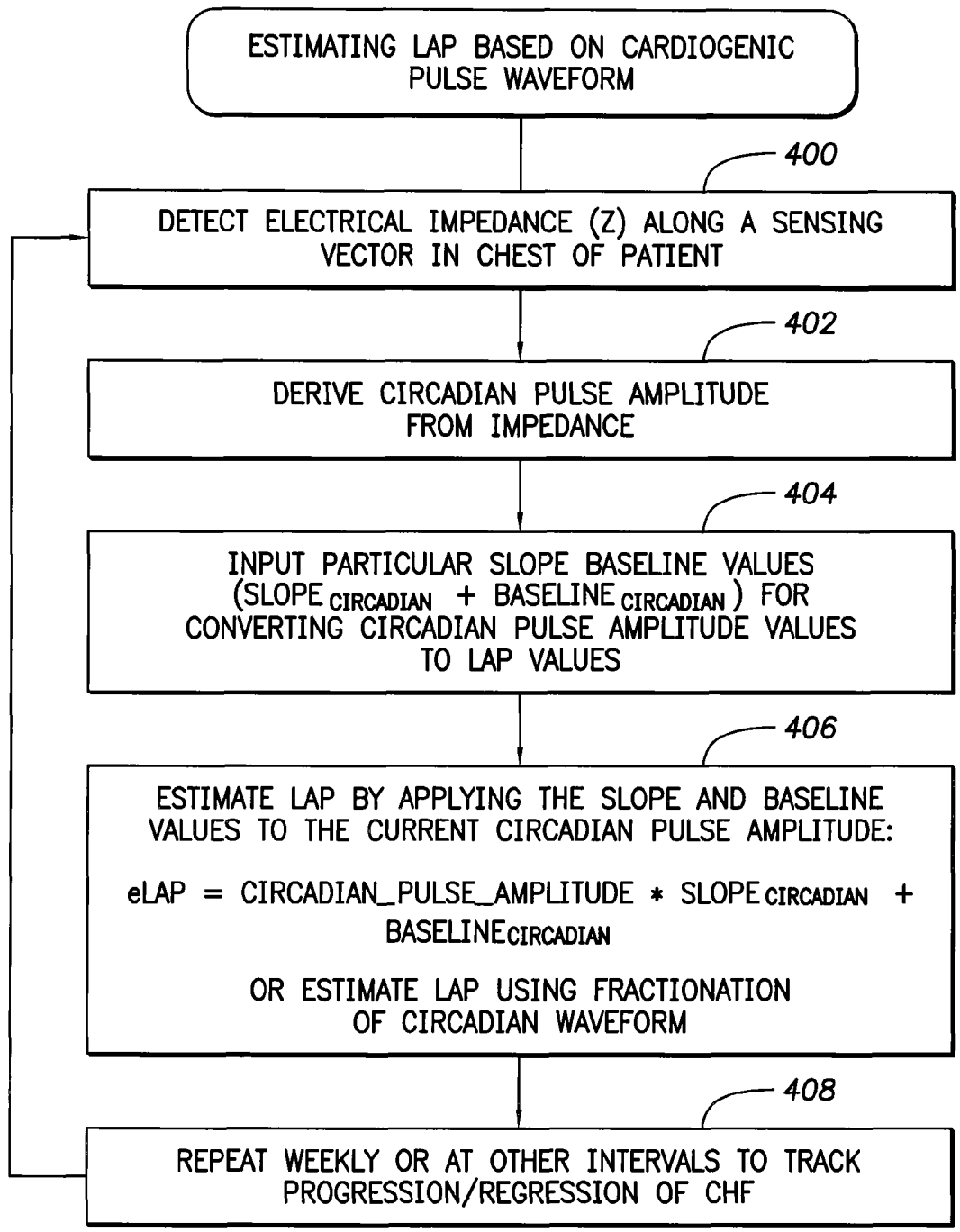
FIG. 13 is a flow diagram summarizing a third illustrative technique wherein LAP is estimated based on circadian rhythm pulse amplitudes, and which also may be performed in accordance with the general technique of FIG. 2.

FIG. 13 illustrates a circadian pulse amplitude-based LAP detection example. That is, the parameter derived from the electrical impedance signal (Z) at step 102 of FIG. 2 is the circadian pulse amplitude value (and is typically derived from the raw impedance signal ($Z_0$)). Alternatively, the circadian pulse amplitude may be obtained without necessarily first detecting impedance by, for example, detecting conductance instead. Continuing with an impedance-based, as already noted, the circadian pulse amplitude represents the daily variation in the impedance signal and is preferably calculated once per day. Within healthy patients, there is typically a significant daily variation in circadian impedance and so the circadian pulse amplitude may be 20 ohms or more. Within patients suffering from heart failure, however, there is typically little or no significant daily variation in circadian impedance and so the circadian pulse amplitude is at or near zero. Hence, progression of heart failure correlates with a decrease in circadian pulse amplitudes. There is also a correlation with LAP and heart failure, i.e. LAP increases due to progression of heart failure. Accordingly, there is a correlation between decreasing circadian pulse amplitudes and increasing LAP. With the technique of FIG. 14, it is assumed that circadian pulse amplitude is inversely proportional to LAP. Accordingly, a linear model relating circadian pulse amplitude to LAP is exploited.

At step 400, the pacer/ICD detects impedance along a sensing vector in the chest of the patient, such as between an LV tip electrode and the device housing. The sensing vector need not pass through the left atrium. At step 402, the pacer/ICD derives a circadian pulse amplitude from the impedance signal. The circadian component of the electrical impedance signals is the component that does not vary due to respiration or the beating of the heart of the patient. It remains substantially constant, except for the aforementioned circadian variations. The circadian pulse amplitude represents the difference between impedance waveform amplitudes at night when the patient typically is laying supine and those during the day when the patient typically is standing upright and is preferably calculated once per day. Circadian pulse amplitudes are illustrated in FIG. 14.

Figure 14:
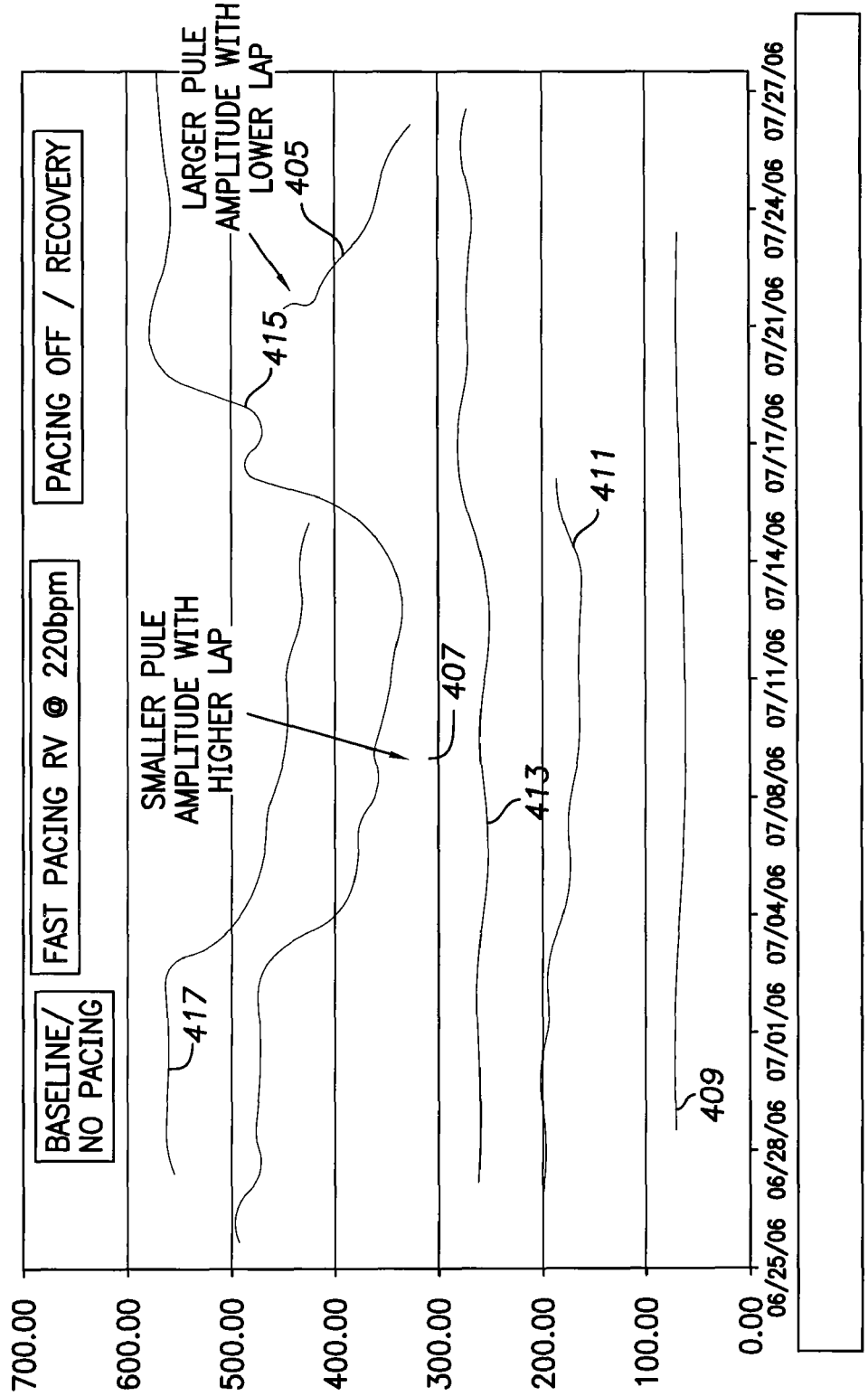
FIG. 14 includes a graph illustrating circadian variations in electrical impedance values from which the circadian pulse amplitude of FIG. 13 is derived.

FIG. 14 illustrates a circadian impedance signal 403 tracked over a one month period within an animal test subject in which heart failure is emulated via rapid pacing during a middle portion of the time interval shown. Similar circadian patterns have been recorded from patients implanted with the impedance measuring device. Circadian variations in signal 403 are exhibited. These are most clearly seen in the portions of the graph wherein rapid pacing is not performed, i.e. during the early and later portions of the data shown. The circadian pulse amplitude represents the difference between peak and nadir points within the circadian impedance signal over a one-day period. Reference numeral 405 identifies a relatively large circadian pulse amplitude occurring during a period of time when heart failure is not being emulated, and hence LAP is high. Reference numeral 407 identifies a relatively smaller circadian pulse amplitude occurring during a period of time when heart failure is being emulated, and hence LAP is lower. (LAP itself is not shown in the figure.) Although the data of FIG. 14 was obtained from a single (animal) test subject in which heart failure was temporarily emulated via a rapid pacing protocol, a similar variation in circadian pulse amplitude is exhibited within human patients as well, when heart failure occurs naturally. For comparison purposes, the figure also provides traces for $RV_{coil}$-case impedance/average impedance 409, $RV_{ring}$-case impedance/average impedance 411, $RA_{ring}$-case impedance/average impedance 413, $RV_{ring}$–$LV_{ring}$ impedance/average impedance 415, and $LV_{ring}$–$RA_{ring}$ impedance/average impedance 417, which demonstrate that not all vectors are equal in their ability to detect the circadian pulse amplitude. This may require individualizing the selected vector for estimating LAP in the clinical setting.

At step 404 of FIG. 13, the pacer/ICD inputs the particular slope and baseline values ($Slope_{CIRCADIAN}$+$Baseline_{CIRCADIAN}$) for converting circadian pulse amplitudes to LAP, which are predetermined conversion values that the pacer/ICD retrieves from memory. The conversion values may be obtained from a population of test subjects using linear regression techniques, as with the calibration technique of FIG. 9. At step 406, the pacer/ICD estimates LAP by applying the slope and baseline values (input at step 404) to the circadian pulse amplitude value (derived at step 402):

$$eLAP=\text{Circadian\_Pulse\_Amplitude}*Slope_{CIRCADIAN}+Baseline_{CIRCADIAN}$$

By way of a simple example, the circadian pulse amplitude within a healthy patient may be 20 ohms with an LAP of 10 mmHg. Within a patient with severe CHF, the circadian pulse amplitude may be 0 ohms with an LAP of 30 mmHg. Accordingly, the pacer/ICD can estimate LAP for a particular patient by scaling the circadian pulse amplitude value detected therein. That is, if the circadian pulse amplitude is found to be 10 ohms within the patient, the pacer/ICD then estimates the LAP of the patient as being 20 mmHg. As indicated by step 408, the pacer/ICD can repeat steps 400-406 once per day so as to track changes in LAP occurring over extended intervals (i.e. weeks or months). That is, unlike the implementations described above, changes in LAP are not usually tracked in real-time when using circadian pulse amplitudes.

Referring again to FIG. 14, note that during the period of time while heart failure is emulated the circadian waveform is quite "noisy", i.e. there is a relatively high degree of fractionation. This period of increased fractionation is also correlated with increased LAP. The fractionation of the circadian waveform may also be used to estimate LAP. Fractionation is more fully described in the following section, specifically with regard to the fractionation of the cardiogenic component of the impedance signal. Techniques for exploiting the fractionation of the cardiogenic impedance waveform are described for use in estimated LAP. These techniques may also be applied to estimating LAP based on fractionation of the circadian impedance waveform.

Figure 15:
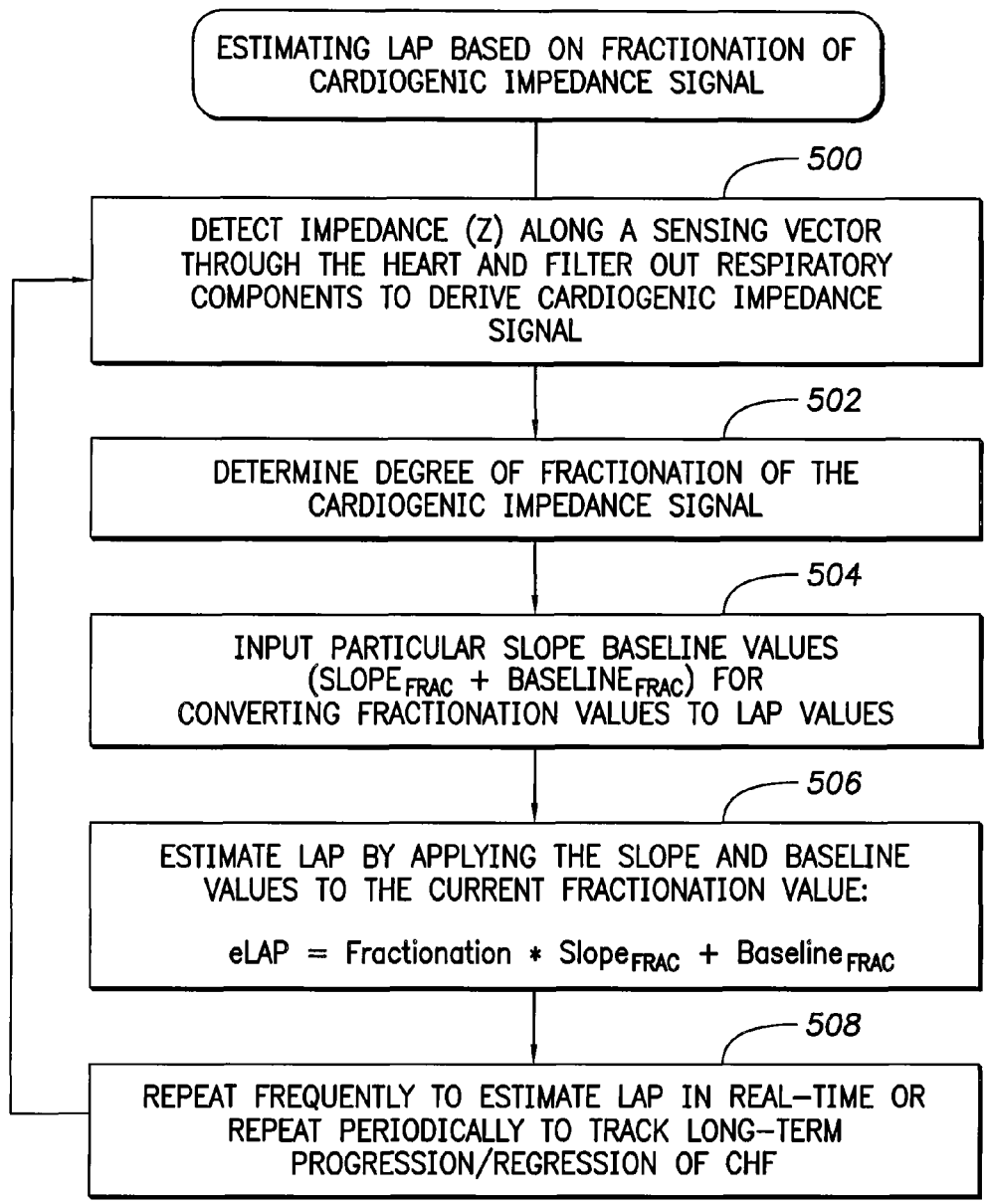
FIG. 15 is a flow diagram summarizing a fourth illustrative technique wherein LAP is estimated based on fractionation of cardiogenic impedance signals, and which also may be performed in accordance with the general technique of FIG. 2.

FIG. 15 illustrates a fractionation-based LAP detection example. That is, the parameter derived from the electrical impedance signal (Z) (preferably from the cardiogenic impedance signal ($Z_0$)) at step 102 of FIG. 2 is an indication of the fractionation of cardiogenic components of the impedance signal. Alternatively, the fractionation value may be obtained without necessarily first detecting impedance by, for example, detecting conductance instead. Continuing with an impedance-based example, as already noted, fractionation represents the degree of fractionation in a cardiogenic component of the impedance signal, i.e. that portion of the impedance signal that varies in accordance with the beating of the heart. The cardiogenic component of the impedance signal may be derived from the detected impedance signal by filtering out non-cardiogenic components using otherwise conventional techniques. Fractionation increases due to increasing mechanical dyssynchrony and abnormal transvalvular flow patterns within the heart arising due to heart failure. Components of the cardiogenic impedance waveform may separate out into individual atrial contraction waves (A-wave), ventricular contraction waves (C-wave), and venous filling waves (V-wave). LAP also typically increases due to heart failure. Accordingly, there is a correlation between increasing fractionation and increasing LAP. With the technique of FIG. 14, it is assumed that increasing fractionation of the cardiogenic component of the impedance signal is directly proportional to LAR. Accordingly, LAP may be estimated based on fractionation using conversion factors calibrated for converting fractionation values to LAP values.

At step 500, the pacer/ICD detects electrical impedance along a sensing vector passing through the heart of the patient and filters out non-cardiogenic components. However, the sensing vector need not pass through the left atrium. At step 502, the pacer/ICD determines the degree of fractionation of the cardiogenic impedance signal. Fractionation of a cardiogenic impedance signal due to heart failure is illustrated with FIG. 16. A first graph 501 illustrates a cardiogenic impedance trace (solid line) and an IEGM trace (dotted line) for a patient without significant heart failure. The impedance trace (IM avg.) was obtained via bipolar sensing RV tip to RV ring. The IEGM in an LV IEGM and is shown scaled according to "counts" from an analog to digital converter (ADC). A second graph 503 instead illustrates a cardiogenic impedance trace (solid line) and an IEGM trace (dotted line) for a patient with heart failure. As can be seen, within the normal heart trace 501, the portion of the cardiogenic impedance signal associated with each individual heart beat exhibits one notch. This single notch arises due to the uniform contraction of the RV and the LV and corresponds to the QRS complex of the IEGM. However, in the diseased heart of graph 503, an additional significant notch appears within the cardiogenic impedance trace within the time interval of the T-wave of the IEGM. This additional notch appears to occur due to a time delay between LV contraction and RV contraction and hence may be indicative of mechanical dyssynchrony between the LV and RV associated with heart failure.

When determining the degree of fractionation of the cardiogenic impedance signal at step 502 of FIG. 15, the pacer may calculate a fractionation index representative of a degree of fractionation of the cardiogenic impedance signal. The fractionation index may be derived, e.g., by simply counting a number of notches appearing within portions of the signal representative of individual heartbeats. A patient whose heartbeat exhibits five notches has a higher degree of fractionation than a patient whose heartbeat exhibits only four notches. As noted, the notches often correspond to periods of time when chambers of the heart are not beating uniformly, i.e. the greater the number of notches, the greater the degree of mechanical dyssynchrony. Though, even a healthy and fully synchronized heart will exhibit some notches within the cardiogenic impedance signals. That is, for a normal patient free of heart failure, the characteristic morphology of a cardiogenic impedance pattern for a single heartbeat shows relatively smooth waves that follow the cardiac cycle, with relatively little raggedness (i.e., "fractionation") at the crest of each impedance peak (or trough). During early onset of heart failure, the cardiogenic impedance pattern for a single heartbeat develops a characteristic morphology of notches in or near the crests—i.e., a moderate degree of fractionation. During late heart failure conditions, cardiogenic impedance pattern for a single heartbeat develops a characteristic morphology of high volatility and fractionation, where the magnitude of the notches increases significantly and their frequency of occurrence is high. The fractionation index may also be derived by determining the frequencies associated with the cardiogenic impedance signal using, for example, a Fast Fourier Transform (FFT). The greater the number of notches and troughs within the cardiogenic impedance signal, the higher the frequencies of the signal, and the greater the mechanical dyssynchrony. Techniques for identifying and comparing notches and troughs within a cardiogenic impedance signal are discussed in the related patents, cited above.

At step 504 of FIG. 15, the pacer/ICD inputs the particular slope and baseline values ($Slope_{FRAC}$+$Baseline_{FRAC}$) for converting fractionation values to LAP, which are predetermined conversion values that the pacer/ICD retrieves from memory. The conversion values may be obtained from a population of test subjects using linear regression techniques, as with the calibration technique of FIG. 9. At step 506, the pacer/ICD estimates LAP by applying the slope and baseline values (input at step 504) to the fractionation values (derived at step 502):

$$eLAP=\text{Fractionation}*Slope_{FRAC}+Baseline_{CIRCADIAN}$$

By way of a simple example, the cardiogenic impedance signal of a healthy patient may exhibit a single notch with an LAP of 10 mmHg. Within a patient with severe CHF, the cardiogenic impedance signal may exhibit five notches with an LAP of 30 mmHg. Accordingly, the pacer/ICD can estimate LAP for a particular patient by scaling the number of notches detected within the cardiogenic impedance signal of the patient. That is, if three notches are found within the patient, the pacer/ICD then estimates the LAP of the patient as being 20 mmHg. As indicated by step 508, the pacer/ICD can repeat steps 500-506 once per week so as to track changes in LAP occurring over extended intervals (i.e. weeks or months). Alternatively, the estimated LAP derived from fractionation may be obtained in real-time on beat-to-beat basis. Insofar as real-time tracking is concerned, in at least some cases, beat-to-beat changes in LAP are correlated with beat-to-beat changes in cardiogenic fractionation. For example, atrial fibrillation (AF) may induce both an increase in LAP and an increase in fractionation of the cardiogenic impedance waveform. In some implementations, it is desirable to trigger the estimation of LAP based on changes in cardiac rhythm. For example, the detection of a sharp increase in atrial rate may be used to activate the LAP estimation system to estimate LAP.

Figure 17:
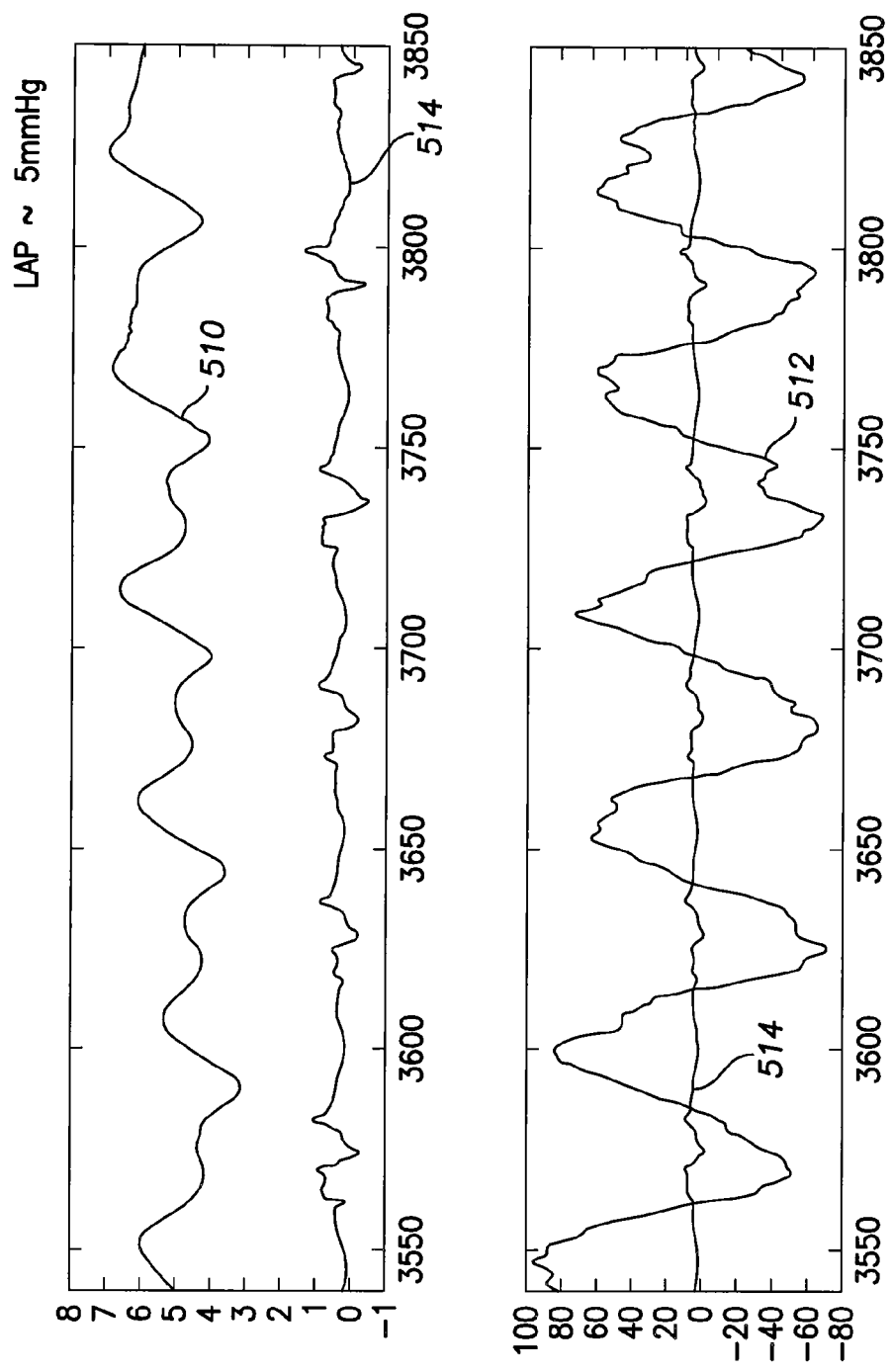
FIG. 17 is another graph illustrating exemplary cardiogenic impedance signals that may be processed in accordance with the technique of FIG. 15, and particularly illustrating the lack of fractionation of the cardiogenic impedance signal exhibited without heart failure in an animal test subject.
Figure 18:
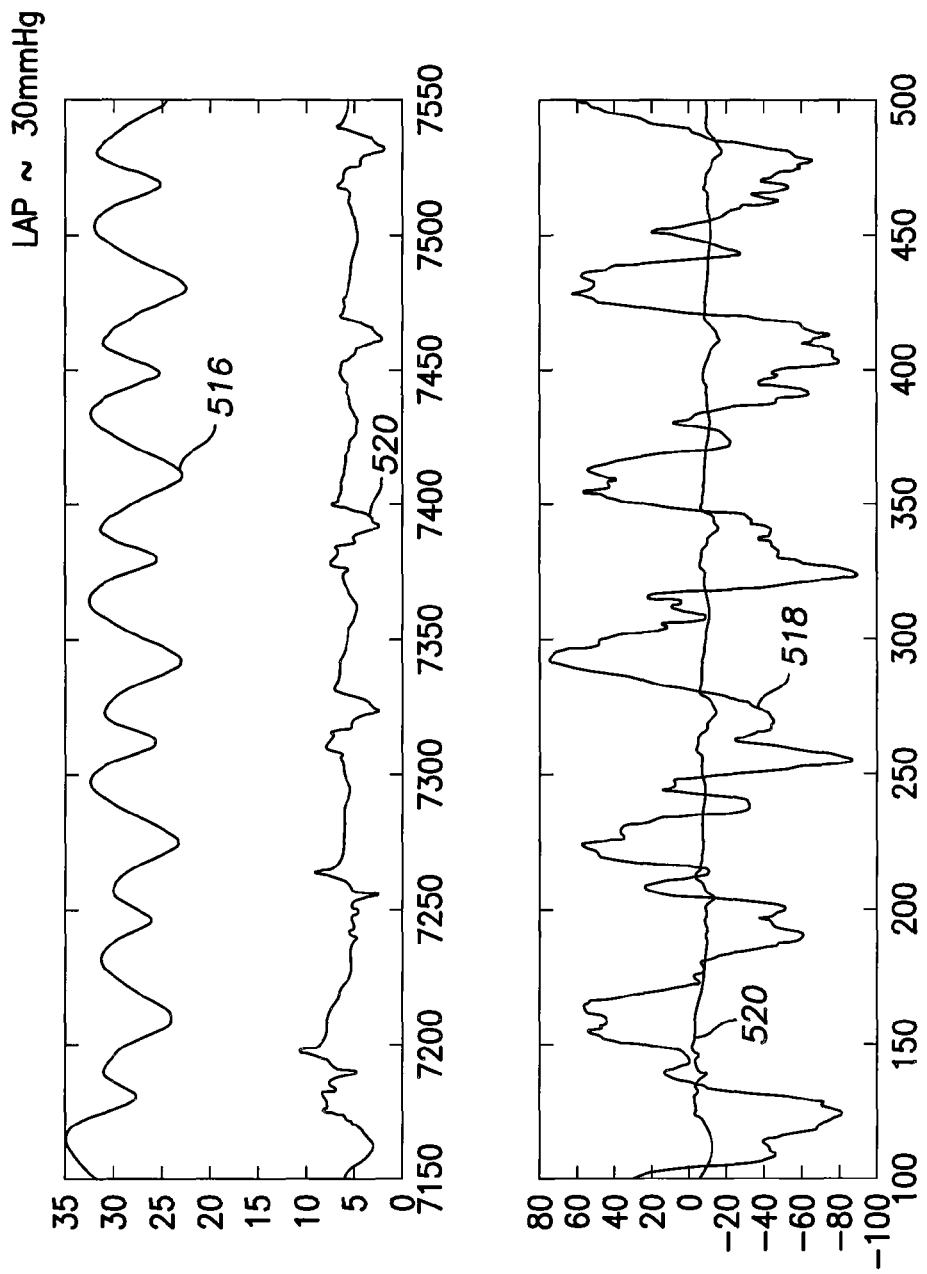
FIG. 18 is another graph illustrating exemplary cardiogenic impedance signals that may be processed in accordance with the technique of FIG. 15, and particularly illustrating elevated LAP levels and corresponding fractionation of a cardiogenic impedance signal exhibited during heart failure as emulated in an animal test subject.

FIGS. 17 and 18 provide additional graphs illustrating fractionation. FIG. 17 illustrates a data obtained from an animal test subject with healthy heart. An LAP trace 510 exhibits nominal pressure levels of about 5 mmHg. The corresponding cardiogenic impedance trace 512 exhibits very little fractionation. An IEGM 514 is also illustrates in each graph (subject to differing vertical scales.) The time scale for the figure covers only a few heartbeats. Heart failure was then emulated in this test subject and additional LAP and cardiogenic impedance traces were obtained, which are shown in FIG. 18. More specifically, FIG. 18 illustrates data obtained from the same test subject two hours later after heart failure was emulated. A LAP trace 516 exhibits elevated pressure levels of about 30 mmHg. The corresponding cardiogenic impedance trace 518 exhibits substantial fractionation. An IEGM 520 is also illustrates in each graph (again subject to differing vertical scales.) As before, the time scale for the figure covers only a few heartbeats. As can be seen from a comparison of the two graphs, the elevated LAP associated with heart failure correlates with increased fractionation.

Thus, a variety of techniques for estimating LAP and tracking heart failure are provided. These may be supplemented by using other non-impedance-based cardiac pressure detection and heart failure detection techniques. In some implementations, before an alarm is activated or any therapy is automatically delivered, the pacer/ICD employs at least one other detection technique to corroborate the detection of heart failure. Techniques for detecting or tracking heart failure are set forth the following patents and patent applications: U.S. Pat. No. 6,328,699 to Eigler, et al., entitled "Permanently Implantable System and Method for Detecting, Diagnosing and Treating Congestive Heart Failure"; U.S. Pat. No. 6,970,742 to Mann, et al., entitle "Method for Detecting, Diagnosing, and Treating Cardiovascular Disease"; U.S. Pat. No. 7,115,095 to Eigler, et al., entitled "Systems and Methods for Detecting, Diagnosing and Treating Congestive Heart Failure"; U.S. patent application Ser. No. 11/100,008, of Kil et al., entitled "System And Method For Detecting Heart Failure And Pulmonary Edema Based On Ventricular End-Diastolic Pressure Using An Implantable Medical Device", filed Apr. 5, 2005; U.S. patent application Ser. No. 11/014,276, of Min et al., entitled "System And Method For Predicting Heart Failure Based On Ventricular End-Diastolic Volume/Pressure Using An Implantable Medical Device", filed Dec. 15, 2004; U.S. patent application Ser. No. 10/810,437, of Bornzin et al., entitled "System and Method for Evaluating Heart Failure Based on Ventricular End-Diastolic Volume Using an Implantable Medical Device," filed Mar. 26, 2004 and U.S. patent application Ser. No. 10/346,809, of Min et al., entitled "System and Method for Monitoring Cardiac Function via Cardiac Sounds Using an Implantable Cardiac Stimulation Device," filed Jan. 17, 2003. See also: U.S. Pat. No. 6,572,557, to Tchou, et al., cited above. U.S. Pat. No. 6,645,153, to Kroll et al., entitled "System and Method for Evaluating Risk of Mortality Due To Congestive Heart Failure Using Physiologic Sensors", and U.S. Pat. No. 6,438,408 to Mulligan et al., entitled "Implantable Medical Device For Monitoring Congestive Heart Failure."

Also, other calibration procedures may potentially be exploited in connection with the calibration techniques described herein. See, for example, U.S. Patent Application 2004/0019285 of Eigler, et al., cited above, particularly the various linear regression techniques discussed therein.

Although primarily described with respected to examples having a pacer/ICD, other implantable medical devices may be equipped to exploit the techniques described herein. For the sake of completeness, an exemplary pacer/ICD will now be described, which includes components for performing the functions and steps already described. Also, an exemplary external programmer will be described, which includes components for performing the calibration steps already described.

Exemplary Pacer/ICD

Figure 20:
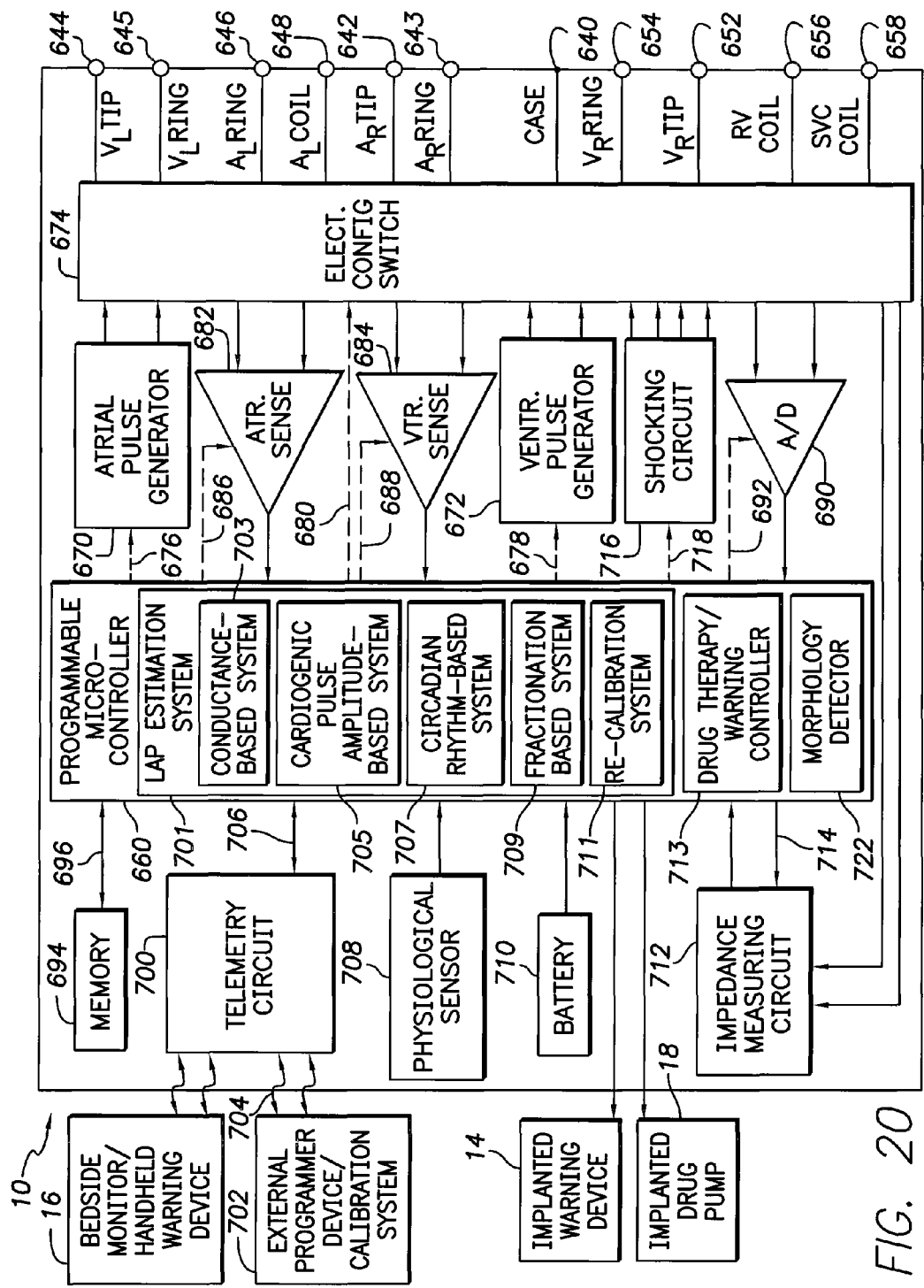
FIG. 20 a functional block diagram of the pacer/ICD of FIG. 19, illustrating basic circuit elements that provide cardioversion, defibrillation and/or pacing stimulation in the heart and particularly illustrating components for estimating LAP based on impedance.
Figure 21:
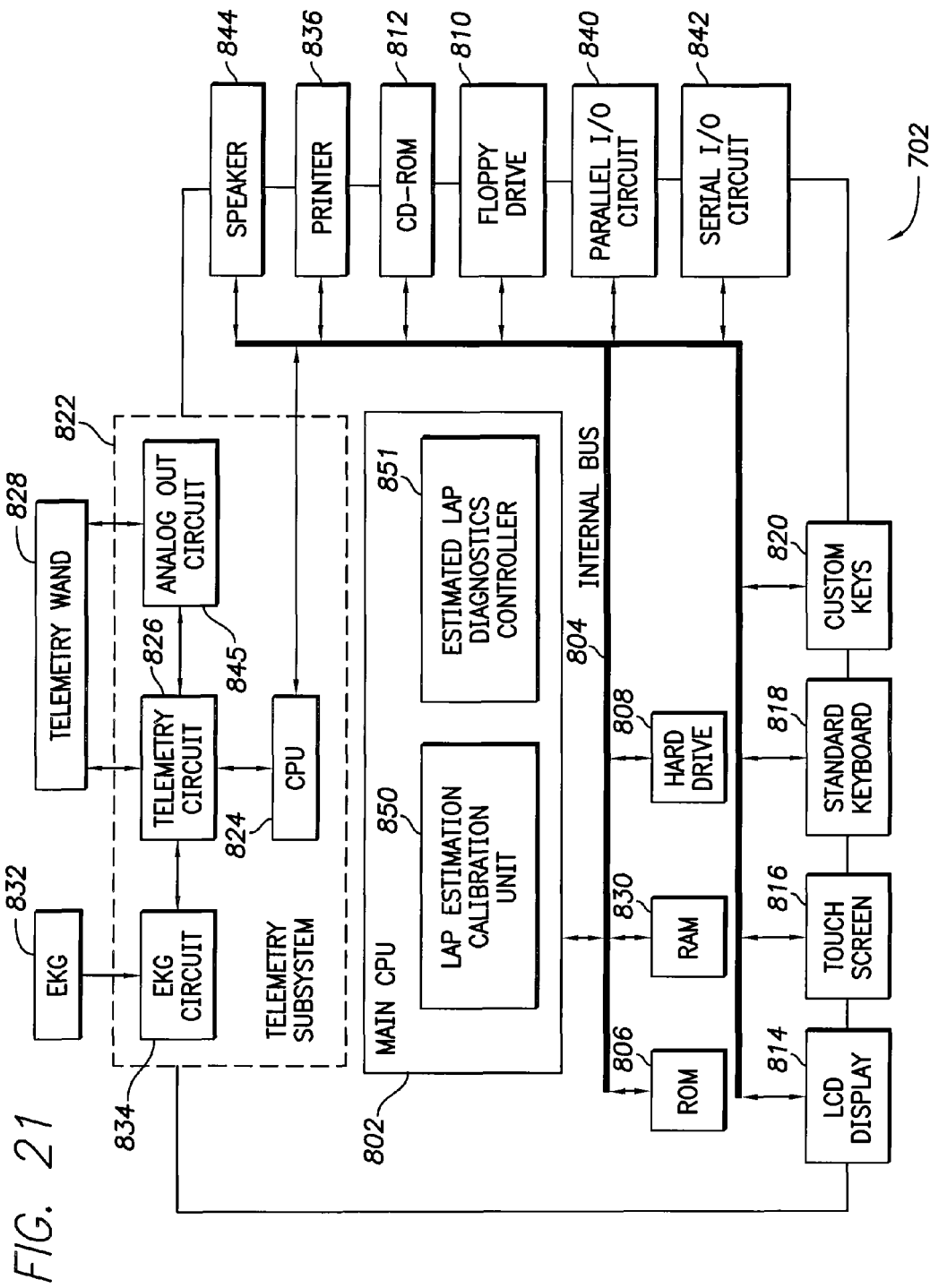
FIG. 21 is a functional block diagram illustrating components of a device programmer of FIG. 20, and in particular illustrating a programmer-based LAP estimation calibration system.

With reference to FIGS. 19 and 20, a description of an exemplary pacer/ICD will now be provided. FIG. 19 provides a simplified block diagram of the pacer/ICD, which is a dual-chamber stimulation device capable of treating both fast and slow arrhythmias with stimulation therapy, including cardioversion, defibrillation, and pacing stimulation, and also capable of estimating LAP or other forms of cardiac pressure using impedance signals. To provide other atrial chamber pacing stimulation and sensing, pacer/ICD 10 is shown in electrical communication with a heart 612 by way of a left atrial lead 620 having an atrial tip electrode 622 and an atrial ring electrode 623 implanted in the atrial appendage. Pacer/ICD 10 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a CS lead 624 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 624 is designed to receive atrial and ventricular cardiac signals and to deliver left ventricular pacing therapy using at least a left ventricular tip electrode 626 and a LV ring electrode 625, left atrial pacing therapy using at least a left atrial ring electrode 627, and shocking therapy using at least a left atrial coil electrode 628. With this configuration, biventricular pacing can be performed. Although only three leads are shown in FIG. 19, it should also be understood that additional leads (with one or more pacing, sensing and/or shocking electrodes) might be used and/or additional electrodes might be provided on the leads already shown.

A simplified block diagram of internal components of pacer/ICD 10 is shown in FIG. 20. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 640 for pacer/ICD 10, shown schematically in FIG. 20, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 645, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 623. To achieve left chamber sensing, pacing and shocking, the connector includes at least a left ventricular tip terminal ($V_L$ TIP) 644, a left ventricular ring terminal ($V_L$ RING) 645, a left atrial ring terminal ($A_L$ RING) 646, and a left atrial shocking terminal ($A_L$ COIL) 648, which are adapted for connection to the left ventricular ring electrode 626, the left atrial ring electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($V_R$ COIL) 656, and an SVC shocking terminal (SVC COIL) 658, which are adapted for connection to the right ventricular tip electrode 632, right ventricular ring electrode 634, the $V_R$ coil electrode 636, and the SVC coil electrode 638, respectively.

At the core of pacer/ICD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 20, an atrial pulse generator 670 and a ventricular pulse generator 672 generate pacing stimulation pulses for delivery by the right atrial lead 620, the right ventricular lead 630, and/or the CS lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, CS lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/ICD 10 utilizes the atrial and ventricular sensing circuits, 682 and 684, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the CS lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 694 through a telemetry circuit 700 in telemetric communication with the external device 702, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of pacer/ICD 10 (as contained in the microcontroller 660 or memory 694) to be sent to the external device 702 through an established communication link 704. Pacer/ICD 10 further includes an accelerometer or other physiologic sensor 708, commonly referred to as a "rate-responsive" sensor because it is typically used to adjust pacing stimulation rate according to the exercise state of the patient. However, the physiological sensor 708 may further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV delay, V-V delay, etc.) at which the atrial and ventricular pulse generators, 670 and 672, generate stimulation pulses. While shown as being included within pacer/ICD 10, it is to be understood that the physiologic sensor 708 may also be external to pacer/ICD 10, yet still be implanted within or carried by the patient. A common type of rate responsive sensor is an activity sensor incorporating an accelerometer or a piezoelectric crystal, which is mounted within the housing 640 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 710, which provides operating power to all of the circuits shown in FIG. 6. The battery 710 may vary depending on the capabilities of pacer/ICD 10. If the system only provides low voltage therapy, a lithium iodine or lithium copper fluoride cell typically may be utilized. For pacer/ICD 10, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, appropriate batteries are employed.

As further shown in FIG. 20, pacer/ICD 10 is shown as having an impedance measuring circuit 712, which is enabled by the microcontroller 660 via a control signal 714. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 712 is advantageously coupled to the switch 774 so that any desired electrode may be used. The impedance measuring circuit 712 also detects the impedance signals discussed above to use in estimating LAP. That is, impedance measuring circuit 712 is an electrical impedance (Z) detector operative to detect an electrical impedance (Z) signal within the patient along at least one sensing vector wherein impedance is affected by cardiac pressure.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Insofar as LAP estimation is concerned, the microcontroller includes an LAP estimation system 701 operative to estimate LAP or other forms of cardiac pressure based on parameters derived from impedance signals using the techniques described above. That is estimation system is operative to: measure a predetermined parameter within patient tissues, the parameter being influenced by an electrical field applied to tissues of the patient including cardiac tissues, the parameter also being affected by cardiac pressure; and estimate cardiac pressure within the patient by applying predetermined conversion factors to the measured parameter. For example, the estimation system may be equipped to detect an electrical impedance (Z) signal within the patient along a sensing vector wherein impedance is affected by cardiac pressure; derive a predetermined parameter from the electrical impedance (Z) signal; input predetermined conversion factors from memory for converting the parameter derived from the electrical impedance signal (Z) to cardiac pressure; and estimate cardiac pressure within the patient by applying the conversion factors to the parameter derived from the electrical impedance (Z) signal. Estimation system 701 includes: a conductance-based system 703 operative to estimate cardiac pressure within the patient by applying the conversion factors to electrical conductance parameters derived from the electrical impedance (Z) signal; an cardiogenic pulse amplitude-based system 705 operative to estimate cardiac pressure within the patient by applying the conversion factors to cardiogenic pulse amplitude parameters derived from the electrical impedance (Z) signal; a circadian pulse amplitude-based system 707 operative to estimate cardiac pressure within the patient by applying the conversion factors to circadian pulse amplitude parameters derived from the electrical impedance (Z) signal; and a fractionation-based system 709 operative to estimate cardiac pressure within the patient by applying the conversion factors to cardiogenic impedance fractionation parameters derived from the electrical impedance (Z) signal. Estimation system 701 also includes a re-calibration unit 711 operative to re-calibrate the conversion factors using techniques described above.

Diagnostic data pertaining to LAP is stored in memory 694. Warning and/or notification signals are generated, when appropriate, by a warning controller 713 then relayed to the bedside monitor 18 via telemetry system 700 or to external programmer 702 (or other external calibration system.) Controller 713 can also controller an implantable drug pump, if one is provided, to deliver appropriate medications. Terminals for connecting the implanted warning device and the implanted drug pump to the pacer/ICD are not separately shown. Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

Exemplary External Programmer

FIG. 21 illustrates pertinent components of an external programmer 702 for use in programming the pacer/ICD of FIG. 20 and for performing the above-described calibration techniques. For the sake of completeness, other device programming functions are also described herein. Generally, the programmer permits a physician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 702 may also be capable of processing and analyzing data received from the implanted device and from the EKG leads to, for example, render preliminary diagnosis as to medical conditions of the patient or to the operations of the implanted device.

Now, considering the components of programmer 702, operations of the programmer are controlled by a CPU 802, which may be a generally programmable microprocessor or microcontroller or may be a dedicated processing device such as an application specific integrated circuit (ASIC) or the like. Software instructions to be performed by the CPU are accessed via an internal bus 804 from a read only memory (ROM) 806 and random access memory 830. Additional software may be accessed from a hard drive 808, floppy drive 810, and CD ROM drive 812, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 814 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 816 overlaid on the LCD display or through a standard keyboard 818 supplemented by additional custom keys 820, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 702 to retrieve data stored within any implanted devices and to also retrieve EKG data from EKG leads, if any, coupled to the patient. To this end, CPU 802 transmits appropriate signals to a telemetry subsystem 822, which provides components for directly interfacing with the implanted devices, and the EKG leads. Telemetry subsystem 822 includes its own separate CPU 824 for coordinating the operations of the telemetry subsystem. Main CPU 802 of programmer communicates with telemetry subsystem CPU 824 via internal bus 804. Telemetry subsystem additionally includes a telemetry circuit 826 connected to telemetry wand 828, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 834 for receiving surface EKG signals from a surface EKG system 832. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/ICD is equipped to store that data.) Data retrieved from the implanted devices is stored by external programmer 702 either within a random access memory (RAM) 830, hard drive 808 or within a floppy diskette placed within floppy drive 810. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 702, the implanted devices may be further controlled to transmit additional data in real time as it is detected by the implanted devices, such as additional IEGM data, lead impedance data, and the like. Additionally, or in the alternative, telemetry subsystem 822 receives EKG signals from EKG leads 832 via an EKG processing circuit 834. As with data retrieved from the implanted device itself, signals received from the EKG leads are stored within one or more of the storage devices of the external programmer. Typically, EKG leads output analog electrical signals representative of the EKG. Accordingly, EKG circuit 834 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 802, the programming commands are converted to specific programmable parameters for transmission to the implanted devices via telemetry wand 828 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 836.

Additionally, CPU 802 also preferably includes an LAP estimation calibration unit 850 operative to perform the calibration procedures described above. CPU 802 also preferably includes an estimated LAP diagnostics controller 851 operative to control the display of estimated LAP values. As already noted, physician are often more familiar with LAP value than impedance values and hence benefit from LAP-based diagnostics displays that graphically illustrates changes in LAP within the patient, such as changes brought on by heart failure.

Programmer/monitor 702 also includes a modem 838 to permit direct transmission of data to other programmers via the public switched telephone network (PSTN) or other interconnection line, such as a T1 line or fiber optic cable. Depending upon the implementation, the modem may be connected directly to internal bus 804 may be connected to the internal bus via either a parallel port 840 or a serial port 842. Other peripheral devices may be connected to the external programmer via parallel port 840 or a serial port 842 as well. Although one of each is shown, a plurality of input output (IO) ports might be provided. A speaker 844 is included for providing audible tones to the user, such as a warning beep in the event improper input is provided by the physician. Telemetry subsystem 822 additionally includes an analog output circuit 845 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted devices and to reprogram the implanted device if needed. The descriptions provided herein with respect to FIG. 21 are intended merely to provide an overview of the operation of programmer and are not intended to describe in detail every feature of the hardware and software of the programmer and is not intended to provide an exhaustive list of the functions performed by the programmer.

Figure 22:
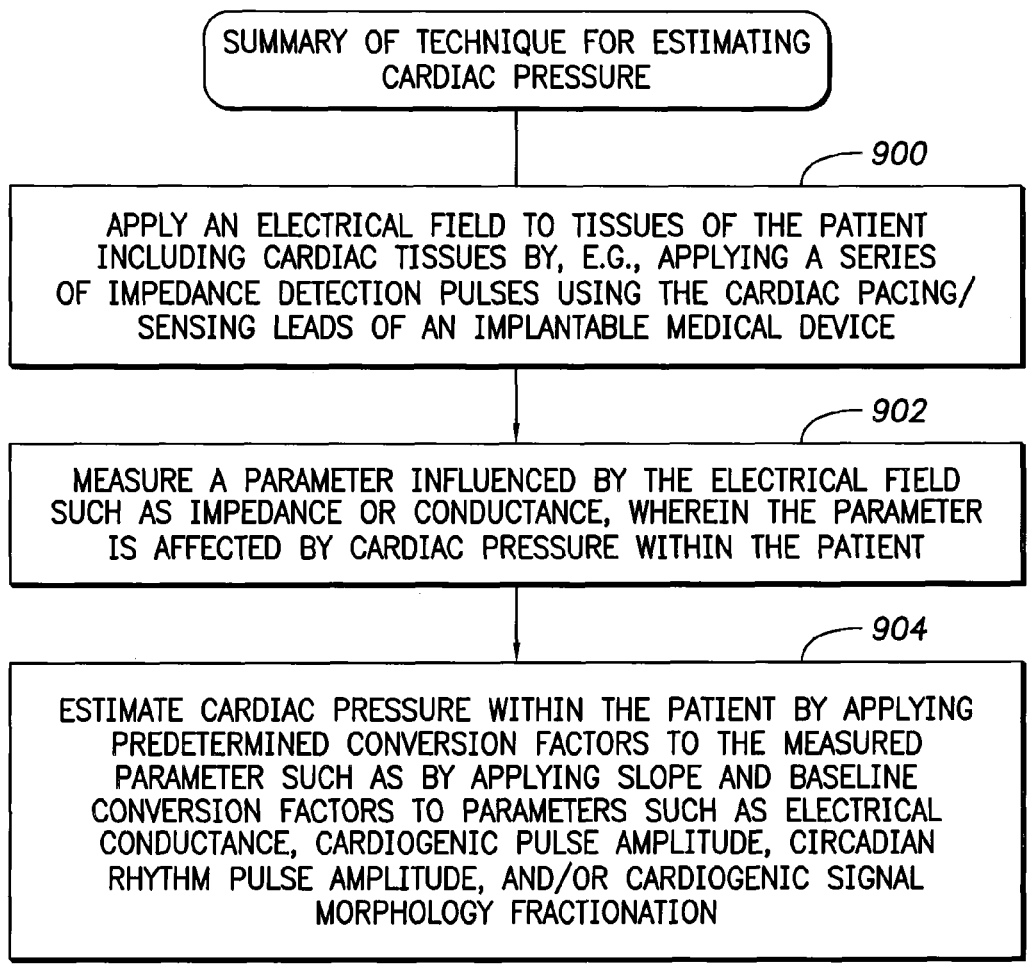
FIG. 22 is a flow diagram broadly summarizing the cardiac pressure estimation techniques that may be performed by the system of FIG. 1 or other implantable medical systems.

FIG. 22 provides a broad summary of the techniques discussed above. At step 900, an electrical field is applied to tissues of the patient, including cardiac tissues by, e.g., applying a series of impedance detection pulses using the cardiac pacing/sensing leads of an implantable medical device. Impedance detection pulses may be generated, for example, using the atrial or ventricular pulse generators of FIG. 20 and then applied to the tissues of the patient via the electrodes of FIG. 19. At step 902, a parameter is measured that is influenced by the electrical field, such as impedance or conductance, wherein the parameter is also affected by cardiac pressure within the patient. Impedance may be measured, for example, using the impedance measuring circuit of FIG. 20. At step 904, cardiac pressure is estimated within the patient by applying predetermined conversion factors to the measured parameter, such as by applying slope and baseline conversion factors to parameters such as electrical conductance, cardiogenic pulse amplitude, circadian rhythm pulse amplitude, and/or cardiogenic signal morphology fractionation, using techniques described above. Cardiac pressure may be estimated, for example, using the LAP estimation system of FIG. 20.

In the following sections, additional or alternative estimation and calibration systems and methods will be described.

Population-Based Default Conversion Parameters

Figure 23:
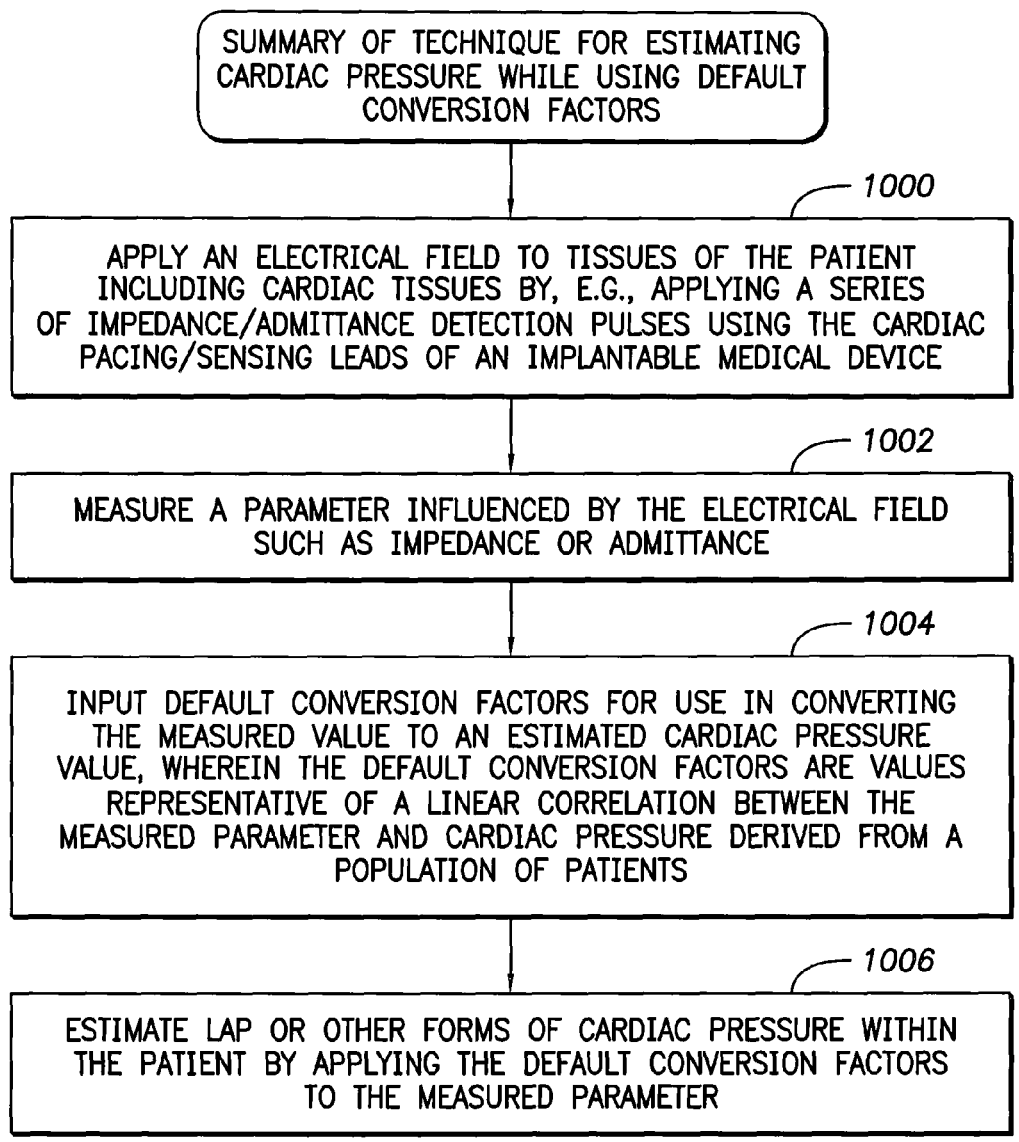
FIG. 23 is a flow diagram summarizing a technique for estimating cardiac pressure using an implantable medical device, such as the device of FIG. 1, wherein default conversion factors derived from a patient population are exploited to estimate cardiac pressure from measured electrical parameters.

FIG. 23 summarizes techniques for estimating cardiac pressure by exploiting default conversion factors, such as default values for slope and baseline derived from a population of patients. Some of the general steps of the method are similar to steps discussed above and hence will not be re-described in detail.

Beginning at step 1000, an electrical field is applied to tissues of the patient including cardiac issues by, for example, applying a series impedance or admittance detection pulses using the cardiac pacing/sensing leads of an implantable medical device. At step 1002, the device measures a parameter influenced by the electrical field, such is impedance, admittance, or conductance. At step 1004, the device inputs default conversion factors from memory for use in converting the measured value to an estimated cardiac pressure value, wherein the default conversion factors are values representative of a linear correlation between the measured parameter and cardiac pressure derived from a population of patients. For example, the default conversion factors may be slope and baseline values for converting admittance parameters measured within the patient to LAP estimates. Techniques for generating slope and baseline values based upon data collected within a population of patients is described above in connection with FIGS. 9 and 10. Note that, although the examples of FIGS. 9 and 10 pertain to the generation of conductance-based conversion factors, similar techniques may be employed for generating slope and baseline values for use with admittance or impedance values (or any other electrical parameters correlated with LAP or other forms of cardiac pressure.) At step 1006, the implanted device then estimates cardiac pressure within the patient by applying the default conversion factors to the parameter measured at step 1002, such as by applying default slope and baseline conversion factors to impedance, admittance, or conductance parameters measured within the patient.

By exploiting default conversion factors derived from a population of patients, an implantable device can perform the various cardiac pressure estimation techniques described herein without first individually calibrating the estimation procedure to the particular patient. The default slope and baseline values may be representative of different classes of patients subdivided, for example, based on age, gender or weight. The use of default conversion factors is particularly advantageous within patients who are not already known to be suffering from heart failure. Within such patients, an otherwise conventional pacemaker or ICD can be equipped with an LAP estimation system that exploits default conversion factors for the purposes of detecting the onset of heart failure based on LAP estimates. Once there is an indication of possible heart failure in the patient, suitable warning signals are generated by the device to notify the patient to consult his or her physician. At that time, the physician can then determine whether heart failure is indeed occurring and, if so, the conversion factors can then be more precisely calibrated using, e.g., invasive calibration techniques, so as to provide more accurate estimates of LAP for the purposes of tracking the progression of heart failure within the patient, titrating medications, controlling pacing therapy, etc. This procedure is shown in FIG. 24.

Figure 24:
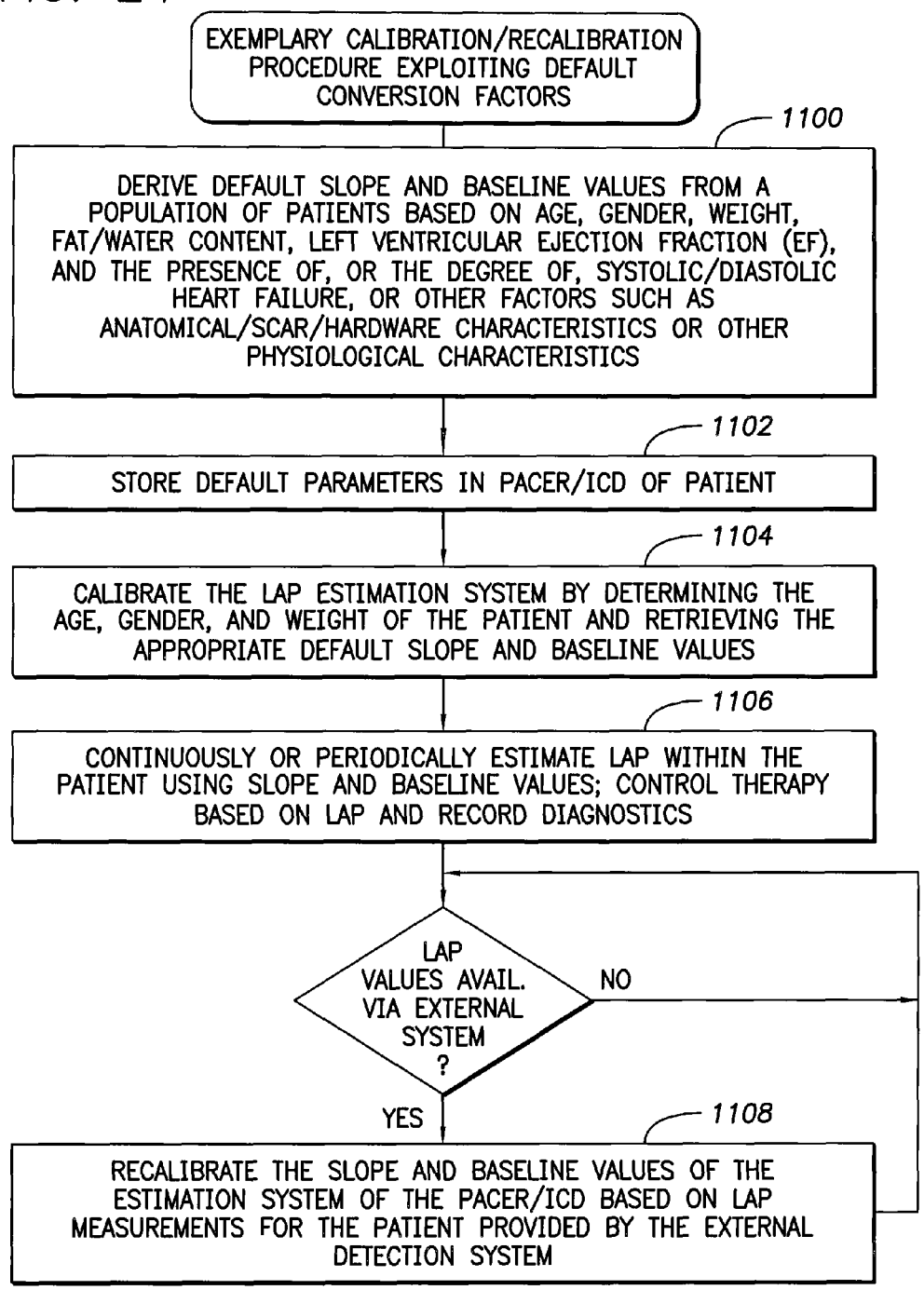
FIG. 24 is a flow diagram illustrating an exemplary technique for calibrating/recalibrating a cardiac pressure estimation system in accordance with the general technique of FIG. 23, wherein default conversion factors are initially used until more precise conversion factors can be calculated for the patient.

FIG. 24 illustrates an exemplary calibration/recalibration procedure exploiting population-based default conversion factors. At step 1100, default slope and baseline values are derived from a population of patients based on, for example, age, gender, weight or other factors. For example, various age ranges may be specified such as "less than 40 years old", "40 to 50 years old", "50 to 60 years old", etc., with separate slope and baseline values derived for those populations of patients. Likewise, separate slope and baseline values may be designated based on various weight ranges for the patients. Separate parameters are preferably also specified based on gender. Other factors may also be exploited, such as fat/water content, body surface area, left ventricular ejection fraction (EF), cardiac compliance, thoracic venous capacitance, and the presence of, or the degree of, systolic/diastolic heart failure. Patient population characteristics may also be divided into anatomical/scar/hardware characteristics and physiology characteristics.

In one example, a patient with systolic HF (Patient S) may be assigned a default slope value of 15, while a patient with diastolic HF (Patient D) may be assigned a default slope of 25. Assuming both Patient S and Patient D start with a baseline thoracic fluid volume of 2 liters and LAP 15 mmHg, and assuming both Patient S and Patient D have similar implanted devices/leads and anatomy (body size, gender, and fat/water content), then both Patient S and Patient D may have a baseline trans-thoracic impedance of 500 ohms. The initial admittance for both Patient S and Patient D is 1000/500=2.0 micro-Amp/milliVolt. The baseline for Patient S will be −15, such that LAP=2*15−15=15 mmHg. The baseline for Patient D will be −35, such that LAP=2*25−35=15 mmHg. Assuming, instead, that both Patient S and Patient D are acutely overloaded each with an additional of 0.5 liters of thoracic fluid volume, then in both Patient S and Patient D there will be an acute drop in the trans-thoracic impedance from 500 ohms to 400 ohms (admittance rises from 2.0 to 2.5). The resulting LAP will be as follows:

For Patient S: zLAP=2.5*15−15=22.5 mmHg, which is associated with no pulmonary edema because zLAP<25 mmHg.

For Patient D: zLAP=2.5*25−15=47.5 mmHg, which produced acute pulmonary congestion because zLAP>>25 mmHg.

It is known that patients with diastolic HF are much more sensitive to small fluid increases compared to patients with systolic HF that can easily tolerate a fluid increase of 0.5 liter. The equations of the above example are consistent with that observation. Note that, from a practical perspective, many of the patients that receive bi-ventricular CRT pacemakers and defibrillators (i.e. CRT-D) have similar characteristics (e.g., low EF with systolic HF), such that the population implanted with devices is somewhat more homogenous. As such, within those patients, it may conceivable to use a default slope.

At step 1102, the default parameters are stored within the pacer/ICD of the patient. At step 1104, the LAP estimation system of the pacer/ICD of a particular patient is calibrated by determining the age, gender and weight of the patient and retrieving the appropriate default slope and baseline values for the patient. For example, the age, weight and gender of the patient may be stored within the pacer/ICD during an initial programming session following device implant. The age of the patient may be updated periodically to reflect the increasing age of the patient. The weight of the patient may be updated, where needed, using a bedside monitor or other device interface to reflect any significant changes in weight. For example, the patient or his/her caregiver may be instructed to enter the patient's weight into a bedside monitor every week or month, such that the latest weight value can then be transmitted to the implantable device for use therein.

At step 1106, the pacer/ICD continuously or periodically estimates LAP within the patient using the slope and baseline values. Depending on the programming of the device, the device can then control therapy based on LAP, record diagnostics, generate warning signals, etc., as already described in connection with FIGS. 1-22. If, at any time, "true" LAP values become available via an external system, then the implantable device recalibrates the slope and baseline values, at step 1108, based on the LAP measurements provided by the external system. Such LAP measurements may be obtained, for example, using a Swan-Ganz catheter equipped with a PCWP sensor or by using other external cardiac pressure measurement systems capable of providing precise measurements of LAP.

In one example, if estimates of LAP achieved using the default conversion factors indicates possible onset of heart failure, the patient may be directed to consult his or her physician, who then uses the Swan-Ganz catheter to determine more precise values for LAP for use in recalibrating the slope and baseline values. As already explained in connection with FIGS. 1-22, such calibration techniques typically involve detection of two or more data points at widely differing LAP values by selectively exploiting the Valsalva maneuver or other suitable techniques to cause significant changes in LAP within the patient.

Thus, FIGS. 23-24 illustrate techniques for exploiting default conversion factors derived from a population of test subjects. In some cases, the default parameters may be sufficient to obtain satisfactory LAP estimates such that no further recalibration is required. Typically, however, the default parameters are only used until a more precise set of conversion factors are specified for the particular patient, either using invasive or noninvasive recalibration techniques. Also, the default parameters may be used in any circumstances where recalibration yields slope/baseline conversion factors outside a predetermined permissible range of values, so as to avoid clearly erroneous LAP estimates. Default parameters may also be employed if the recalibrated slope/baseline values yield LAP estimates outside a predetermined permissible range of pressure values. Thus, in one example, maximum and minimum permissible slope and baseline values are determined in advance for storage within the device. If the on-board recalibration system determines slope and baseline values that are outside the range, the default slope and baseline values are instead used. Suitable warning signals are generated to notify the physician that anomalous slope and baseline values were obtained with the patient. As another example, if the on-board LAP estimation system generates LAP values that are negative or exceed about 30 mmHg during a period of time when the patient is clearly not in heart failure, the slope and baseline values used to generate the LAP estimates are discarded in favor of default values. As can be appreciated, the use of default conversion factors may be appropriate in a wide range of circumstances and all such situations are not described in detail herein.

Further with regard to the use of default conversion factors, it is beneficial to ensure that the implanted medical device is well characterized in reference to their ability to accurately measure impedance (or admittance, conductance, etc.) on the bench prior to being implanted within a patient. For each device, measurements of impedance are preferably obtained on the bench over a wide range of impedance loads over the range of impedance vectors/gains of interest. For each device, trim values should be determined (Trim_Offset and Trim_Gain) so that raw impedance measurements can be adjusted to produce more accurate impedance measurements as follows:

$$Impedance = Trim\_Gain * Raw\_Impedance - Trim\_Offset.$$

The goal is to ensure that all implanted devices have minimal variability among themselves while measuring impedance, so that any variability in impedance measurements found within a group of patients will be primarily due to variation in patient characteristics (rather than due to variations in device characteristics.) This enhances the reliability of using default slope or gain values on a group of patients with similar characteristics.

Linear Correlation Between Slope and Baseline Conversion Factors

Figure 25:
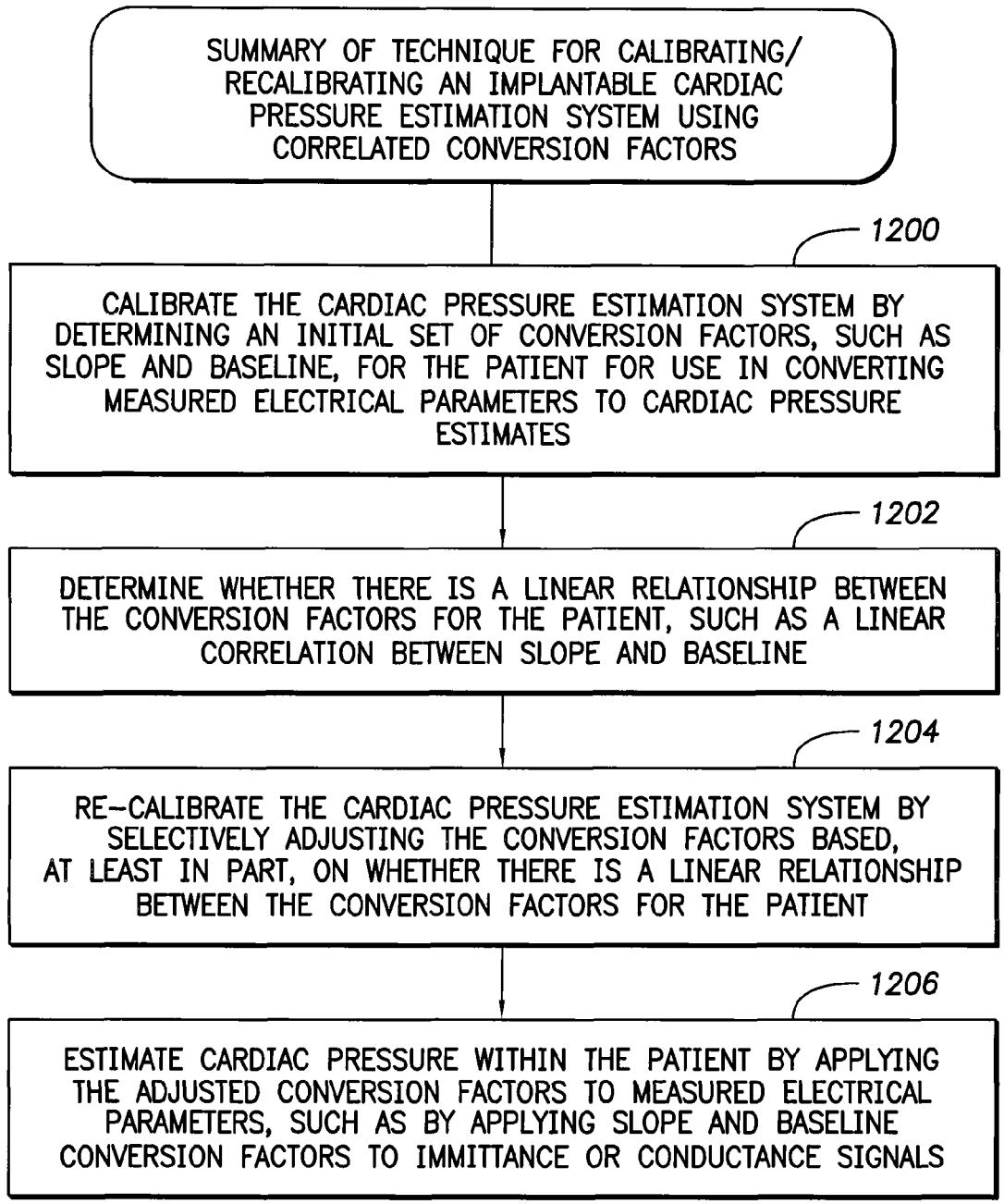
FIG. 25 is a flow diagram summarizing a technique for calibrating/recalibrating a cardiac pressure estimation system of an implantable medical device, such as the device of FIG. 1, wherein a linear relationship between conversion factors is exploited.
Figure 26:
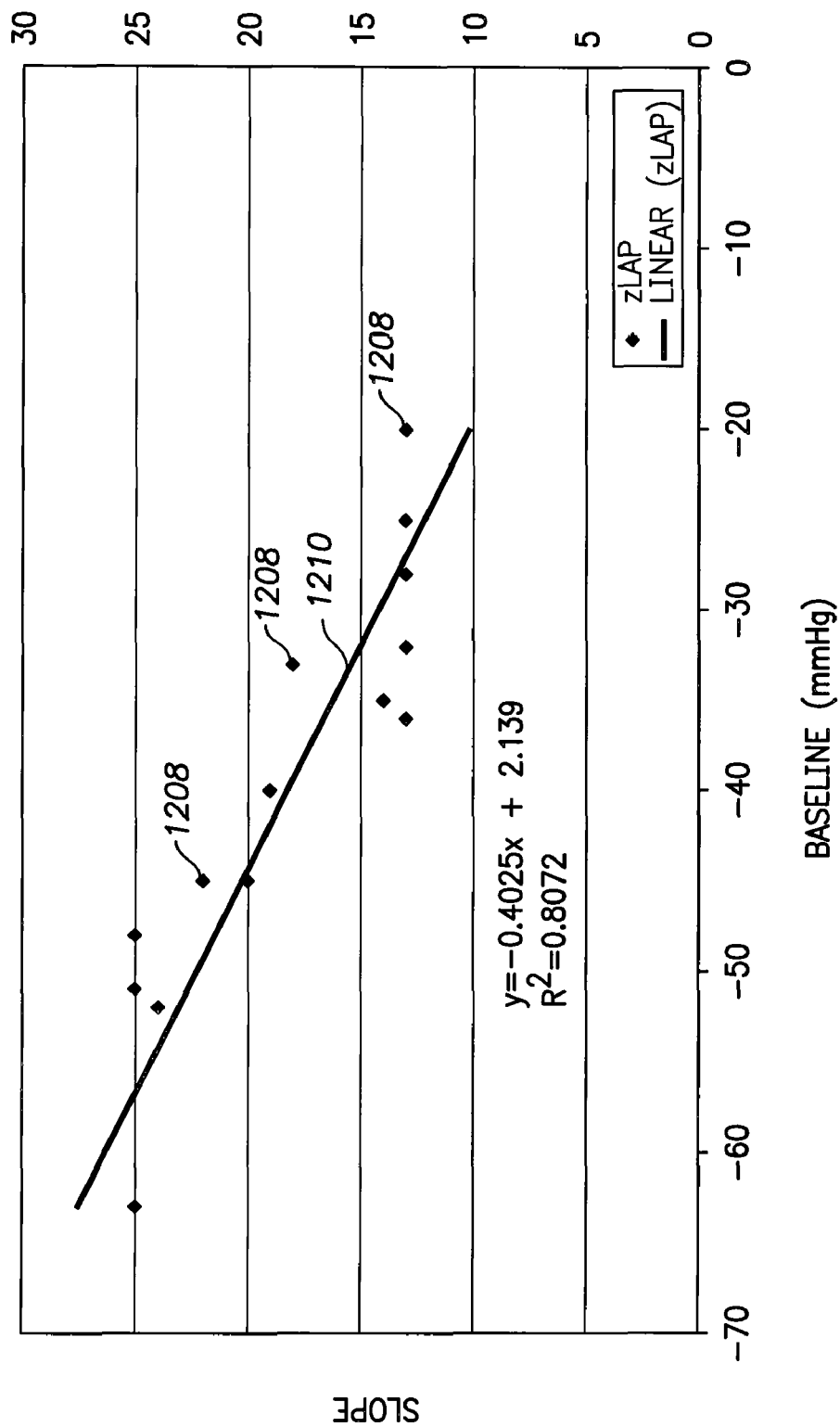
FIG. 26 is a graph illustrating exemplary slope and baseline conversion factors processed in accordance with the technique of FIG. 25, and particularly illustrating a linear correlation between slope and baseline within a test subject.
Figure 27:
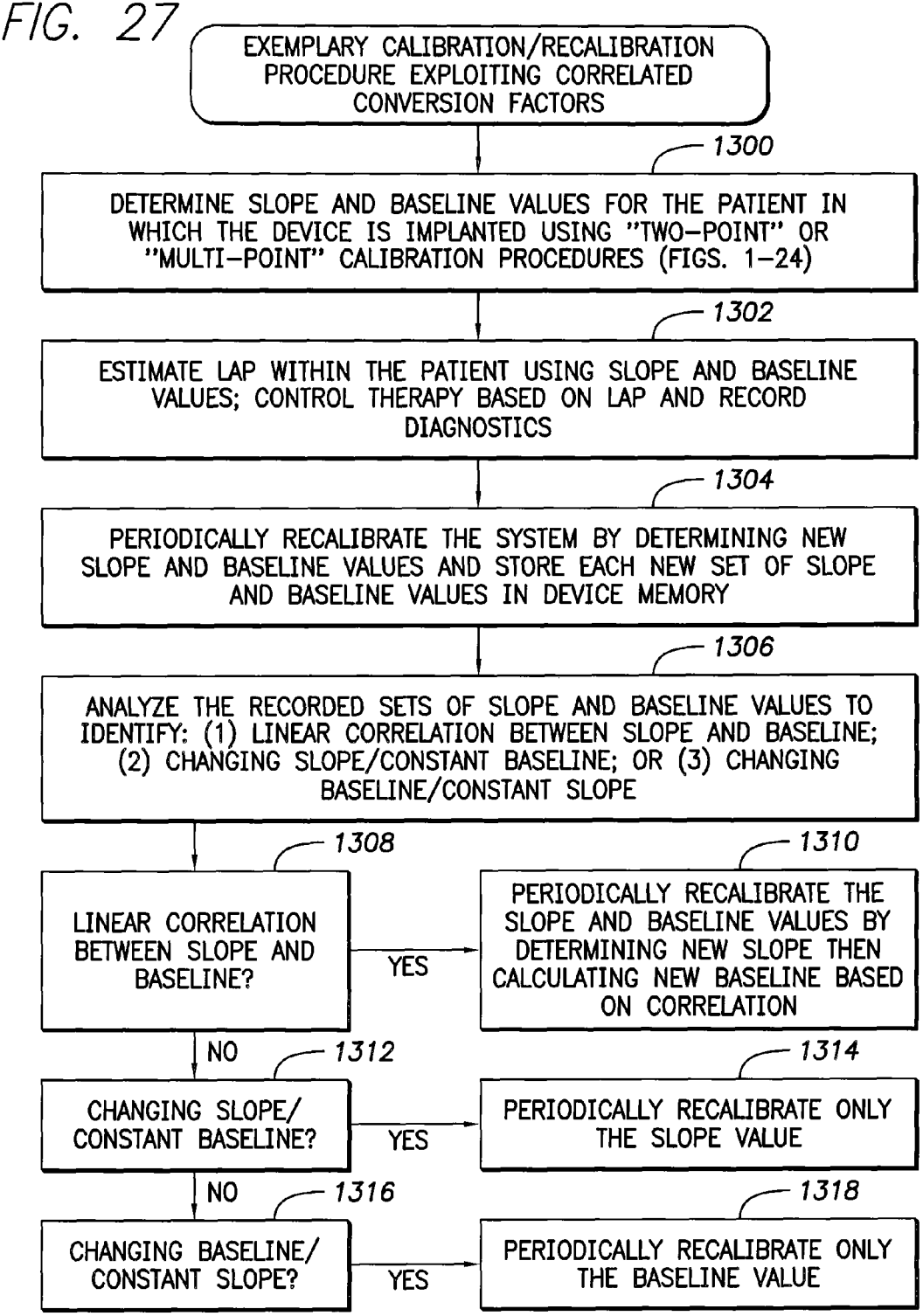
FIG. 27 is a flow diagram illustrating an exemplary technique for calibrating/recalibrating a cardiac pressure estimation system in accordance with the general technique of FIG. 25, wherein trends or correlations in slope and baseline values within a patient are exploited.

FIGS. 25-27 illustrate techniques for exploiting trends or correlations among or between the various conversion factors. In particular, it has been found that, within at least some patients, slope and baseline values are linearly correlated. Within such patients, the determination of the appropriate slope value for the patient is thereby sufficient to calculate the corresponding baseline value, or vice versa. This allows for the use of simpler and more efficient calibration/recalibration techniques. In other patients, it has been found that the baseline value does not change significantly over time, such that only the slope value need be periodically recalibrated. In still other patients, it has been found that the slope value does not change significantly over time, such that only the baseline value need be periodically recalibrated. Again, generally simpler calibration/recalibration techniques may thereby be employed, which exploit these observations.

FIG. 25 provides an overview of these trend-based techniques. Beginning at step 1200, the cardiac pressure estimation system of an implantable medical device is calibrated by determining an initial set of conversion factors, such as slope and baseline values, for the patient for use in converting measured electrical parameters, such as impedance, admittance, or conductance, to cardiac pressure estimates. Any of the various calibration procedures discussed above may be appropriate. At step 1202, a determination is made as to whether there is a linear relationship between the conversion factors for the patient, such as a linear correlation between slope and baseline. This determination may be performed by the implanted device itself, or by an external system such as an external programmer operated by a clinician. Otherwise conventional linear regression techniques may be employed to detect a linear correlation between slope and baseline. Note that, in order to determine whether there is a linear relationship between slope and baseline, a sufficient number of pairs of slope/baseline values are preferably detected for the patient. This may be achieved, for example, by recalibrating the slope and baseline values every few months and recording the latest slope/baseline values within the implantable device. As such, after a year or two, a sufficient number of the slope/baseline data points may be stored to permit a reliable determination of whether there is a linear correlation between slope and baseline within the particular patient via linear regression. Thereafter, assuming a linear correlation has been detected, more efficient recalibration techniques can then be exploited, which do not require separate determination of both slope and baseline values.

In any case, at step 1204, the cardiac pressure estimation system is then recalibrated by selectively adjusting the conversion factors based, at least in part, on whether there is a linear relationship between the conversion factors for the patient. For example, if there is a linear relationship between slope and baseline, then recalibration may be performed by exploiting a calibration technique that detects only the slope value, or only the baseline value. Given the linear relationship between the two, the other value can then be directly calculated. That is, the baseline value may be calculated from a detected slope value, or the slope value may be calculated from a detected baseline value.

As already explained, in circumstances where slope and baseline are not correlated, at least two data points are required in order to determine slope and baseline. (See, e.g., FIGS. 4-5.) The patient selectively performs the Valsalva maneuver (or other techniques for triggering changes in LAP) so that the system can obtain multiple calibration data points at both low and high LAP levels. However, in patients where slope and baseline are correlated, then, typically, only a single new data point is required to determine new slope and baseline values. For example, the recalibration system can instead obtain a single measurement at a relatively high cardiac pressure level for use in determining a new slope/baseline values. That is, in at least some cases, a single new data point may be used to determine a new slope value. The linear correlation is then exploited to calculate the new baseline value from the new slope value.

At step 1206, the cardiac pressure within the patient is then estimated by applying the adjusted conversion factors to measured electrical parameters, such as by applying be adjusted slope and baseline the conversion factors to impedance, admittance or conductance signals measured within the patient.

FIG. 26 illustrates the linear correlation between the slope and baseline for a set of test subjects. The test subjects of FIG. 26 were animal test subjects, but similar linear relationships between slope and baseline are expected to be found with at least some human patients, as well. Within FIG. 26, the individual pairs of slope/baseline data points for the test subject are identified by reference numerals 1208. Line 1210 illustrates the best fit through the data points based on the assumption of the linear relationship. FIG. 26 also provides a linear equation representing the best fit of the data, as well as the correlation factor 0.8072. Note that the linear equation of FIG. 26 (which relates slope to baseline) should not be confused with the various other linear equations described herein, which relate impedance/admittance to LAP.

Based on the linear relationship between slope and baseline, the following procedure may be used in the clinical setting, with three options for deriving the calibration coefficients BASELINE and SLOPE.

DEFINITIONS (for the purposes of this particular example):
  Z≡Impedance in ohms (Ω)
  BASELINE≡1st conversion factor in mmHg
  SLOPE≡2nd conversion factor in mmHg·mΩ
Exemplary Procedure:
  Step 1: Set BASELINE and SLOPE parameters.
  Options:
    Use defaults:
      BASELINE=−38
      SLOPE=2.139−0.4025*BASELINE=17.434
    Have user enter BASELINE and then compute SLOPE using above formula
    Have user enter both BASELINE and SLOPE
  Step 2: Compute LAP using the following formula:

$$LAP = SLOPE*1000/Z + BASELINE$$

Step 3: Plot LAP in mmHg as a function of time on one graph along with IEGM on a second graph. The scale for the LAP graph can be, e.g., from −5 mmHg to 35 mmHg.

This example assumes that impedance (Z) is measured. Corresponding equations may be provided for use with admittance or conductance. As noted above, slope may instead be referred to as gain. Baseline may instead be referred to as offset.

As explained above, the Valsalva maneuver may be used to derive the baseline value in a non-invasive manner. Once baseline is determined non-invasively, the slope value may be estimated using the above linear equation. Another option is for both the baseline and slope to be determined using a right heart catheterization, where multiple measurements of the PCWP may be obtained at various physiologic conditions (rest, Valsalva, IV nitroglycerin, and/or sustained hand-grip) with simultaneous measurements of impedance. Additionally, at the time of device implant a measurement at rest of PCWP may be used and subsequently applied to estimate the baseline under similar clinical conditions (i.e., compensated HF without symptoms). Note also that the impedance obtained during the Valsalva maneuver may also serve as a baseline reference point for determining subsequent HF exacerbation.

FIG. 27 illustrates an example wherein various trends in slope and baseline values are exploited, in addition to any possible linear correlation there between. Beginning at step 1300, slope and baseline values are determined for a patient in which an implantable medical device is installed, wherein the slope and baseline values are determined using "two-point" or "multi-point" calibration procedures, such as those described above in connection with FIGS. 1-22. That is, calibration procedures are performed which do not assume any linear correlation between slope and baseline. At step 1302, the LAP of the patient is estimated (continuously or periodically) using the slope and baseline values determined at step 1300. Therapy may also be controlled based on LAP and suitable diagnostic information may be generated. Warnings are issued, where appropriate, based on significant changes in LAP. At step 1304, the estimation system is periodically recalibrated by determining new slope and baseline values. This may be performed, e.g., once every three months, at least initially. Each new set of slope and baseline values are stored within the memory of the implanted device.

At step 1306, the recorded sets of slope and baseline values are analyzed by the device to identify (1) any linear correlation between slope and baseline; (2) any trends involving a changing slope with a constant baseline; or (3) any trends involving a changing baseline along with a constant slope. As noted, a linear correlation may be determined using linear regression. Detection of either a constant baseline or a constant slope is easily achieved by simply examining the values to determine whether the values remain within predetermined narrow ranges. If a linear correlation between slope and baseline is detected at step 1308, then, the system thereafter periodically recalibrates slope and baseline values at step 1310, by determining a new slope value, then calculating the new baseline based on the correlation. In other words, a simpler and/or more efficient recalibration procedure may be exploited which relies upon the detected correlation. If, instead, a changing slope is detected along with a constant baseline, at step 1312, then the system thereafter periodically recalibrates only the slope value, at step 1314. The baseline value need not be recalibrated because it remains substantially constant. Conversely, if a changing baseline is detected along with a constant slope, at step 1316, then the system need only recalibrate the baseline value, at step 1318, because the slope value does not change.

Steps 1310, 1314, and 1318 thus allow the system to adopt relatively simple and efficient recalibration procedures, which do not require the detection of two or more separate calibration data points at differing pressure levels, as in FIGS. 1-22. Note that, even within patients where a linear correlation is detected or where slope or baseline values do not change, it may be appropriate to at least occasionally recalibrate both slope and baseline using the recalibration procedures of FIGS. 1-22 to verify that any previously detected trends or linear correlations continue. Also note that, within at least some patients, neither the slope nor the baseline values may change appreciably over time, permitting less frequent recalibration or, in some cases, no recalibration.

Significant changes in the anatomy or physiology within the patient may affect slope and baseline values, requiring a recalibration procedure that recalculates both slope and baseline. Changes in anatomy may arise, e.g., due to changes in leads or electrode locations. Changes in physiology may arise due to the prescription of new medications or the regression or progression of illnesses. Hence, although the more efficient recalibration procedures permitted by the techniques of FIGS. 25-27 are advantageous with at least some patients, care should still be taken to ensure that the correct slope and baseline values for each particular patient is used to ensure the most accurate estimation of the LAP.

Two-Compartment Physiological Fluid State Model

Figure 28:
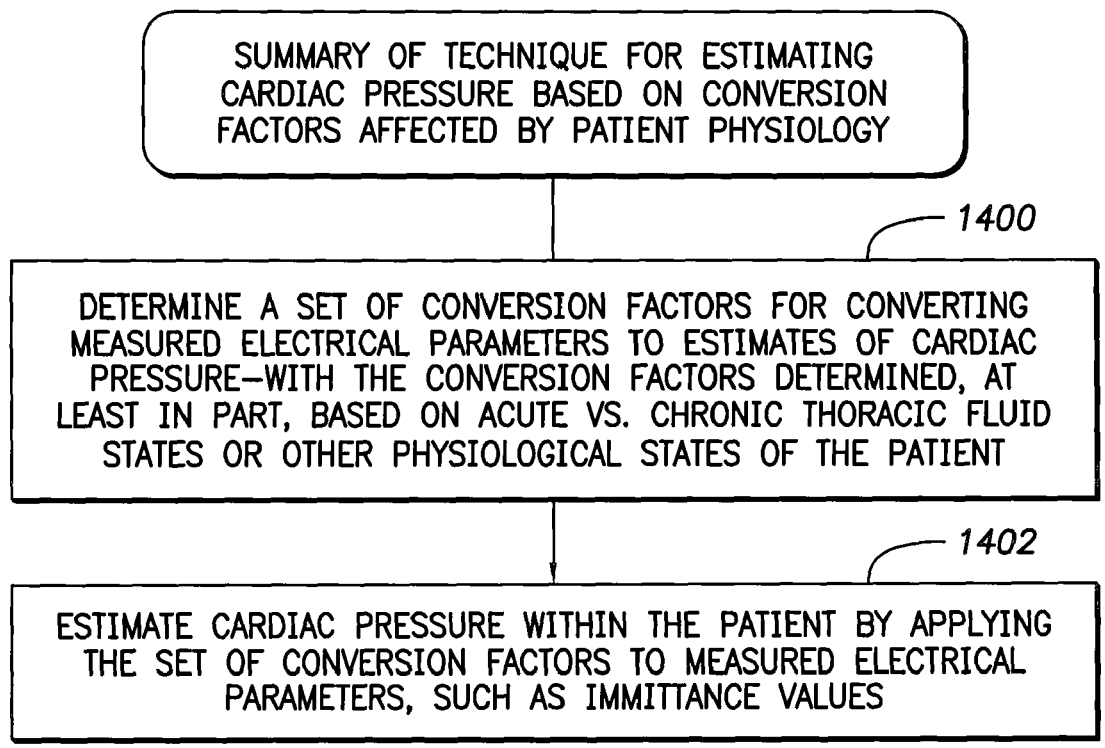
FIG. 28 is a flow diagram summarizing a technique for estimating cardiac pressure based on conversion factors affected by patient physiology for use with a cardiac pressure estimation system of an implantable medical device, such as the device of FIG. 1.

FIG. 28-35 illustrate various cardiac pressure estimation and calibration techniques that exploit different physiological states of the patient, particularly states involving different distributions of fluids within intravascular and interstitial spaces of the patient. FIG. 28 broadly summarizes these techniques. At step 1400, a set of conversion factors (such as slope and baseline) are determined for converting measured electrical parameters into estimates of cardiac pressure, wherein the conversion factors are determined, at least in part, based upon acute versus chronic thoracic fluid states, or based on other differing physiological states of the patient. At step 1402, cardiac pressure is estimated in the patient by applying the set of conversion factors to measured electrical parameters, such as by estimating LAP based on impedance, admittance or conductance values by applying an appropriate slope and baseline conversion factors. In one example, described more fully below, slope and baseline values are initially determined based on an initial acute fluid state, and then converted into slope and baseline values for use in the chronic fluid steady state. In another example, also described more fully below, slope and baseline of values are determined for both an acute initial state and a chronic physiological steady state, then the appropriate slope and baseline values are then used depending upon the current state of the patient.

Insofar as the acute and chronic fluid states are concerned, pre-clinical studies demonstrated that, although impedance measurements correlate and track well with LAP, the impedance measurements reflect more so the intra-thoracic volume rather than the measured LAP or pulmonary venous pressure. Because the intra-thoracic fluid volume is distributed within at least two-compartments (corresponding to the fast changing intra-vascular fluid compartment and the slow changing interstitial fluid compartment), measurements of impedance may reflect either an acute change occurring only in the intra-vascular fluid compartment or the chronic steady state occurring between the intra-vascular and interstitial fluid compartments once sufficient time has elapsed to permit the compartments to equilibrate. The impedance measurements may also represent a transitional state between an acute state and a chronic steady state while the intravascular and interstitial fluid compartments are equilibrating. Because the fluid volume within the intra-cellular fluid compartment remains relatively constant, it is not a contributing component to the dynamically changing thoracic fluid volume and may be lumped together with the fixed tissues and hardware residing along the impedance sensing vector. The observation that the impedance measurements reflect more so the intra-thoracic fluid volume rather than reflecting a direct measurement of the LAP or the pulmonary venous pressure was evident, for example, especially after significant fluid overload was produced following several weeks of rapid RV pacing in an ovine model. It was observed that the recovery of impedance was significantly delayed behind recovery of LAP, which is thought to be secondary to the slower absorption of fluid from the interstitial fluid compartment relative to the faster removal of fluid from the intra-vascular fluid compartment. This phenomenon is a form of hysteresis.

For the purposes of the following examples, the discussion will be described in terms of the measured intra-thoracic admittance (A0) rather than the measured impedance (Z0). Admittance is computed as 1000/Z0 and is expressed in units of microAmp/milliVolt.

Figure 29:
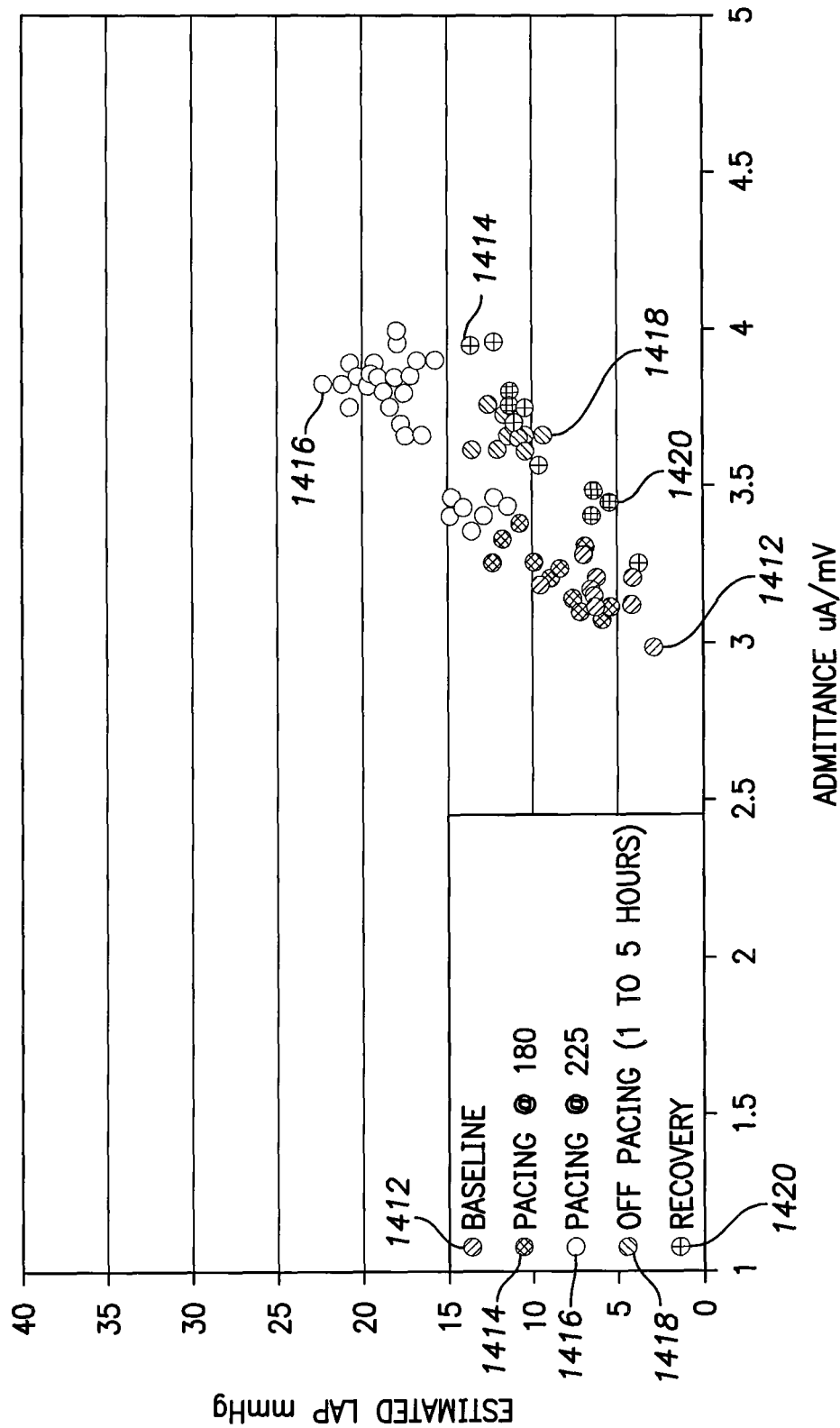
FIG. 29 is a graph illustrating trends in LAP vs. admittance arising due to changes in fluid states, which may be exploited using the technique of FIG. 28, and wherein the exemplary fluid transfer is artificially induce by variations in pacing rates.

FIG. 29 illustrates an example of hysteresis as evidenced by a pre-clinical sheep study performed in a rapid RV pacing heart failure model. During the study, baseline data was collected during the $1^{st}$ week (see reference numerals 1412), followed by two weeks of continuous rapid pacing at a rate of 180 bpm during the $2^{nd}$ week (reference numerals 1414) and at a rate of 225 bpm during the $3^{rd}$ week (reference numerals 1416). Pacing was continued at a rate of 225 bpm during the $4^{th}$ week (also represented by reference numerals 1416). However, on each successive day of the week pacing was abruptly turned off for periods ranging from 1 to 5 hours (reference numerals 1418). During the $5^{th}$ week pacing was turn off permanently and the sheep was allowed to recover (reference numerals 1420). The 1418 dots and the 1420 dots shown in FIG. 29 demonstrate a lag in the recovery of the admittance data relative to the measured LAP, representative of the hysteresis.

Figure 30:
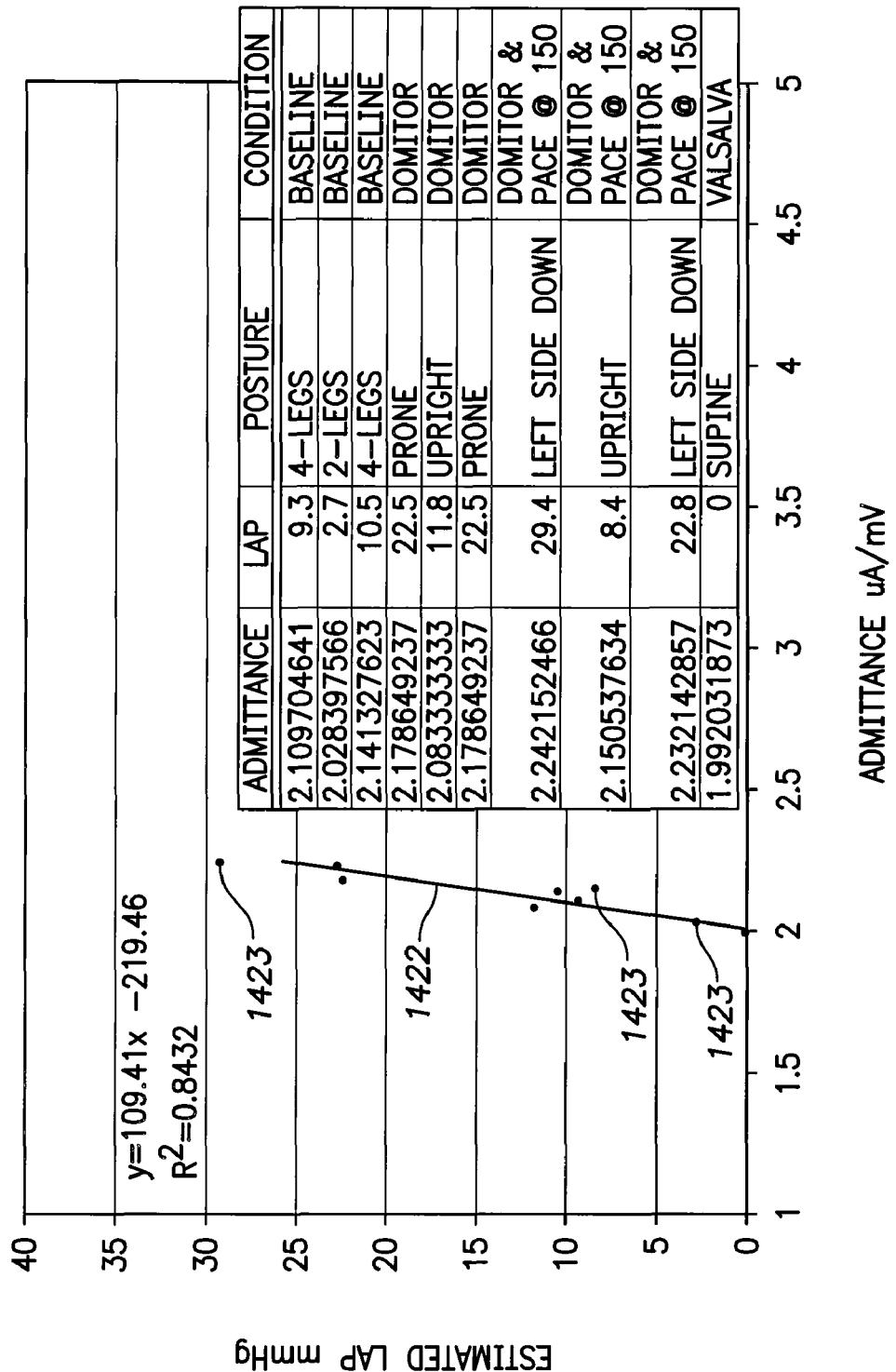
FIG. 30 is a graph illustrating trends in LAP vs. admittance arising due to changes in fluid states, which may be exploited using the technique of FIG. 28, wherein the exemplary fluid transfer is artificially induced by pharmacological agents and other factors.

FIG. 30 illustrates data from a pre-clinical study performed in a canine model. In this test, the pharmacological agent Domitor was used, which causes acute second degree heart block with severe bradycardia. (Domitor is a registered trademark of Pfizer. The generic name is medetomidine.) It can be seen from the data of FIG. 30 that, when LAP was acutely elevated rapidly following an injection with Domitor, there was only a subtle increase in admittance in response to a large change in LAP. Indeed, the admittance values of FIG. 30 change only from 2 to 2.25. In FIG. 30, the trend line through individual LAP/admittance data points is identified by reference numeral 1422. Individual data points are identified by reference numeral 1423. FIG. 30 also provides a linear equation representing the best fit of the data, as well as the $R^2$ correlation factor 0.8432.

The data in FIGS. 29-30 suggest that measurements of intra-thoracic impedance involve a two-compartment model. One compartment corresponds to the fast responding thoracic intra-vascular fluid volume (herein: Intravascular Fluid Compartment). The second compartment corresponds to the slow responding thoracic interstitial fluid volume (herein: Interstitial Fluid Compartment). Note that a third compartment corresponds to non-responding intracellular fluid volumes, which can be ignored for the purposes of the two-component model since intracellular fluid volumes remain relatively constant.

In general, water is approximately 60% of the body weight, and this water is distributed into the following components:
1) Intracellular fluid volume (40% of body weight)
2) Interstitial fluid volume (15% of body weight)
3) Intravascular fluid volume (5% of body weight)

The exact distribution of fluids within each patient may vary slightly and may be dependent on patient specific parameters such as gender and body fat content. Trans-thoracic admittance is presumed to be proportional to the intra-thoracic fluid volume. It is also presumed that the thoracic intracellular fluid volume remains relatively constant, while the thoracic intravascular and interstitial fluid volumes vary with LAP. An acute change in LAP produces a fast change in the Intravascular Fluid Compartment, while producing a slower change in the Interstitial Fluid Compartment.

In general, the techniques of FIGS. 28-35 exploit the recognition that conversion factors appropriate for use while patients are undergoing an acute physiologic maneuver (i.e., Valsalva maneuver) should not be used within patients who remain within a steady chronic physiologic state due to differences in the equilibration of fluids between the intravascular and the interstitial fluid compartments. During the day, while a patient is upright, fluids tend to pool in the lower extremities and may even produce peripheral edema (i.e. leakage of fluids from the intravascular to the interstitial space within the lower extremities). At night, or at other times while the patient is resting in a supine/prone/lateral decubitus position for an extended period of time, fluids migrate to the central venous system within the thorax and eventually equilibrate with and enter the interstitial space of the thorax. As such, impedance and admittance values measured along a sensing vector within the thorax of the patient will typically differ depending upon whether the values are measured during an acute initial state (i.e., while the patient is acutely transitioning or immediately following a transition between physiologic states) or during a chronic steady state (i.e., after sufficient amount of time elapsed to permit the intra-vascular and interstitial fluid compartments to equilibrate). Hence, conversion factors for use in converting the impedance and admittance values to estimates of LAP are likewise different depending upon the state of the patient and the appropriate conversion factors should be used.

Figure 31:
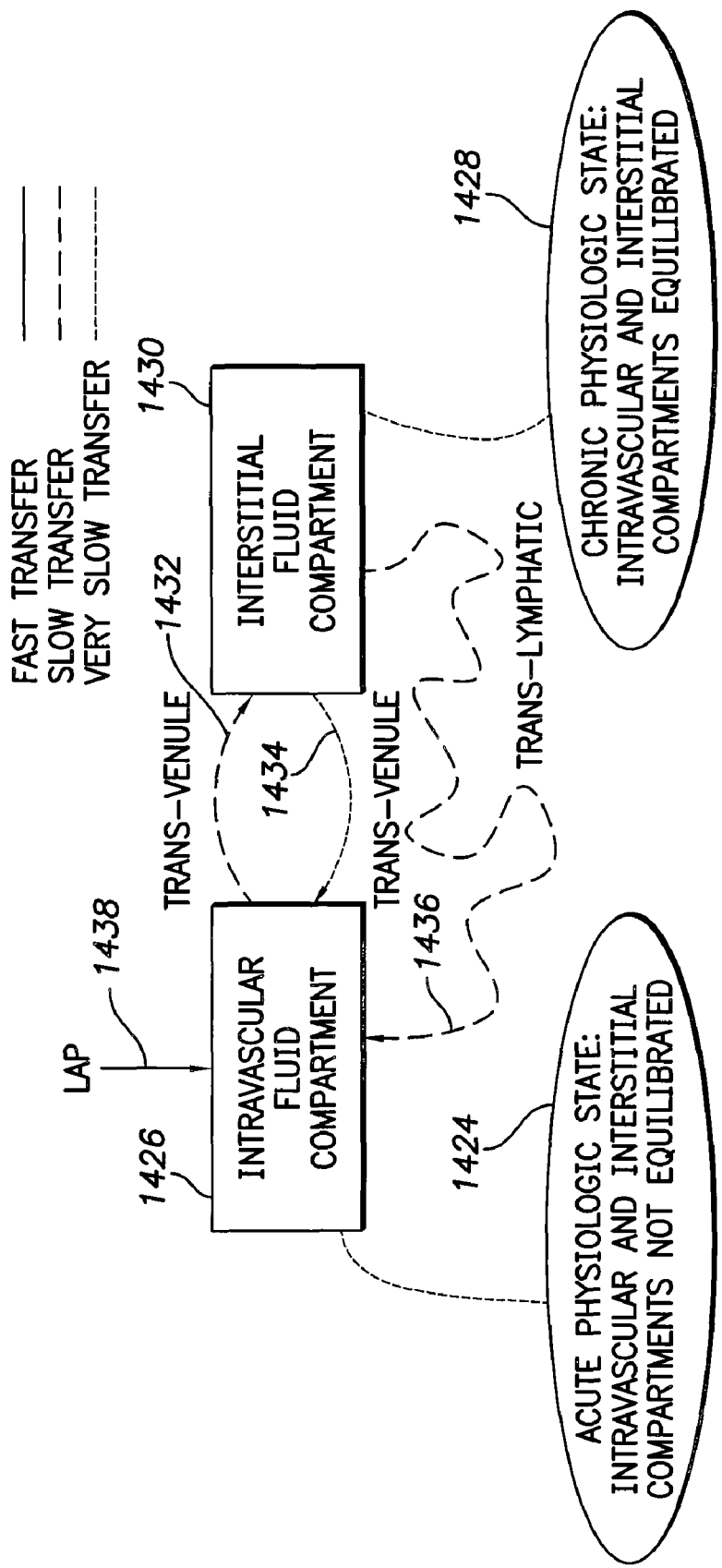
FIG. 31 is a state diagram illustrating acute and chronic physiologic fluid states processed in accordance with the general technique of FIG. 28, as well as exemplary fluid transfer processes between intravascular and interstitial fluid spaces.

FIG. 31 illustrates the acute physiological state 1424 wherein the fluids may either rapidly accumulate within the intravascular space of the thorax or rapidly be removed from the intravascular space within the thorax, i.e. the intravascular and interstitial fluid compartments are not equilibrated. The intravascular spaces are illustrated by way of intravascular fluid compartment 1426. The chronic physiological state 1428 is illustrated wherein a sufficient amount of time has permitted the fluids within the intravascular and interstitial fluid compartments to equilibrate. The interstitial spaces are illustrated by way of interstitial fluid compartment block 1430. Also shown in FIG. 31 are various fluid transference pathways including a trans-venule pathway 1432 from the intravascular spaces to the interstitial spaces, a trans-venule pathway 1434 from the interstitial spaces to the intravascular spaces and a trans-lymphatic pathway 1436 from the interstitial spaces to the intravascular spaces. Transference from intravascular to interstitial spaces is faster than the reverse trans-venule transfer for interstitial to intravascular spaces. The trans-lymphatic transference is still slower. In contrast, an increase in LAP reflects a very fast increase in fluids within the intravascular spaces, as indicated by arrow 1438.

For example, a sudden rise in LAP from 10 mmHg to 25 mmHg may reflect a fast increase in the intravascular fluid volume, which will subsequently be followed by a more gradual increase in the interstitial fluid volume once the intravascular and interstitial fluid compartments have had sufficient time to equilibrate. After the LAP has been significantly elevated (>25 mmHg) for a prolonged period of time and is rapidly reduced back to 10 mmHg, there is an associated rapid decrease in the intravascular fluid volume followed by a much slower decrease in the interstitial fluid compartment. The return of fluid from the interstitial fluid compartment to the intravascular fluid compartment is significantly slower and occurs across venules and lymphatic channels.

The two-compartment model can be exploited to derive the appropriate conversion factors (slope, baseline) needed to compute LAP from the impedance data. The following general equations are used to derive the slope and baseline:

$$\text{SLOPE} = (LAP_2 - LAP_1)/(A_2 - A_1) = \Delta LAP/\Delta A$$

$$\text{BASELINE} = LAP_1 - \text{SLOPE} \cdot A_1$$

where $LAP_1$ and $A_1$ are the LAP and admittance measured at one physiologic state, and $LAP_2$ and $A_2$ are the LAP and admittance measured at another physiologic state.

During an acute calibration procedure, a perturbation is produced such that LAP is acutely changed. Examples of techniques to produce such a perturbation include:
Physiologic Maneuvers:
Valsalva
Change in posture from supine to upright standing position
Isometric muscle contraction using bilateral sustained hand-grip exercise
Elevation of lower extremities above heart level
Pharmacologic Maneuvers:
Injection of intravenous vasodilator (e.g. nitroglycerin)
Injection of intravenous pressor (e.g., phenylepherine)
Injection of inotrope (e.g., dobutamine)
Pacing Maneuver:
Rapid atrial or ventricular pacing
Rhythm Disturbance:
Inducing atrial fibrillation
Inducing ventricular fibrillation It is believed that an acute change in LAP results in a fast acute change in the thoracic Intravascular Fluid Compartment volume followed by a more gradual change in the thoracic Interstitial Fluid Compartment volume. It is also believed that, during such an acute change in LAP, the measured change in admittance ($\Delta A$) corresponds to an acute change in the thoracic Intravascular Fluid Compartment volume with no immediate change occurring in the thoracic Interstitial Fluid Compartment volume.

Accordingly, in order to predict the change that would ultimately occur in both the Intravascular and Interstitial Fluid Compartments, an adjustment factor (such as 4.0) can be applied to the measured change in admittance ($\Delta A$) to account for the total change occurring in the fluid volume in both compartments. The factor of 4.0 was chosen based on the approximate known ratio of the total fluid volume in both compartments to the fluid volume in the intravascular compartment. Preferably, a unique adjustment factor is determined for each individual patient. This may be achieved by separately determining acute slope values and chronic slope values so that the ratio therebetween may be calculated. Such adjustment factors are expected to be somewhere in the range of 3-5.

Figure 32:
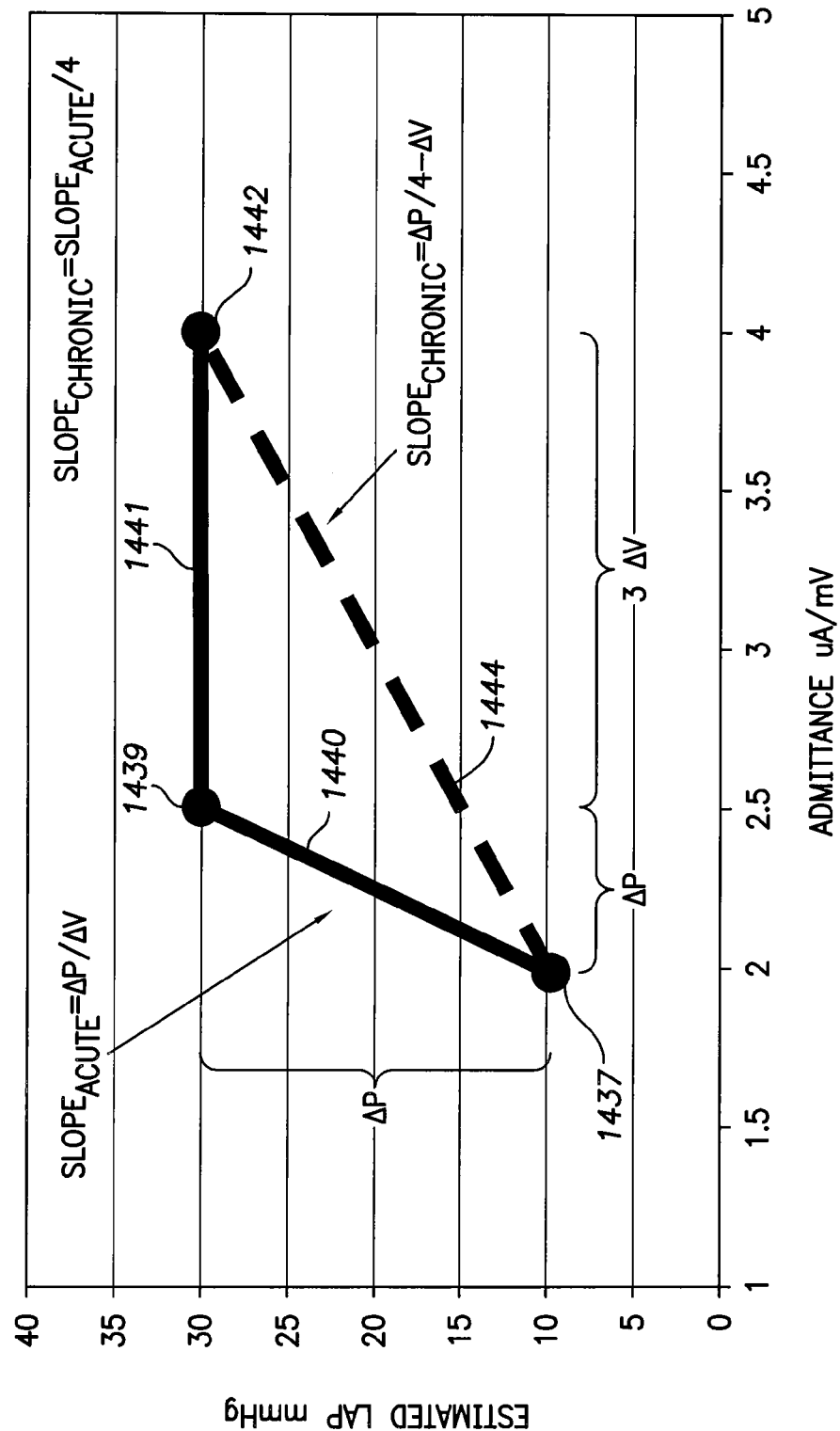
FIG. 32 is a graph illustrating trends in LAP vs. admittance arising due to changes in fluid states from chronic to acute states due to the fluid transfer processes of FIG. 29, and particularly illustrating an adjustment factor for converting acute slope values to chronic slope values.

FIG. 32 graphically illustrates the source of the adjustment factor. That is, FIG. 32 illustrates a set of hypothetical measurements obtained at two physiologic states. In this example, LAP is acutely increased from 10 mmHg to 30 mmHg (along line 1440), causing an acute change in the admittance from 2.0 μA/mV to 2.5 μA/mV. It is believed that, if this elevation in LAP to 30 mmHg was sustained for a prolonged period of time, there would be a gradual increase in the thoracic interstitial fluid volume, ultimately reaching a steady state in which three times the intravascular fluid volume would be added to the interstitial fluid volume (along line 1441). FIG. 32 also shows how the chronic state slope can be computed from the slopes of lines 1440 and 1441.

More specifically, a first data point 1437 is indicative of the initial fluid state while LAP is low, as may be obtained when the patient is standing upright just prior to dinner time. A second data point 1439 is indicative of the acute fluid state where LAP is relatively high, such as following the ingestion of a large salt/fluid intake during dinner and after lying in bed in the supine position in order to go to sleep. Based on these two data points, an acute slope value is determined, which is represented by way of line 1440. The acute slope value is representative of the difference in pressure divided by the difference in volume, as reflected by differences in admittance, between data points 1437 and 1439.

Data point 1442 represents LAP/admittance while the patient is in a subsequent chronic state wherein fluids have transferred into the interstitial spaces of thorax after a sufficient amount of time has permitted the intra-vascular and interstitial fluid compartments to equilibrate. The process by which fluids transfer from the intravascular spaces to the interstitial spaces affects the admittance value that corresponds to that LAP value. As such, it is desirable to calculate the appropriate slope value for use in the chronic steady state. As shown, the chronic state slope represents the slope of the line 1444, which interconnects data points 1437 and 1442. This chronic slope value may be estimated by applying the aforementioned adjustment factor to the acute state slope value. In this example, the adjustment factor is 4.0. As such, once slope is calculated for the acute state, a corresponding slope for the chronic state may be estimated merely by dividing the acute slope by 4.0.

Figure 33:
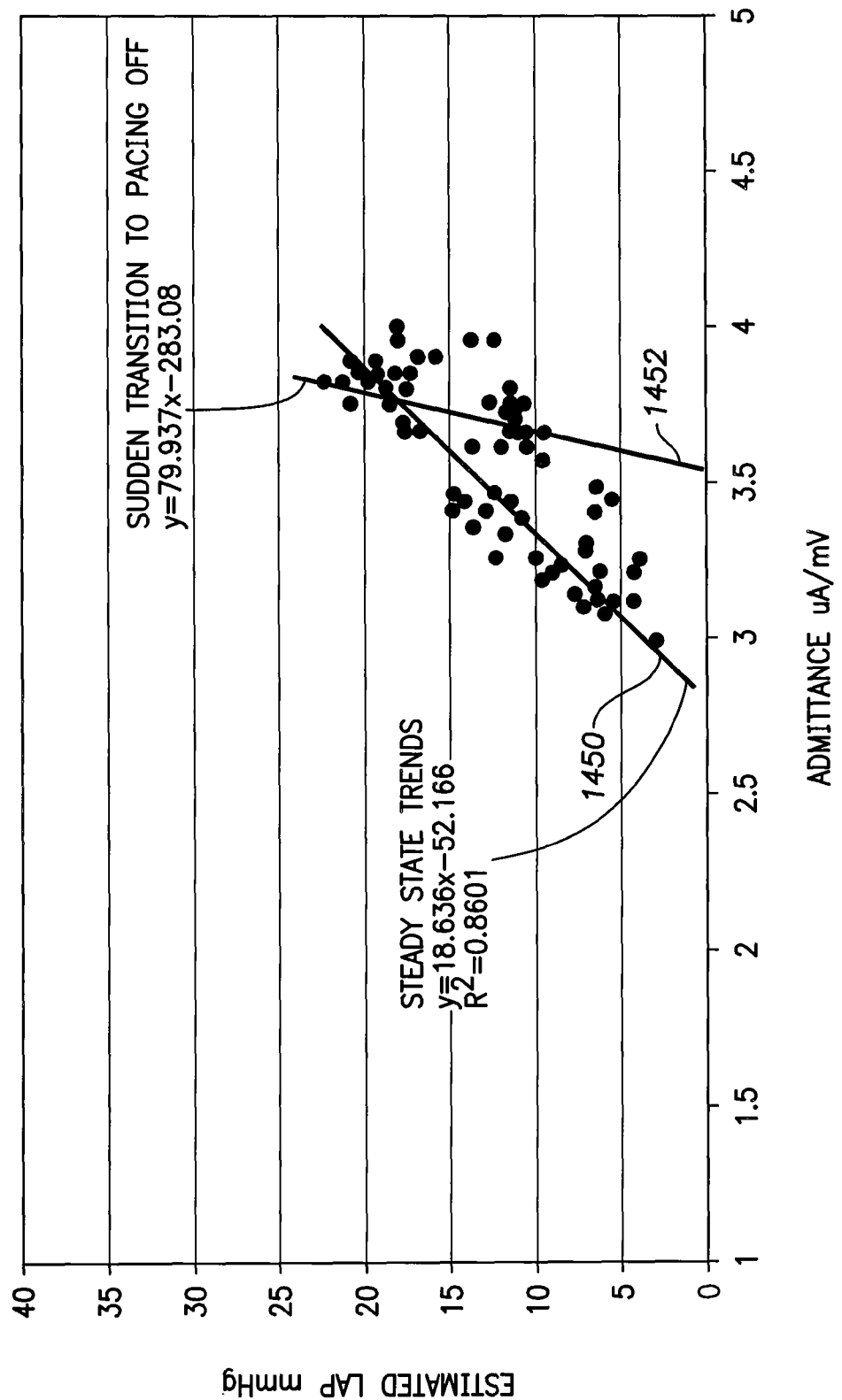
FIG. 33 is a graph illustrating trends in LAP vs. admittance arising due to changes in fluid states from chronic to acute states due to the fluid transfer processes of FIG. 29, contrasting steady state trends against artificially induced trends.

FIG. 33 further illustrates differences between acute and chronic fluid states. More specifically, the data of FIG. 29 was again plotted. In this example, however, a linear regression was performed using the data points acquired during the first three weeks when rapid pacing was turned on and gradually produced an increase in LAP. The linear repression of this data is represented by line 1450. This first trend line generally corresponds to "steady state" trends, since changes in LAP were gradual. The slope of line 1450 also generally corresponds to the chronic state slope. In addition, a second line 1452 was formed by taking the data points that occurred just before and after abruptly turning off the rapid pacing. That is, line 1452 was formed by drawing a line between a data point (not separately shown) corresponding to the average of all the data points that occurred just before turning pacing off and another data point (also not separately shown) corresponding to the average of all the data points that occurred immediately after turning pacing off. This second trend line generally corresponds to the acute state, since changes in LAP were quick. As can be seen, the two trend lines, 1450 and 1452 have significantly different slopes. The slope of line 1450 is about 80. The slope of line 1452 is about 19. That is, the two slopes differ by a factor of about 4.

Figure 34:
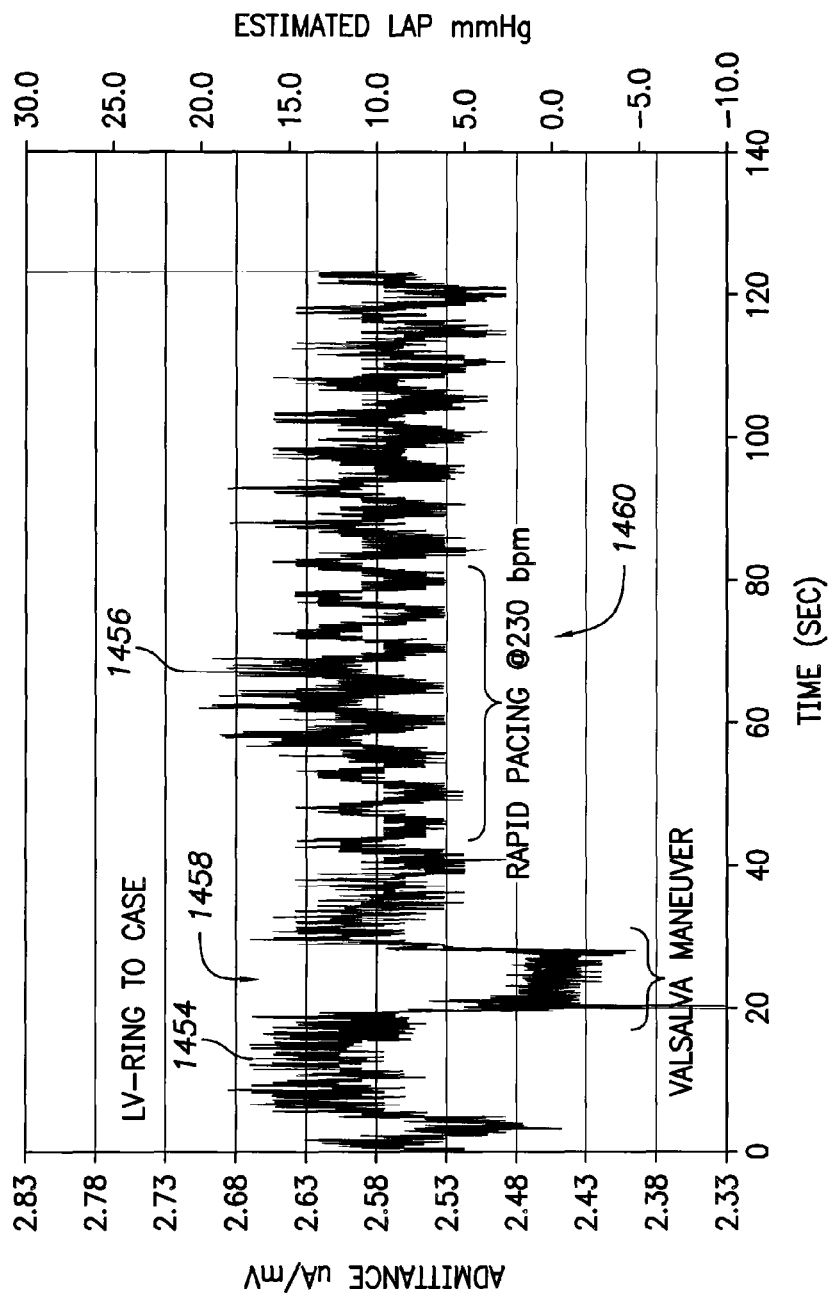
FIG. 34 is a graph illustrating changes over time in LAP and admittance arising due to changes in fluid states from chronic to acute states due to the fluid transfer processes of FIG. 29, and particularly illustrating the affect of the Valsalva maneuver and rapid pacing on both LAP and admittance.

FIG. 34 illustrates an example of how this approach can be used to calibrate the conversion factors based on data obtained using a Valsalva maneuver. In this example, simultaneous measurements are shown for the admittance (light lines 1456) and LAP (dark lines 1458) derived from an animal test subject. A Valsalva maneuver is performed during time 1458, which caused a significant drop in LAP and a corresponding significant drop in admittance. Given the significant changes in LAP brought on by the Valsalva maneuver, the test subject is therefore within the acute state. (Note that this graph also shows a subsequent period of rapid pacing, during time 1460, which caused an increase in LAR. For the purposes of calculating a chronic-state slope value from an acute-state slope value, rapid pacing is not required.)

Prior to the Valsalva maneuver, the initial average LAP is about 9 mmHg. During the Valsalva maneuver, however, LAP drops to an effective LAP of 0 mmHg. The initial admittance is about 2.6 µA/mV and during the Valsalva maneuver admittance decreases to 2.45 µA/mV. Hence, the acute-state slope is $$\text{Slope}_{acute}=9 \text{ mmHg}/(0.15)=60$$

In order to compute the chronic-state slope, the adjustment factor of 4.0 is used. That is, the general slope formula, ($\Delta P/\Delta A$), is used to obtain the following result:

$$\text{Slope}_{chronic}=\text{Slope}_{acute}/4=15$$

The chronic-state baseline is subsequently computed as follows:

$$\text{Baseline}=9-15\cdot 2.6=-30$$

The final equation for estimating LAP in this example is:

$$LAP=15\cdot(1000/Z0)-30$$

Figure 35:
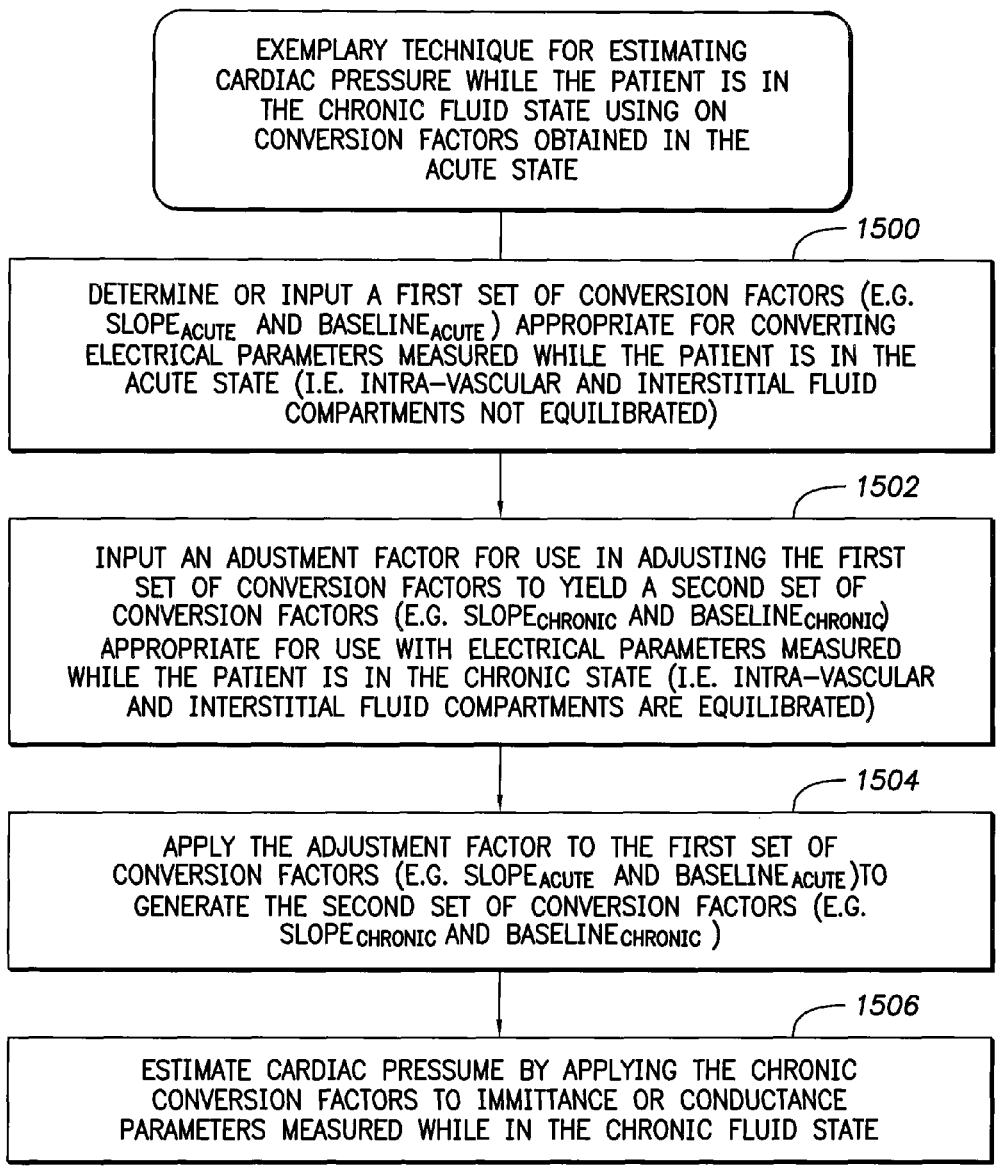
FIG. 35 is a flow diagram illustrating an exemplary technique for calibrating a cardiac pressure estimation system in accordance with the general technique of FIG. 28, wherein acute conversion factors are adjusted to yield chronic conversion factors.

FIG. 35 summarizes the technique wherein conversion factors are initially determined while the patient is in the acute state, then converted for use in the chronic state by applying the adjustment factors. This technique allows chronic state conversion factors to be obtained without requiring the patient to undergo a prolonged calibration procedure where the patient must wait to reach the chronic steady state.

Beginning at step 1500, a first set of conversion factors are determined or input that are appropriate for converting electrical parameters measured while the patient is in the acute state. The conversion factors may be the aforementioned acute-state slope and baseline values. The acute state may be achieved by having the patient stand quickly to cause a transient perturbation. The Valsalva maneuver may be exploited to provide a data point where the effective LAP is near zero. At step 1502, the aforementioned adjustment factor is input for adjusting the first set of conversion factors to yield the second set of conversion factors appropriate for use with electrical parameters measured while the patient is in the chronic steady state. The chronic state occurs once a sufficient amount of time has elapsed to permit the intra-vascular and interstitial fluid compartments to equilibrate, as would occur while the patient is inactive and has been sleeping for awhile in the prone/supine position. At step 1504, the adjustment factor is applied to the acute state conversion factors to generate the chronic state conversion factors. At step 1506, LAP is then estimated within the patient by applying the chronic conversion factors to impedance, admittance or conductance parameters measured while the patient is in the chronic fluid state.

With this technique, calibration factors can be relatively easily obtained within a clinician's office while the patient is in the acute physiological state. Thereafter, the adjustment factor is applied to convert these parameters for use in the chronic state. As such, calibration is more easily achieved since the patient does not need to wait to reach the chronic steady state while in the clinician's office in order to obtain calibration data appropriate for the chronic state.

Figure 36:
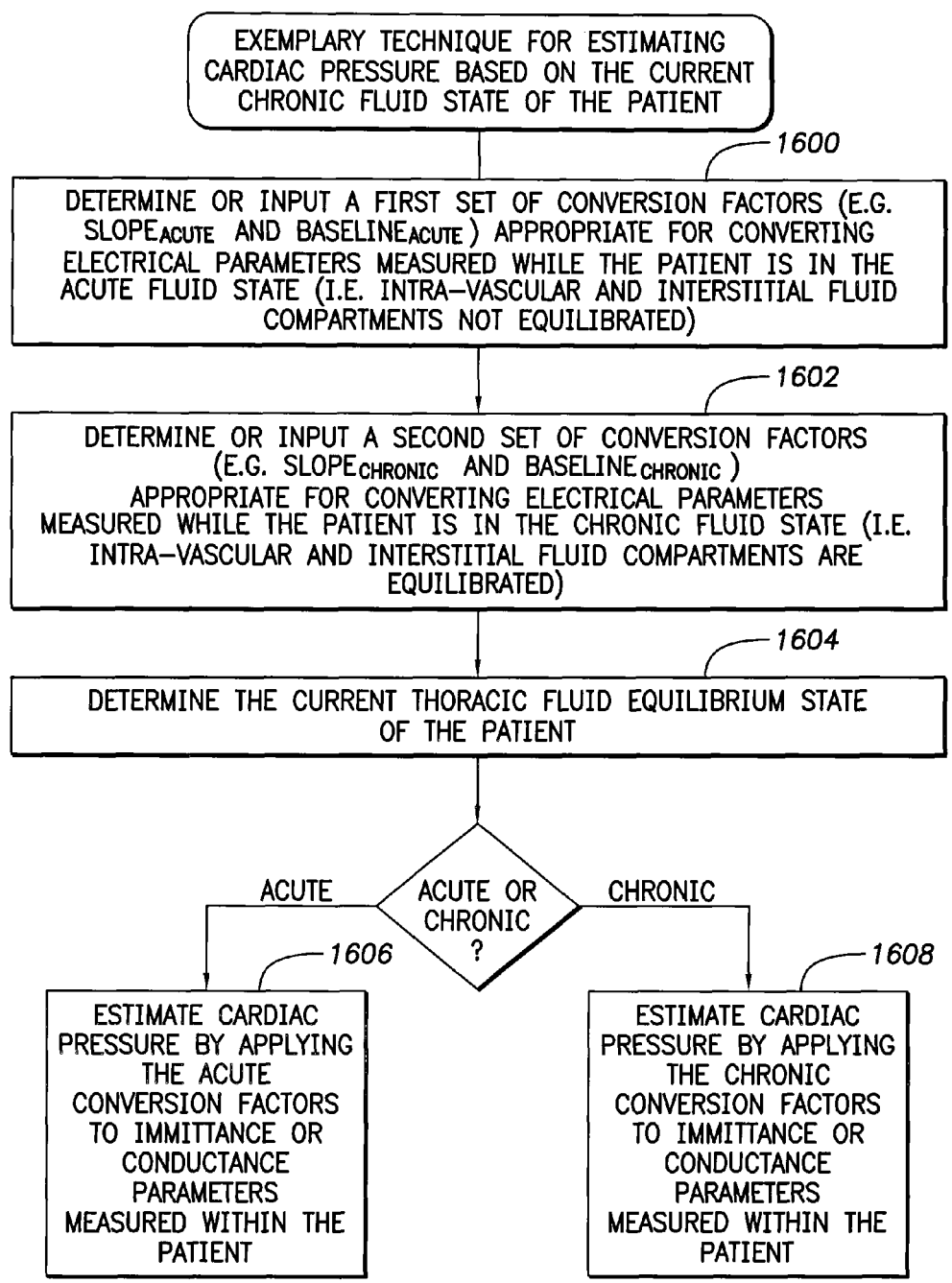
FIG. 36 is a flow diagram illustrating an exemplary technique for estimating a cardiac pressure in accordance with the general technique of FIG. 28, wherein the device determines the current thoracic fluid state and applies the appropriate conversion factors.

FIG. 36 illustrates an alternative example wherein both acute and chronic state conversion factors are determined in advance. The current state of the patient is detected so that the appropriate conversion factors can then be used. In other words, rather than determining chronic state conversion factors from acute state conversion factors as in FIG. 35, the technique of FIG. 36 initially determines both, then applies the appropriate set of conversion factors depending upon the current physiological state of patient.

Beginning at step 1600, a set of acute conversion factors are determined or input that are appropriate for converting electrical parameters measured while the patient is in the acute fluid state. At step 1602, a set of chronic conversion factors are determined or input that are appropriate for converting electrical parameters measured while the patient is in the chronic fluid state. Then, at step 1604, the current thoracic fluid equilibrium state of the patient is determined. This may be performed by using an activity sensor to determine the current level of activity in the patient or a posture sensor to detect changes in posture. If the patient has been inactive for an hour or two or even four, the patient may be presumed to be within the chronic state. If the patient has just made a significant change in posture, the patient may be presumed to be in the acute state. A posture sensor may also be employed to verify that the patient is lying down (e.g. prone or supine) while in the chronic state. Patients may have different rates in which they reach the chronic steady state, and for each patient a unique set of parameters may be programmed for use when determining whether the chronic steady state has been reached. In any case, assuming that the patient is in the acute physiological fluid state, then step 1606 is performed wherein LAP is estimated by applying the acute conversion factors to impedance, admittance or conductance parameters measured in the patient. Conversely, if the patient is in the chronic state, then step 1608 is instead performed wherein LAP is estimated by applying the chronic state conversion factors to electrical parameters measured within the patient.

In this manner, the LAP estimation system of the implanted device can make use of the appropriate conversion factors depending upon the current physiological state of the patient. As can be appreciated, in some examples, further physiological states may be ascertained and additional sets of conversion factors may be generated, appropriate for those states. For example, rather than merely defining an acute fluid state and a chronic fluid state, a variety of intermediate/transitional fluidic states could potentially be defined, with differing slope and baseline parameters determined for use in each state, representative, e.g., of differing degrees of equilibrium.

These intermediate states may further be modeled by using a set of time-dependent conversion factors where the time-dependent variable (t) is reset to zero whenever a transition is made into the new physiologic state, as detected, e.g. using a posture or activity sensor. More specifically, the following equation may be used to determine the time-dependent slope:

$$Slope_t = Slope_{chronic} \cdot (1 + 3 \cdot 2^{-t/\tau})$$

where
$\tau$=half-life time constant
t=elapsed time following transition from one physiologic state to another.
The new Baseline will subsequently be computed using the following formula:

$$Baseline_t = LAP_1 - Slope_t \cdot Y_1$$

where $LAP_1$ and $Y_1$ represent the reference LAP and admittance values corresponding to the original state from which the patient is transitioning. Hence, the use of time-dependent conversion factors allows the device to gradually and/or exponentially adjust slope values between $Slope_{acute}$ values and $Slope_{chronic}$ values, or vice versa. In one specific example, $Slope_{acute}$ may be 113.4 and $Slope_{chronic}$ may be 28.35.

Also, in one particular example, wherein the patient transitions between a supine state ($S_0$) having admittance $Y_0$ and $LAP_0$, and a standing state ($S_1$) having admittance $Y_1$ and $LAP_1$, the following equations may be used to calculate zLAP, during transitions there-between:

$$zLAP_0 = Slope_t^* (Y_t - Y_1) + LAP_1$$

and $$zLAP_1 = Slope_t^* (Y_t - Y_0) + LAP_0.$$

Figure 37:
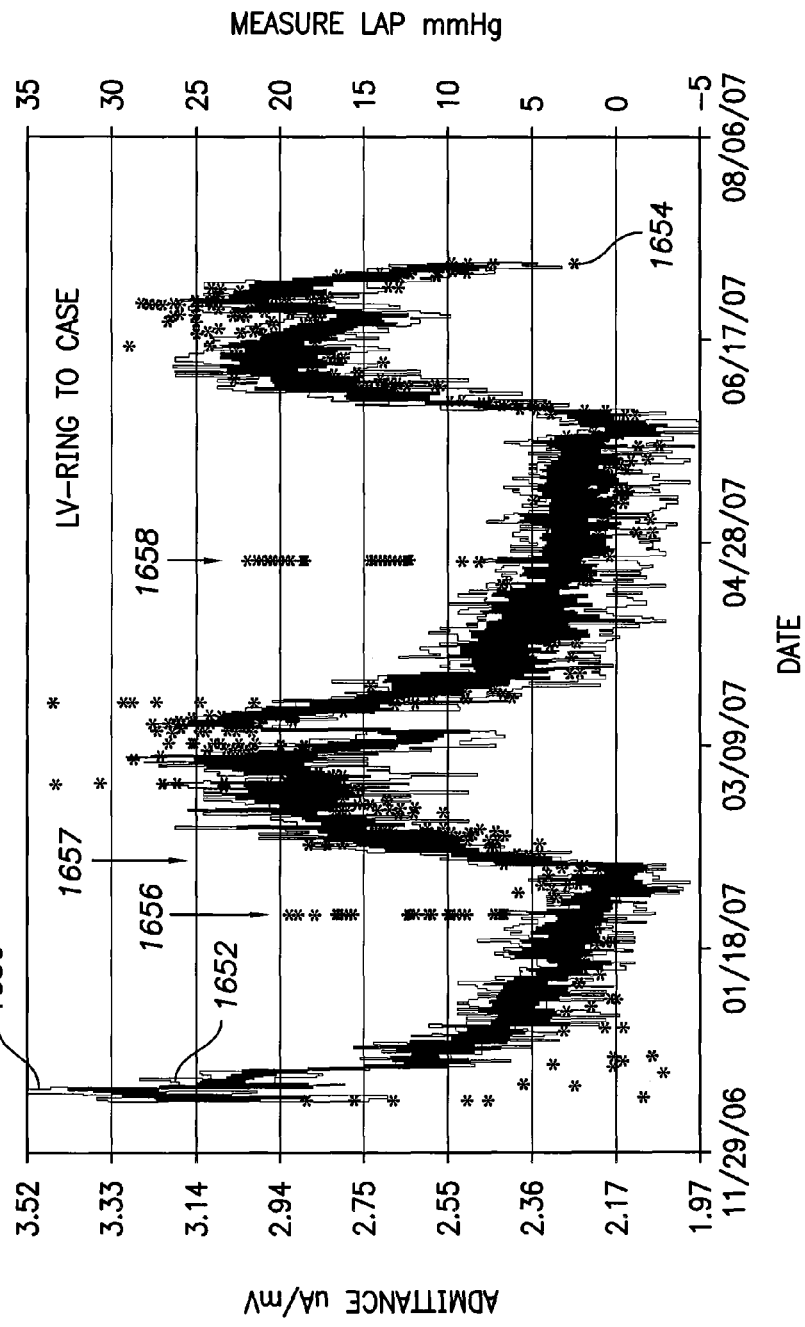
FIG. 37 is a graph illustrating increases in LAP and admittance within an animal test subject, which may be detected using the techniques of FIGS. 35-36, and particularly illustrating the affect of rapid pacing on both LAP and admittance.

FIG. 37 further illustrates LAP changes brought on by acute and chronic perturbations of fluid states within the test subject. The graph illustrates admittance 1650 as well as a six-point moving average of admittance 1652. LAP was measured with a LAP sensor implanted within the left atrium. The measured LAP is shown by way of dots 1654. The Admittance and LAP scales were adjusted using the linear regression equation shown in the bottom of the figure. A first perturbation was induced at time 1656 due to a short burst (~30 seconds) of rapid ventricular pacing to emulate heart failure. The LAP spiked at that time to almost 20 mmHg due to an acute intra-vascular fluid change. The measured admittance, however, did not demonstrate any significant simultaneous acute change. A second perturbation was subsequently initiated at point 1657 (i.e. at date Feb. 8, 2007) using repeat rapid ventricular pacing. However, during this second perturbation rapid ventricular pacing was sustained chronically for ~5 weeks until symptoms of heart failure developed with LAP>25 mmHg. During this second perturbation there was a sufficient amount of time to permit the intra-vascular and interstitial fluid compartments to equilibrate, such that both LAP and admittance increased simultaneously.

The figure thus illustrates how acute perturbations can cause significantly spikes in the measured LAP, which may not immediately be detected in the measured admittance data. If the system had instead been programmed to detect the acute state, a different set of conversion factors could have been used during the acute perturbations, which may have been able to detect more subtle changes in the admittance data. Although the data of FIG. 37 is from a canine test subject wherein acute perturbations were induced via rapid ventricular pacing, similar changes in admittance measured within human patients are anticipated to occur during an acute fluid overload which may be appropriately detected by employing the appropriate conversion factors for the acute state of the patient.

Invasive Calibration/Noninvasive Recalibration Procedures

Figure 38:
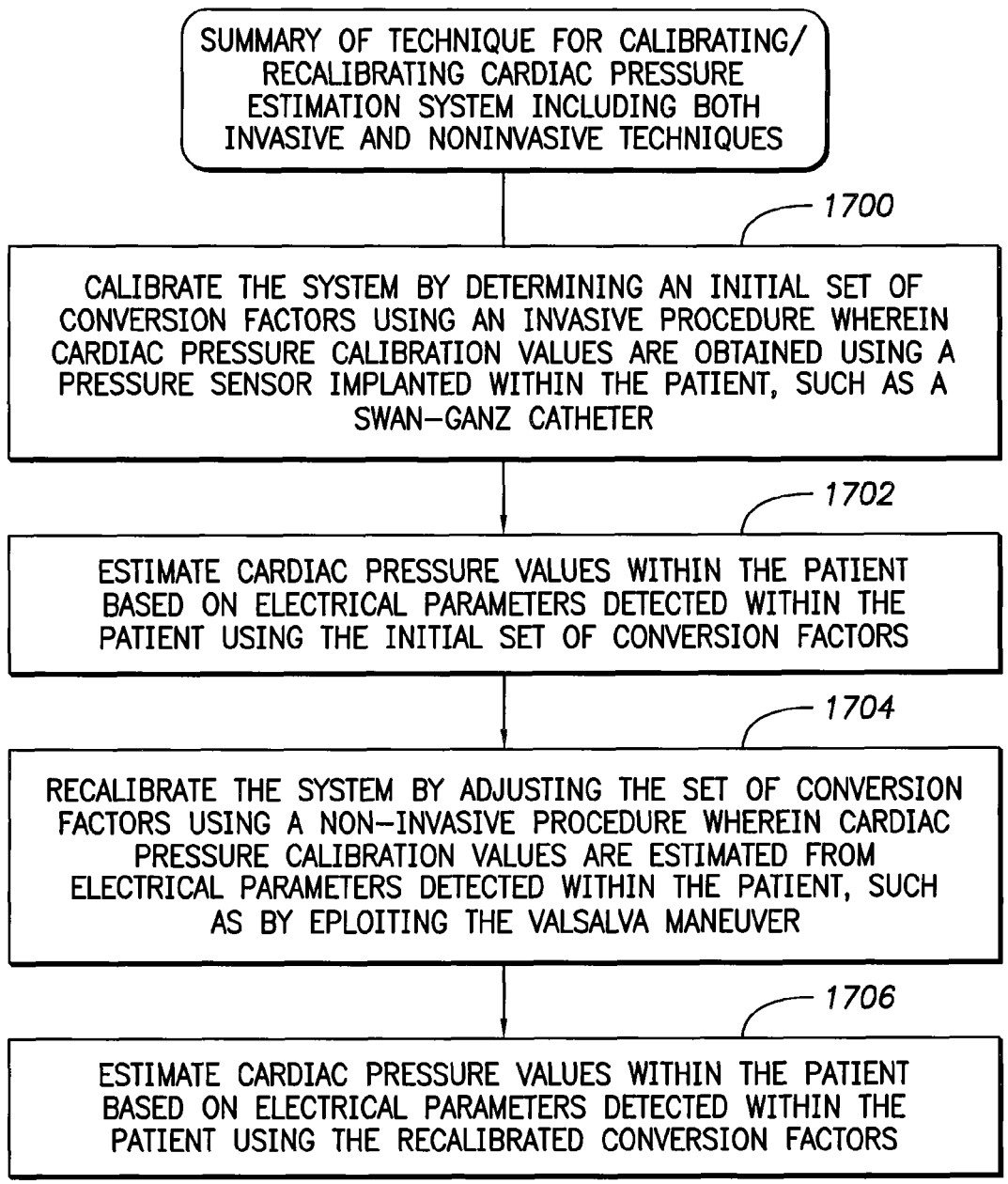
FIG. 38 is a flow diagram summarizing a technique for calibrating/recalibrating a cardiac pressure estimation system of an implantable medical device, such as the device of FIG. 1, wherein both invasive and non-invasive calibration procedures are exploited.

Turning now to the FIGS. 38-41, various techniques for employing both invasive and noninvasive calibration techniques will be described. FIG. 38 provides a summary of these techniques wherein, in general, an invasive calibration procedure is initially performed within a clinical site to determine an initial set of conversion factors. Thereafter, one or more and noninvasive calibration procedures may be performed to update the conversion factors within the patient.

Beginning at step 1700 of FIG. 38, the LAP estimation system of an implanted device is calibrated by determining an initial set of conversion factors (such as slope and baseline values) using an invasive procedure wherein cardiac pressure calibration values are obtained using a pressure sensor implanted within the patient. A Swan-Ganz catheter with a PCWP sensor may be employed. At step 1702, cardiac pressure values are then estimated within the patient based on electrical parameters, such as impedance, admittance and conductance values, detected within the patient and while using the initial set of conversion factors. (Typically chronic-state conversion factors are used at step 1702. Though, as noted, in some implementations acute-state conversion factors may be selectively used.) The estimates at step 1702 may be performed continuously or periodically over a period of months.

Eventually, the pressure estimation system of the implanted device is recalibrated at step 1704 by adjusting the set of conversion factors using a non-invasive procedure exploiting the Valsalva maneuver, or the like. In general, any of the non-invasive calibration techniques discussed in any figures above may be employed. Finally, at step 1706, cardiac pressure values are then estimated from the patient based on electrical parameters detected within the patient, and by applying the recalibrated conversion factors. Again, these estimates may be performed continuously or periodically over a period of months.

Thus, FIG. 38 broadly outlines a multi-stage calibration/recalibration procedure wherein an invasive calibration is initially performed, followed by one or more non-invasive recalibration procedures.

Figure 39:
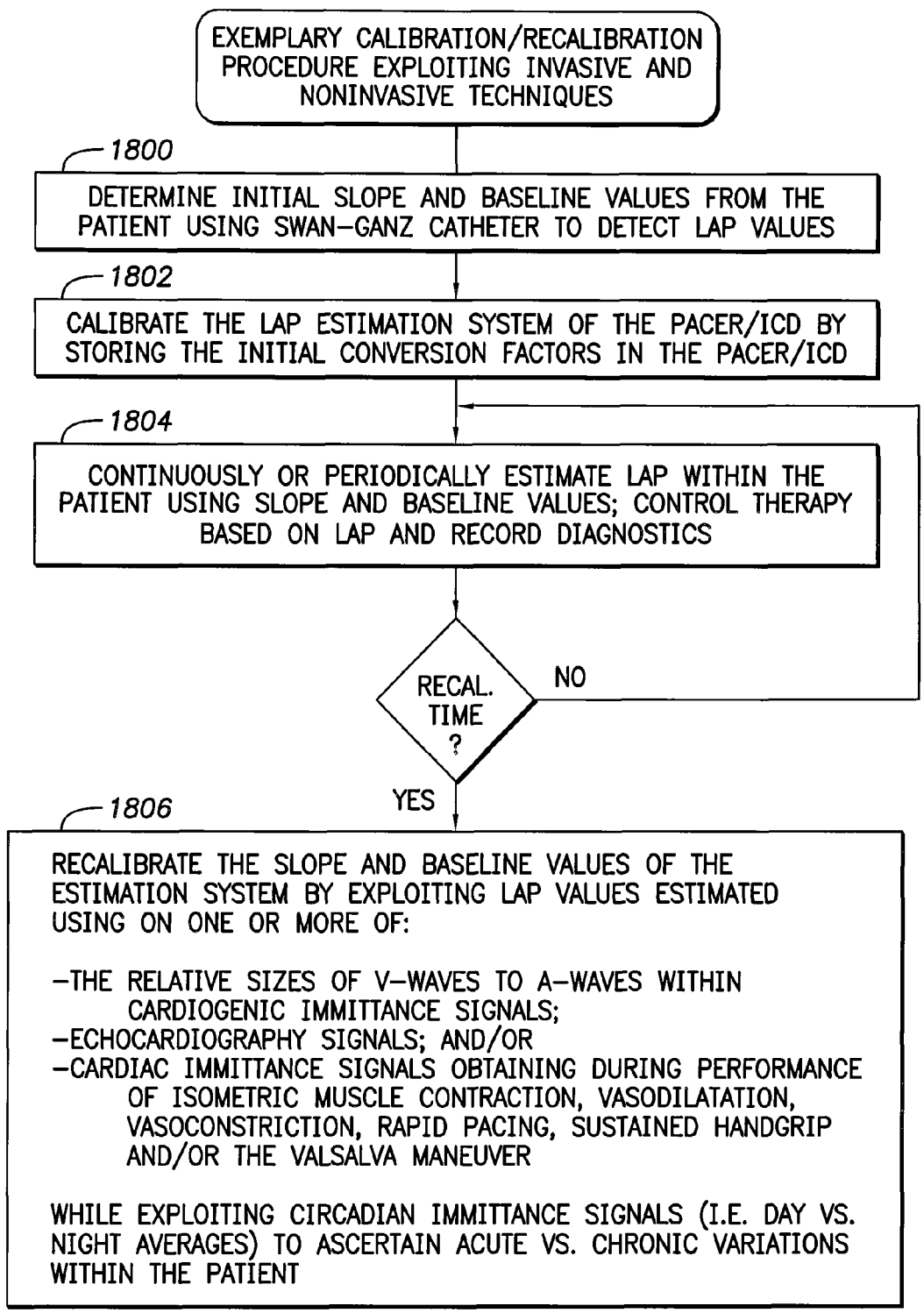
FIG. 39 is a flow diagram illustrating an exemplary technique for calibrating/recalibrating a cardiac pressure estimation system in accordance with the general technique of FIG. 38, wherein both invasive and non-invasive calibration procedures are exploited along with circadian immittance values.

FIG. 39 illustrates an exemplary implementation of this general procedure. Beginning at step 1800, initial slope and baseline values are determined for a particular patient using a Swan-Ganz catheter to detect LAP values. At step 1802, the LAP estimation system is then calibrated by storing of the initial conversion factors in the pacer/ICD of the patient. At step 1804, LAP is estimated in the patient, either continuously or periodically, using the slope and baseline values. At this time, therapy may be controlled based on the estimated LAP, diagnostics may be recorded, and appropriate warning signals may be generated, indicative of any significant changes in LAP.

Eventually, when recalibration is indicated (typically after some period of time such as after three to six months), step 1806 is then performed to recalibrate the LAP estimation system. That is, at step 1806, the slope and baseline values are recalibrated by exploiting LAP values estimated non-invasively using one or more of: the relative sizes of "V-waves" and "A-waves" observed within cardiogenic impedance signals; echocardiography signals; and/or cardiac impedance signals obtained during performance of isometric muscle contraction, vasodilatation, vasoconstriction, rapid pacing, sustained handgrip and/or the Valsalva maneuver. These are just examples. In general, any suitable non-invasive recalibration technique may be exploited at step 1806 including any of the noninvasive techniques discussed above in connection with FIGS. 1-37. Processing returns to step 1804 where the device continues to estimate LAP, now using the updated slope and baseline values obtained during recalibration.

Insofar as the relative sizes of V-waves and A-waves is concerned, the V-wave becomes bigger with larger LAP; the A-wave remains relatively fixed. (The size of the V-wave is correlated with to venous filling into atrium. The size of to A-wave correlated with atrial contraction.) These V-waves and A-waves should not be confused with V-pulses or A-pulses (i.e. pacing pulses), nor should they be confused with R-waves or P-waves of an IEGM. Insofar as echocardiography is concerned, the size of the LA atrium determined by a non-invasive echocardiography examination may be used to estimate LAP. A larger atrium may have a higher LAP. The Mitral valve regurgitation jet may also be used to estimate the LAP. A higher jet correlates with a higher LAP.

Note that as far as the use of echocardiography and the use of A-waves/V-waves is concerned, these techniques are not limited for use in calibrating an immittance-based LAP estimation system. Rather, these techniques may be exploited as stand-alone techniques for estimating LAP or other forms of cardiac pressure. That is, they are techniques that do not necessarily rely on impedance/admittance measurements. For example, the A-waves and V-waves might be directly sensed via a sensor, then used to estimate LAR Preferably, the non-invasive recalibration procedure of step 1806 also exploits circadian impedance signals to ascertain acute versus chronic fluid variations within the patient. By exploiting circadian impedance or admittance signals, the aforementioned differences between the acute and chronic fluid states may be taken into account during recalibration. In general, during the day, the patient is more likely to be within an acute state in the upright standing posture whereas, at night, the patient is more likely to be within the chronic steady state following a prolonged period of sleep. Accordingly, this information can be exploited to aid in the recalibration of the slope and baseline values. In one example, if there is little or no variation between the day and night, this indicates the patient is remaining substantially in the chronic state and is largely inactive. As such, it may not be necessary to use separate acute state conversion factors (as in FIG. 36). Rather, it may be sufficient to use only chronic state conversion factors. Within patients where there are significant impedance variations between day and night, such indicates that the patient is in the acute state by day, and in the chronic state by night. LAP estimates/admittance values obtained during the day maybe compared against LAP estimates/admittance values obtained during the day to help recalibrate the slope and baseline values.

Figure 40:
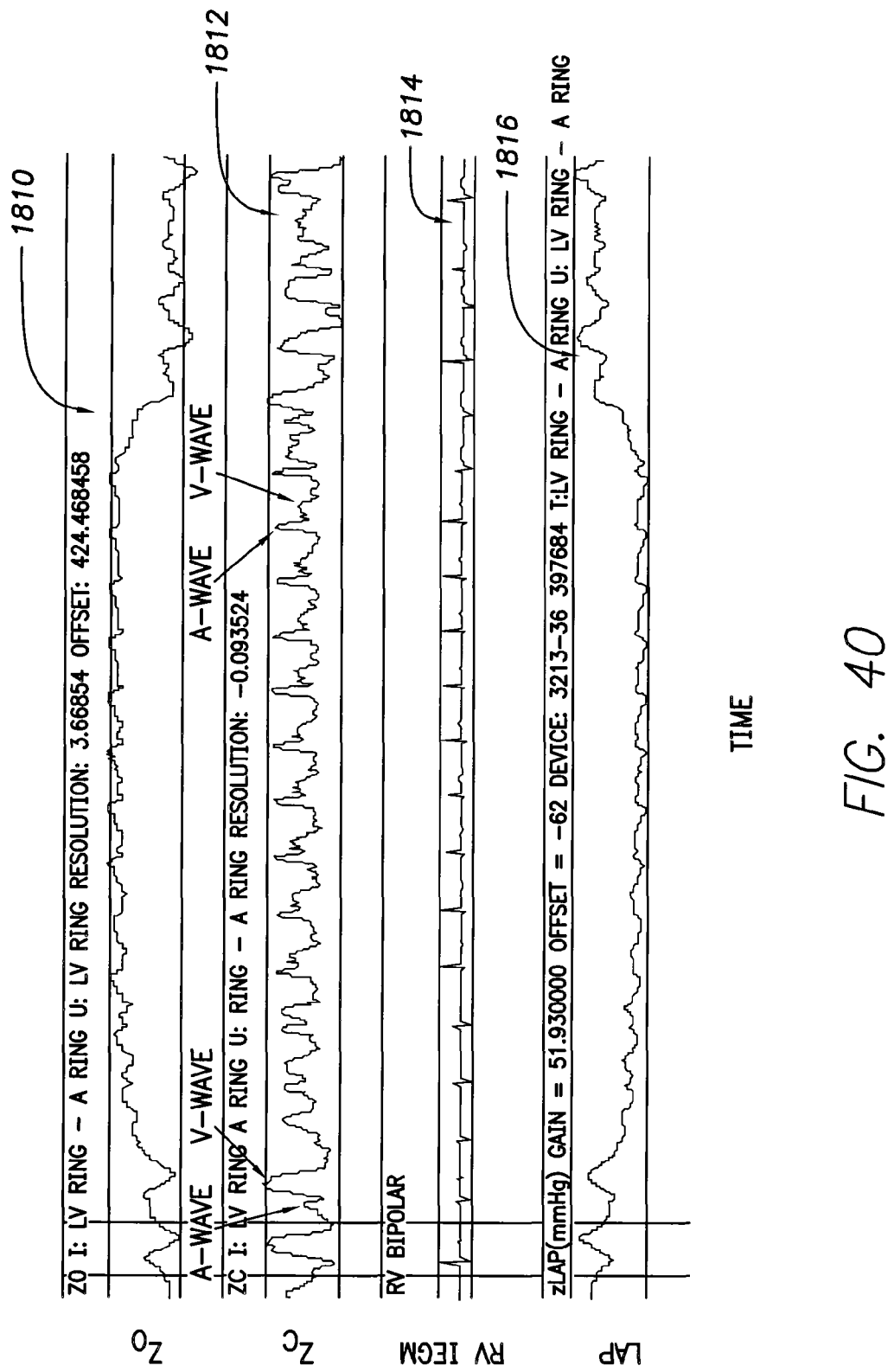
FIG. 40 is a graph illustrating time-varying impedance, LAP and voltage values for use during the non-invasive calibration of FIG. 39.

FIG. 40 illustrates some of the variations in signal values that may be used to aid in noninvasive recalibration, or which may be displayed as diagnostics data. In particular, a first graph 1810 illustrates time-varying changes in raw impedance within the patient. The graph illustrates variations occurring during a Valsalva maneuver. Graph 1812 also illustrates impedance, however whereas in graph 1810 is raw impedance, graph 1814 illustrates filtered impedance signals indicative of cardiogenic variations in impedance. Graph 1814 also illustrates exemplary A-waves and V-waves. During the Valsalva maneuver the size of the V-wave decreases relative the size of the A-wave. Graph 1814 is an RV IEGM illustrating voltage changes due to atrial and ventricular depolarization, including R-waves (i.e. QRS complexes) and T-waves. Graph 1816 illustrates variations in zLAP, which incorporate both the high-frequency (i.e. cardiogenic) variations caused by the beating the heart, as well as slower and more significant variations due to the Valsalva maneuver.

Figure 41:
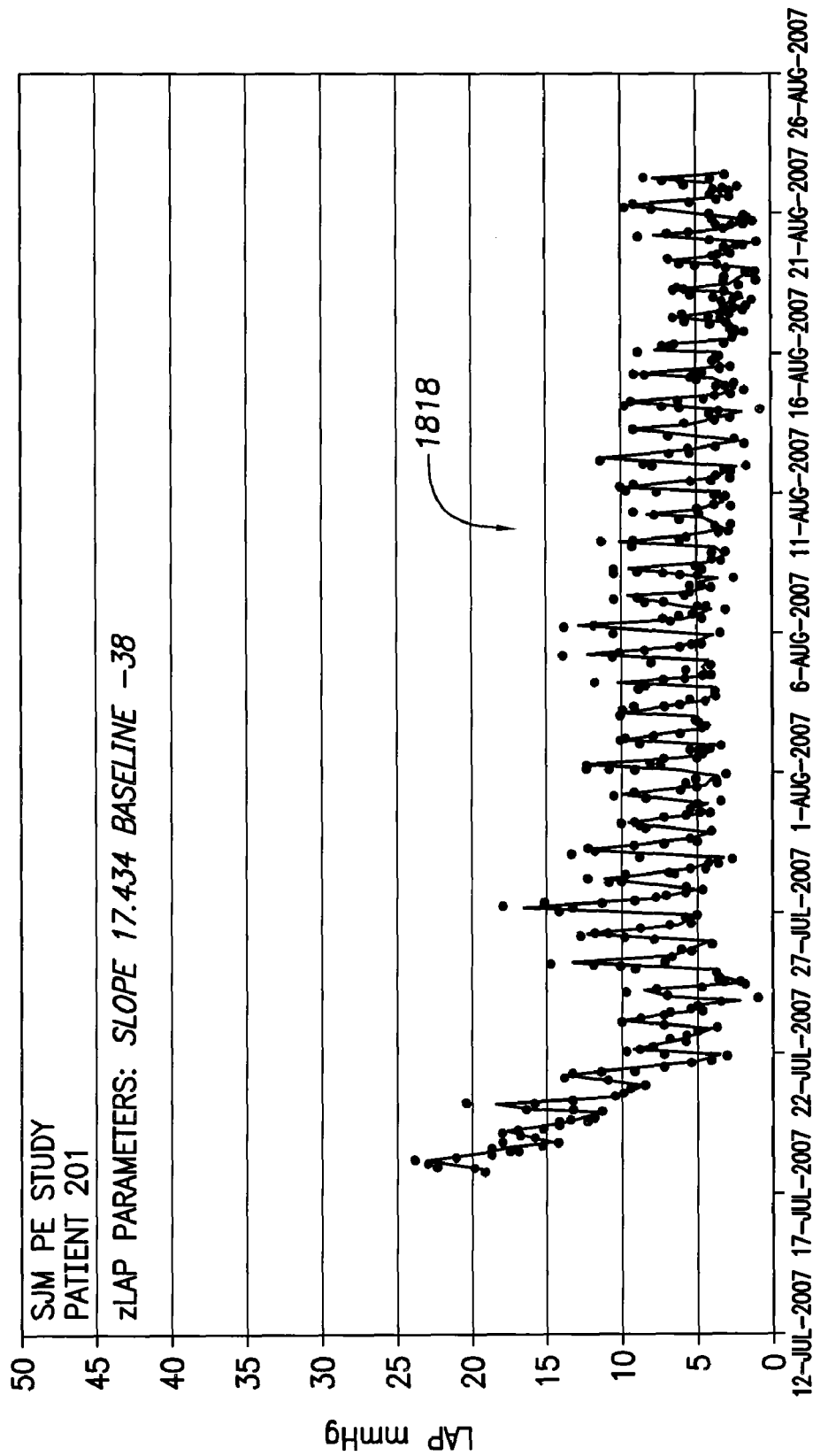
FIG. 41 is a graph illustrating circadian variations in LAP for use during the non-invasive calibration of FIG. 39.

FIG. 41 illustrates the aforementioned circadian variations in impedance over a period of about five weeks via graph 1818. The data points shown in this figure represent individual impedance measurements in ohms that were subsequently converted into zLAP estimates in mmHg using the listed conversions factors. As can be seen, there are significant diurnal variations in zLAP within this particular test subject, with relatively high zLAP during the night and relatively low zLAP during the day. The high zLAP values correspond to the night time measurements when the central venous volume is increased; whereas the low zLAP values correspond to the day time measurements when the central venous volume is reduced secondary to pooling of fluid within the lower extremities. Note also that within FIG. 41 there is an initial significant reduction in zLAP values during the first few days. This is due to transient effects caused by the initial implantation of the leads used to sense impedance values for use in estimating the LAP values. This initial period corresponds to the lead maturation interval in which acute inflammation occurs around the lead/device implant site. Even during that period of time, circadian variations are visible.

In order to calibrate conversion factors based on the data in FIG. 41, the following strategy may be used, or similar variations. The night time maximum zLAP is determined for a series of days (e.g., 7 to 10 days) proceeding the calibration session. The night time maximum zLAP typically occurs several hours (e.g., 4 hours) after the patient has gone to sleep in a resting supine/prone/lateral decubitus position, such that it is representative of the chronic steady state after the intravascular and interstitial fluid compartments have had sufficient time to equilibrate. The series of zLAP night time maximums is then averaged to determine a representative average maximum night time admittance value ($Y_{MAX\ NIGHT}$). The patient subsequently arrives to the cardiac catheterization laboratory in midday to undergo a calibration session. Upon arrival the patient undergoes a Valsalva maneuver in the standing upright position. During the Valsalva maneuver the admittance value will be measured ($Y_{Valsalva}$). This measurement is expected to be representative of the lowest achievable admittance value when the fluid within the intra-vascular and interstitial compartments is the lowest as a result of pooling of fluids within the lower extremities and the reduced venous return to the heart while performing the Valsalva maneuver.

Following this measurement, a right heart catheterization procedure is performed and the PCWP is measured in the supine resting state (PCWPsupine). Since the PCWP is a pressure measurement within the fast responding intra-vascular fluid compartment, several minutes after the patient has been placed in the supine position produces a relatively stable PCWP measurement. This is unlike the impedance measurement which reflects the fluid volume distributed within the intra-vascular and interstitial fluid compartments, where a longer period of time is required for both the intra-vascular and interstitial fluid compartments to equilibrate in order to produce a stable impedance measurement. Assuming that in the week prior to the calibration session the patient had relatively stable and consistent night time maximum admittance measurements, the representative night time maximum average admittance ($Y_{MAX\ NIGHT}$) may be used to represent the chronic steady state resting supine admittance measurement. The new slope may subsequently be determined as follows:

$$\text{New Slope} = PCWP_{supine}/(Y_{MAX\ NIGHT} - Y_{Valsalva})$$

Alternatively, one may use the minimum recorded admittance during the past 30 to 60 days ($Y_{MIN}$) instead of the admittance measured during the Valsalva maneuver to derive the new slope as follows:

$$\text{New Slope} = PCWP_{supine}/(Y_{MAX\ NIGHT} - Y_{MIN})$$

Once the New Slope is derived a New Baseline may be computed as follows:

$$\text{New Baseline} = PCWP_{supine} - \text{New Slope} \cdot Y_{MAX\ NIGHT}$$

Day vs. Night Therapy Control

Figure 42:
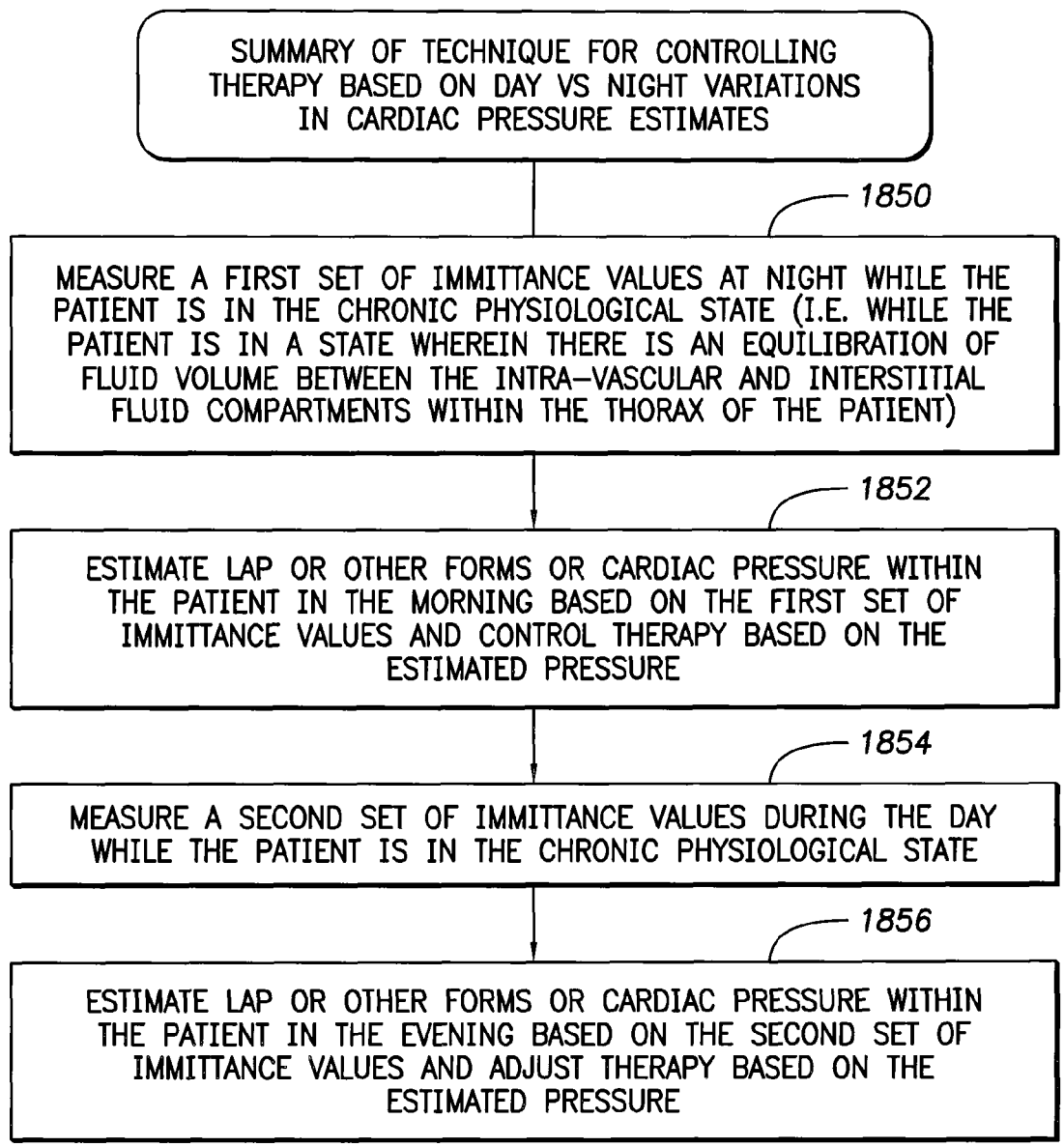
FIG. 42 is a flow diagram summarizing a technique for controlling therapy based on cardiac pressure using an implantable medical device, such as the device of FIG. 1, wherein both day time vs. night time immittance measurements are exploited.

FIG. 42 summarizes a method for controlling therapy based on cardiac pressure estimations, which exploit day vs. night chronic state measurements. Briefly, at step 1850, a first set of admittance/impedance values are measured at night within the patient by the pacer/ICD while the patient is in the chronic physiological state (i.e. corresponding to a state wherein there is an equilibration of fluid volume between the intra-vascular and interstitial fluid compartments within the thorax of the patient.) At step 1852, LAP or other forms or cardiac pressure are then estimated within the patient in the morning based on the first set of admittance/impedance values. Therapy is controller based on the estimated cardiac pressure. For example, daily medications can be titrated based on a morning LAP estimate made at, e.g., 8:00 am. At step 1854, a second set of admittance/impedance values are measured during the day within the patient while the patient is also in the chronic physiological state. At step 1856, LAP or other forms of cardiac pressure are then estimated within the patient in the evening based on the second set of immittance values. Further therapy is controlled based on the newly estimated cardiac pressure. For example, nightly medications can be titrated based on the evening LAP estimate.

The various conversion techniques already exploited can be used to estimate LAP from admittance/impedance values based on slope and baseline conversion factors. In one particular example, the pacer/ICD uses the maximum average admittance measured overnight (i.e. $Y_{MAX\ NIGHT}$) for use in estimating the LAP in the morning and instead uses the minimum average admittance measured during the day (i.e. $Y_{MIN\ DAY}$) for use in estimating the LAP in the evening. The minimum daytime admittance is typically representative of the "driest" fluid state within the thorax, as that admittance value likely corresponds to a standing posture where the patient has been standing long enough to equilibrate into the corresponding chronic fluid state. The maximum nighttime admittance is typically representative of the "wettest" fluid state within the thorax, as that admittance value likely corresponds to a supine/prone posture where the patient has been lying long enough to equilibrate into the corresponding chronic fluid state. Hence, these values are helpful in determining the appropriate therapy for the patient at steps 1852 and 1854.

Depending upon the particular implementation, therapy may be directly controlled by the implanted device using, e.g., a drug pump. Alternatively, the device can transmit control signals to an external device for directing the patient or caregiver to select the appropriate medications to be administered to the patient. In this manner, daily titration of medications can be achieved.

Alternative Implementation of Exemplary Pacer/ICD

Figure 43:
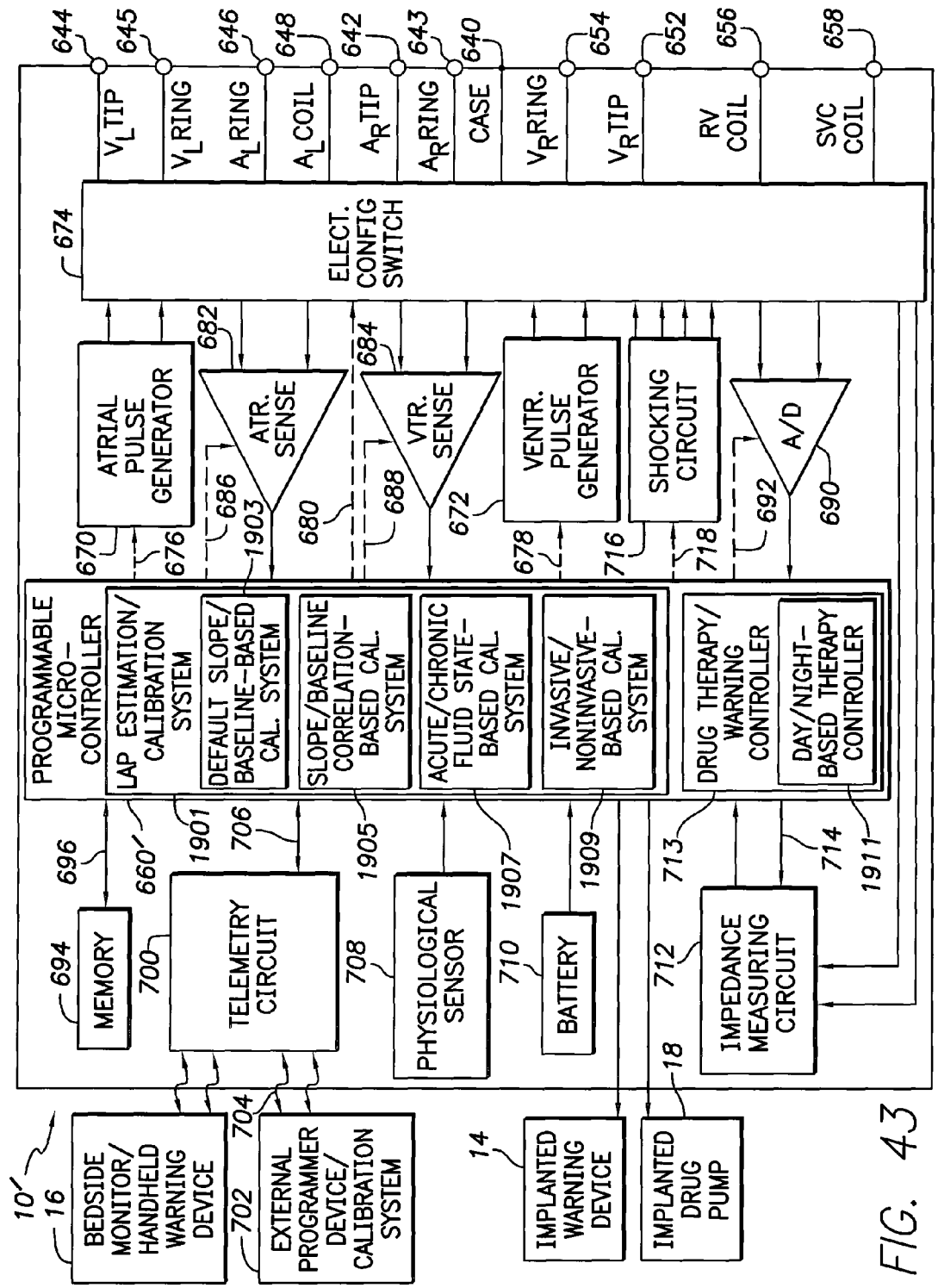
FIG. 43 is another illustrative implementation of the pacer/ICD of FIG. 19, particularly illustrating components for estimating/calibrating LAP using the techniques of FIGS. 23-42.

FIG. 43 illustrates an alternative implementation of a pacer/ICD to that of FIG. 20, which includes components for implementing the techniques of FIGS. 23-41. Most of the components of device 10' of FIG. 43 are the same or similar to corresponding components of device 10 FIG. 20 and will not be described. Briefly, microcontroller 660' of device 10' of FIG. 43 includes an LAP estimation/calibration system 1901 that includes a default slope/baseline-based calibration system 1903 operative to perform or coordinate the functions described with respect to FIGS. 23-24, either alone in conjunction with an external system, such as an external programmer. A slope/baseline correlation-based calibration system 1905 is operative to perform or coordinate the functions described with respect to FIGS. 25-27, again either alone in conjunction with an external system. An acute/chronic fluid state-based calibration system 1907 is operative to perform or coordinate the functions described with respect to FIGS. 28-34, again either alone in conjunction with an external system. An invasive/noninvasive-based calibration system 1909 is operative to perform or coordinate the functions described with respect to FIGS. 35-41, again either alone in conjunction with an external system. The Drug Therapy/ Warning Controller 713 may take advantage of the acute and chronic fluid states by basing therapy on either the acute or chronic fluid state determined. For example, the drug therapy determined in the morning may be based on a chronic steady state measurement obtained at night time (i.e., the maximum night time admittance) after sufficient time has elapsed to allow the intra-vascular and interstitial fluid compartments to equilibrate. That is, a day/night-based therapy control system 1911 may be provided, which is operative to perform or coordinate the functions described with respect to FIG. 42, again either alone in conjunction with an external system. It should be understood that the various components of the microprocessor of FIG. 20 may also be implemented within the device of FIG. 43.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using ASICs or the like.

In general, while the invention has been described with reference to particular embodiments, modifications can be made thereto without departing from the spirit and scope of the invention. Note also that the term "including" as used herein is intended to be inclusive, i.e. "including but not limited to".

What is claimed is:

1. A method for estimating cardiac pressure within a patient using an implantable medical device wherein the estimation exploits conversion factors representative of a correlation between a measured electrical parameter within the patient and the cardiac pressure of the patient, the method comprising:
   determining a set of conversion factors for converting measured electrical parameters to estimates of cardiac pressure, wherein the conversion factors are determined, at least in part, based on a physiological state of the patient and wherein the physiological state is either an acute state wherein an acute change of fluid volume within the intra-vascular fluid compartment of the patient does not substantially affect the fluid volume within the interstitial fluid compartment of the patient or a chronic state wherein fluid volume between the intra-vascular and interstitial fluid compartments of the patient has substantially equilibrated; and
   estimating cardiac pressure within the patient by applying a first set of conversion factors to measured electrical parameters when the patient is in the acute state and a second set of conversion factors to measured electrical parameters when the patient is in the chronic state.

2. The method of claim 1 wherein determining the set of conversion factors includes:
   inputting a first set of conversion factors appropriate for converting electrical parameters measured while the patient is in the acute state;
   inputting an adjustment factor for use in adjusting the first set of conversion factors to yield a second set of conversion factors appropriate for use with electrical parameters measured while the patient is in the chronic state; and
   applying the adjustment factor to the first set of conversion factors to generate the second set of conversion factors.

3. The method of claim 2 wherein the first and second sets of conversion factors include slope and baseline values representative of a linear relationship between the measured parameter and cardiac pressure and wherein the adjustment factor is applied only to the slope value.

4. The method of claim 3 wherein the slope of the first set of conversion factors is adjusted by dividing the slope by adjustment factor in the range of 3 to 5 to yield the slope of the second set of conversion factors.

5. The method of claim 2 wherein adjustment factor is specific to the particular patient in which the device is implanted.

6. The method of claim 1 wherein determining the set of conversion factors includes:
   determining the current patient physiological state of the patient; and
   retrieving and applying the appropriate set of conversion factors for the current physiological state.

7. The method of claim 6 wherein the implantable device stores a first set of conversion factors appropriate for use in the acute state and a second set of conversion factors appropriate for use in the chronic state.

8. A method for estimating cardiac pressure within a patient using an implantable medical device wherein the estimation exploits conversion factors representative of a correlation between a measured electrical parameter within the patient and the cardiac pressure of the patient, the method comprising:
   determining a set of conversion factors for converting measured electrical parameters to estimates of cardiac pressure, wherein determining the set of conversion factors includes:
   determining a first set of acute conversion factors based, at least in part, on calibration parameters measured while the patient is in an acute physiological state affecting only the fluid volume within the intra-vascular fluid compartment; and
   determining a second set of chronic conversion factors based, at least in part, on calibration parameters measured while the patient is in a chronic steady state in which the fluid volume within the intra-vascular and interstitial fluid compartments have equilibrated; and
   estimating cardiac pressure within the patient by applying the first set of conversion factors to measured electrical parameters if the patient is in the acute physiological state and applying the second set of conversion factors to measured electrical parameters if the patient is in the chronic steady state.

* * * * *